US012774284B2

(12) United States Patent
Wang et al.

(10) Patent No.: US 12,774,284 B2
(45) Date of Patent: Oct. 27, 2026

(54) ELECTROLUMINESCENT DEVICE

(71) Applicant: BEIJING SUMMER SPROUT TECHNOLOGY CO., LTD., Beijing (CN)

(72) Inventors: Le Wang, Beijing (CN); Chi Yuen Raymond Kwong, Beijing (CN); Qiang Wang, Beijing (CN); Han Zhang, Beijing (CN); Junfei Wang, Beijing (CN); Menglan Xie, Beijing (CN); Chuanjun Xia, Beijing (CN)

(73) Assignee: BEIJING SUMMER SPROUT TECHNOLOGY CO., LTD., Beijing (CN)

(*) Notice: Subject to any disclaimer, the term of this patent is extended or adjusted under 35 U.S.C. 154(b) by 1134 days.

(21) Appl. No.: 17/541,788

(22) Filed: Dec. 3, 2021

(65) Prior Publication Data

US 2022/0274998 A1 Sep. 1, 2022

(30) Foreign Application Priority Data

Dec. 4, 2020 (CN) ........................ 202011397603.1

(51) Int. Cl.
*C07D 487/16* (2006.01)
*C07D 209/94* (2006.01)
(Continued)

(52) U.S. Cl.
CPC ......... *C07D 487/16* (2013.01); *C07D 209/94* (2013.01); *C07D 471/22* (2013.01);
(Continued)

(58) Field of Classification Search
CPC ................ C07D 487/16; C07D 491/06; C07D 209/94; H10K 85/342; C07F 15/0033
See application file for complete search history.

(56) References Cited

U.S. PATENT DOCUMENTS 5,703,436 A 12/1997 Forrest et al.
5,707,745 A 1/1998 Forrest et al.
(Continued)

FOREIGN PATENT DOCUMENTS

CN 109956977 A 7/2019
CN 111039928 A 4/2020
(Continued)

OTHER PUBLICATIONS

Google Translation of KR 20150077220 A (Year: 2025).*
(Continued)

*Primary Examiner* — Michael M Dollinger
(74) *Attorney, Agent, or Firm* — KDW FIRM PLLC

(57) ABSTRACT

Provided is an electroluminescent device. The electroluminescent device includes an anode, a cathode, and an organic layer disposed between the anode and the cathode, wherein the organic layer at least comprises a first compound having a structure of $H_1$-$L_1$-$Ar_1$ and a second compound having a structure of $H_2$-$L_2$-$Ar_2$. These new compound combinations can be used as host materials in electroluminescent devices. These new compound combinations can greatly improve the lifetime of the device and provide the device with better performance. Further provided is a display assembly including the electroluminescent device.

23 Claims, 2 Drawing Sheets

(51) Int. Cl.

| | |
|---|---|
| ***C07D 471/22*** | (2006.01) |
| ***C07D 487/22*** | (2006.01) |
| ***C07D 491/06*** | (2006.01) |
| ***C07D 491/22*** | (2006.01) |
| ***C07D 495/06*** | (2006.01) |
| ***C07D 495/22*** | (2006.01) |
| ***H10K 85/60*** | (2023.01) |
| *H10K 50/11* | (2023.01) |
| *H10K 101/00* | (2023.01) |
| *H10K 101/10* | (2023.01) |

(52) U.S. Cl.

CPC ......... *C07D 487/22* (2013.01); *C07D 491/06* (2013.01); *C07D 491/22* (2013.01); *C07D 495/06* (2013.01); *C07D 495/22* (2013.01); *H10K 85/657* (2023.02); *H10K 85/6572* (2023.02); *C07B 2200/05* (2013.01); *H10K 50/11* (2023.02); *H10K 2101/10* (2023.02); *H10K 2101/90* (2023.02)

(56) References Cited

U.S. PATENT DOCUMENTS

| | | | | |
|---|---|---|---|---|
| 5,844,363 | A | 12/1998 | Gu et al. | |
| 6,097,147 | A | 8/2000 | Baldo et al. | |
| 6,303,238 | B1 | 10/2001 | Thompson et al. | |
| 7,279,704 | B2 | 10/2007 | Walters et al. | |
| 7,968,146 | B2 | 6/2011 | Wagner et al. | |
| 12,156,466 | B2 * | 11/2024 | Wang | C09K 11/06 |
| 2003/0230980 | A1 | 12/2003 | Forrest et al. | |
| 2004/0174116 | A1 | 9/2004 | Lu et al. | |
| 2015/0236277 | A1 * | 8/2015 | Boudreault | C07F 15/0033 257/40 |
| 2015/0349273 | A1 | 12/2015 | Huang et al. | |
| 2016/0359122 | A1 | 12/2016 | Boudreault et al. | |
| 2018/0337340 | A1 * | 11/2018 | Moon | C09K 11/06 |
| 2021/0043848 | A1 * | 2/2021 | Kim | C07D 209/94 |
| 2022/0077404 | A1 | 3/2022 | Zhang et al. | |
| 2022/0177502 | A1 | 6/2022 | Wang et al. | |
| 2022/0231232 | A1 | 7/2022 | Wang et al. | |
| 2022/0289681 | A1 | 9/2022 | Wang et al. | |

FOREIGN PATENT DOCUMENTS

| | | | | |
|---|---|---|---|---|
| CN | 111868210 | A | 10/2020 | |
| CN | 111909213 | A | 11/2020 | |
| CN | 112582555 | A * | 3/2021 | H10K 50/12 |
| CN | 112876489 | A | 6/2021 | |
| CN | 113527315 | A | 10/2021 | |
| CN | 113527316 | A | 10/2021 | |
| CN | 113527317 | A | 10/2021 | |
| CN | 113968873 | A | 1/2022 | |
| CN | 113968875 | A | 1/2022 | |
| CN | 114075208 | A | 2/2022 | |
| CN | 114256430 | A | 3/2022 | |
| CN | 114835718 | A | 8/2022 | |
| KR | 1020150077220 | A | 7/2015 | |
| KR | 1020210047053 | A | 4/2021 | |
| WO | WO-2019177407 | A1 * | 9/2019 | C07D 209/94 |

OTHER PUBLICATIONS

Tang et al., "Organic electroluminescent diodes," Appl. Phys. Lett. 51(12), pp. 913-915, DOI:10.1063/1.98799 (1987).

Joyama et al., "Highly efficient organic light-emitting diodes from delayed fluorescence," Nature 492, pp. 234-240, DOI:10.1038/nature11687 (Dec 2012).

Chinese Notice of the First Examination Opinion issued in CN Application No. 202011397603.1 on Jul. 25, 2024 and English translation, 26 pages.

* cited by examiner

ELECTROLUMINESCENT DEVICE

CROSS-REFERENCE TO RELATED APPLICATION(S)

This application claims priority to Chinese Patent Application No. CN 202011397603.1 filed on Dec. 4, 2020, the disclosure of which is incorporated herein by reference in its entirety.

TECHNICAL FIELD

The present disclosure relates to organic electronic devices, for example, an organic electroluminescent device. More particularly, the present disclosure relates to an organic electroluminescent device at least containing a new compound combination of a first compound having a structure of $H_1$-$L_1$-$Ar_1$ and a second compound having a structure of $H_2$-$L_2$-$Ar_2$ in an organic layer, and an electronic apparatus comprising the organic electroluminescent device.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This device laid the foundation for the development of modem organic light-emitting diodes (OLEDs). State-of-the-art OLEDs may comprise multiple layers such as charge injection and transporting layers, charge and exciton blocking layers, and one or multiple emissive layers between the cathode and anode. Since the OLED is a self-emitting solid state device, it offers tremendous potential for display and lighting applications. In addition, the inherent properties of organic materials, such as their flexibility, may make them well suited for particular applications such as fabrication on flexible substrates.

The OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of the fluorescent OLED is only 25%. This limitation hindered the commercialization of OLED. In 1997, Forrest and Thompson reported phosphorescent OLED, which uses triplet emission from heavy metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. A small molecule refers to any organic or organometallic material that is not a polymer. The molecular weight of the small molecule can be large as long as it has well defined structure. Dendrimers with well-defined structures are considered as small molecules. Polymer OLEDs include conjugated polymers and non-conjugated polymers with pendant emitting groups. Small molecule OLED can become the polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of the OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

KR1020150077220A discloses an organic electroluminescent compound having an organic optical compound of the following structure:

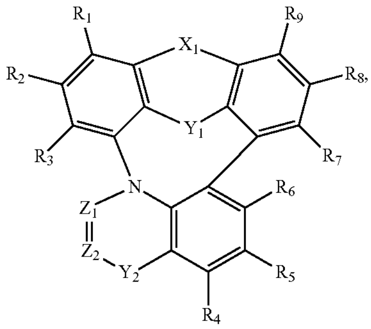

the $X_1$ of a general formula disclosed therein can be N($Ar_1$), but this disclosure does not disclose or teach the use in which such a compound and an organic compound containing an azamacrocycle fused with indole and pyrrole as well as a similar structure thereof are used together as the host material.

US20180337340A1 discloses an organic electroluminescent compound and an organic electroluminescent device comprising the same. The organic electroluminescent device includes an organic layer containing one or more hosts, where a first host is an organic optical compound having the following structure:

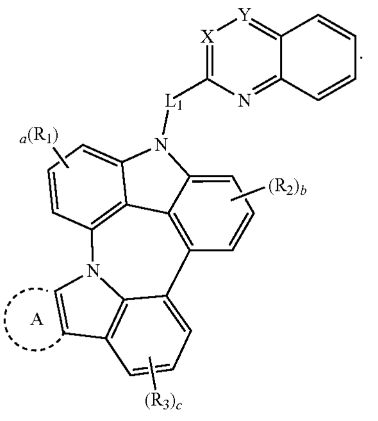

However, this disclosure does not disclose or teach the use in which such a compound and an organic compound containing an azamacrocycle fused with indole and pyrrole as well as a similar structure thereof are used together as the host material.

However, there is still room for improvement in various reported host materials. In order to meet the increasing demands of the industry, it is efficient research and development means to select and combine appropriate host materials. New material combinations still need be further researched and developed to meet the increasing demands of the industry for device performance.

SUMMARY

The present disclosure aims to provide an electroluminescent device containing a new compound combination in the organic layer to solve at least part of the above-mentioned problems. The new compound combination contains a combination of a first compound having a structure of $H_1$-$L_1$-$Ar_1$ and a second compound having a structure of $H_2$-$L_2$-$Ar_2$, and this new material combination can be used as the host material of the electroluminescent device. This new material combination can greatly improve the lifetime of the device and provide the device with better performance.

According to an embodiment of the present disclosure, disclosed is an electroluminescent device, comprising:

an anode, a cathode, and an organic layer disposed between the anode and the cathode, wherein the organic layer comprises at least a first compound and a second compound, and the first compound and the second compound are different;

the first compound has a structure of $H_1$-$L_1$-$Ar_1$; wherein the $H_1$ has a structure represented by Formula 1:

Formula 1

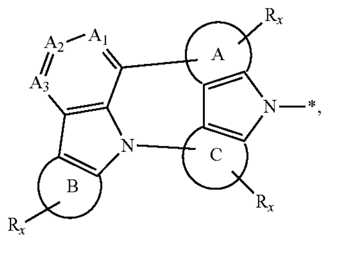

in Formula 1, $A_1$, $A_2$, and $A_3$ are, at each occurrence identically or differently, selected from N or CR, and ring A, ring B, and ring C are, at each occurrence identically or differently, selected from a carbocyclic ring having 5 to 30 carbon atoms or a heterocyclic ring having 3 to 30 carbon atoms;

$R_x$ represents, at each occurrence identically or differently, mono-substitution, multiple substitutions or non-substitution;

adjacent substituents R, $R_x$ can be optionally joined to form a ring;

$L_1$ is selected from a single bond, substituted or unsubstituted arylene having 6 to 30 carbon atoms, substituted or unsubstituted heteroarylene having 3 to 30 carbon atoms, or combinations thereof;

$Ar_1$ is selected from substituted or unsubstituted aryl having 6 to 30 carbon atoms or substituted or unsubstituted heteroaryl having 3 to 30 carbon atoms;

the second compound has a structure of $H_2$-$L_2$-$Ar_2$;

wherein the $H_2$ has a structure represented by Formula 2:

Formula 2

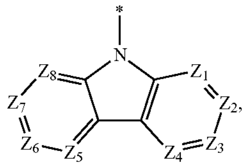

in Formula 2, $Z_1$ to $Z_3$ and $Z_6$ to $Z_8$ are, at each occurrence identically or differently, selected from $CR_{z1}$ or N, $Z_4$ and $Z_5$ are, at each occurrence identically or differently, selected from $CR_{z2}$, and two substituents $R_{z2}$ in $Z_4$ and $Z_5$ are joined to form a ring;

$Ar_2$ is selected from substituted or unsubstituted aryl having 6 to 30 carbon atoms or substituted or unsubstituted heteroaryl having 3 to 30 carbon atoms;

$L_2$ is selected from a single bond, substituted or unsubstituted arylene having 6 to 30 carbon atoms, substituted or unsubstituted heteroarylene having 3 to 30 carbon atoms, or combinations thereof;

R, $R_x$, and $R_{z1}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

$R_{z2}$ is, at each occurrence identically or differently, selected from the group consisting of: hydrogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a hydroxyl group, a sulfanyl group, a sulfinyl group, a sulfonyl group, a phosphino group, and combinations thereof;

adjacent substituents $R_{z1}$, $R_{z2}$ can be optionally joined to form a ring.

According to another embodiment of the present disclosure, further disclosed is a display assembly comprising the electroluminescent device described in the preceding embodiment.

The present disclosure provides an electroluminescent device containing a new compound combination in the organic layer. The new compound combination contains a combination of a first compound having a structure of $H_1$-$L_1$-$Ar_1$ and a second compound having a structure of $H_2$-$L_2$-$Ar_2$, and this new material combination can be used as the host material of the electroluminescent device. This new material combination can greatly improve the lifetime of the device and provide the device with better performance.

DETAILED DESCRIPTION

Figure 1:
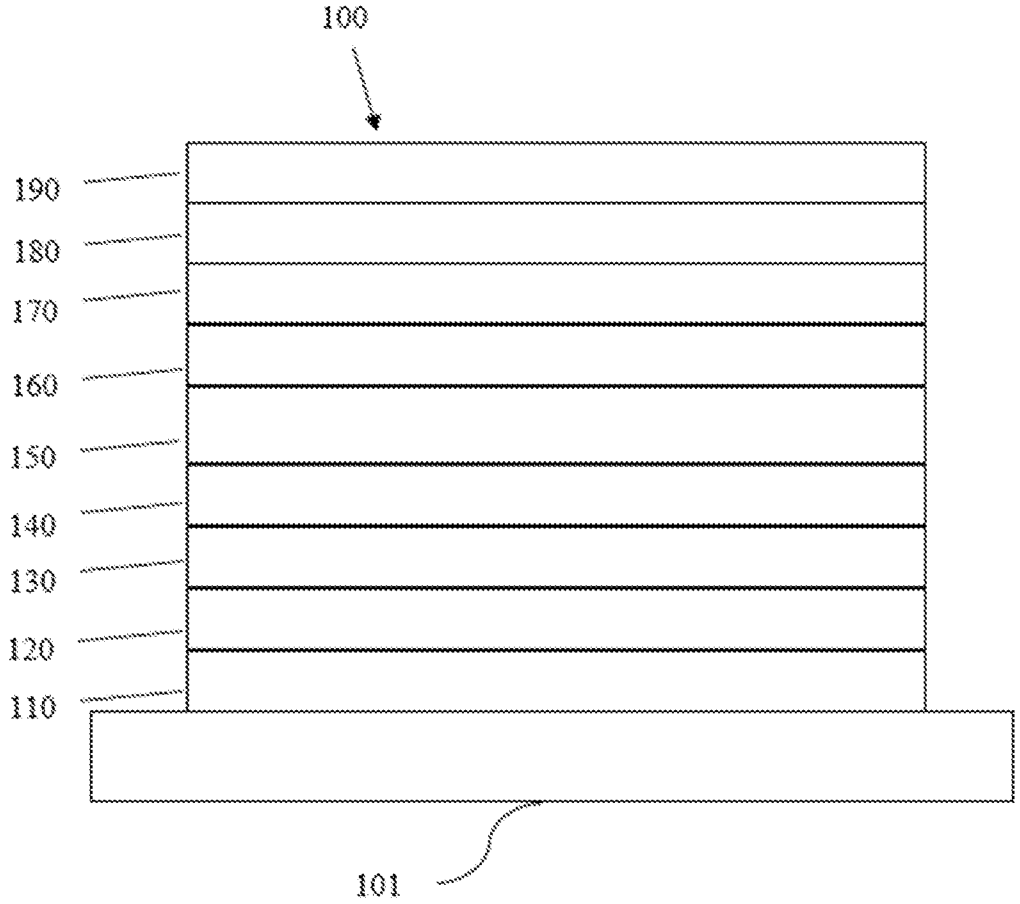
FIG. 1 is a schematic diagram of an organic light-emitting apparatus that may include an electroluminescent device disclosed by the present disclosure.

OLEDs can be fabricated on various types of substrates such as glass, plastic, and metal foil. FIG. 1 schematically shows an organic light emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers are described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting examples. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
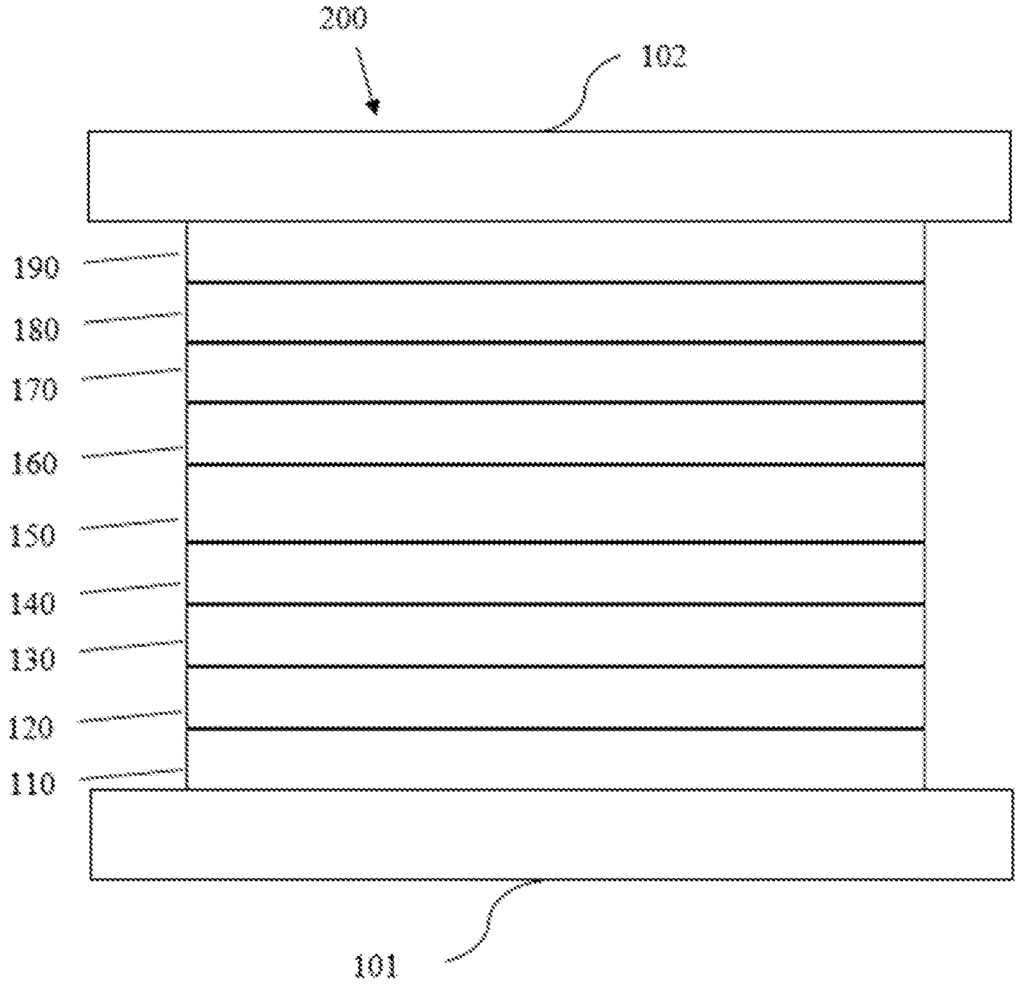
FIG. 2 is a schematic diagram of another organic light-emitting apparatus that may include an electroluminescent device disclosed by the present disclosure.

An OLED can be encapsulated by a barrier layer. FIG. 2 schematically shows an organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass or organic-inorganic hybrid layers. The barrier layer should be placed directly or indirectly outside of the OLED device. Multilayer thin film encapsulation was described in U.S. Pat. No. 7,968,146, which is incorporated by reference herein in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from the substrate. There may be other layers between the first and second layers, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is generally characterized as a donor-acceptor charge-transfer (CT) type emission. The spatial separation of the HOMO and LUMO in these donor-acceptor type compounds generally results in small $\Delta E_{S-T}$. These states may involve CT states. Generally, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—as used herein includes both straight and branched chain alkyl groups. Alkyl may be alkyl having 1 to 20 carbon atoms, preferably alkyl having 1 to 12 carbon atoms, and more preferably alkyl having 1 to 6 carbon atoms. Examples of alkyl groups include a methyl group, an ethyl group, a propyl group, an isopropyl group, a n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group. Of the above, preferred are a methyl group, an ethyl group, a propyl group, an isopropyl group, a n-butyl group, an s-butyl group, an isobutyl group, a t-butyl group, an n-pentyl group, a neopentyl group, and an n-hexyl group. Additionally, the alkyl group may be optionally substituted.

Cycloalkyl—as used herein includes cyclic alkyl groups. The cycloalkyl groups may be those having 3 to 20 ring carbon atoms, preferably those having 4 to 10 carbon atoms. Examples of cycloalkyl include cyclobutyl, cyclopentyl, cyclohexyl, 4-methylcyclohexyl, 4,4-dimethylcylcohexyl, 1-adamantyl, 2-adamantyl, 1-norbornyl, 2-norbornyl, and the like. Of the above, preferred are cyclopentyl, cyclohexyl, 4-methylcyclohexyl, and 4,4-dimethylcylcohexyl. Additionally, the cycloalkyl group may be optionally substituted.

Heteroalkyl—as used herein, includes a group formed by replacing one or more carbons in an alkyl chain with a hetero-atom(s) selected from the group consisting of a nitrogen atom, an oxygen atom, a sulfur atom, a selenium atom, a phosphorus atom, a silicon atom, a germanium atom, and a boron atom. Heteroalkyl may be those having 1 to 20 carbon atoms, preferably those having 1 to 10 carbon atoms, and more preferably those having 1 to 6 carbon atoms. Examples of heteroalkyl include methoxymethyl, ethoxymethyl, ethoxyethyl, methylthiomethyl, ethylthiomethyl, ethylthioethyl, methoxymethoxymethyl, ethoxymethoxymethyl, ethoxyethoxyethyl, hydroxymethyl, hydroxyethyl, hydroxypropyl, mercaptomethyl, mercaptoethyl, mercaptopropyl, aminomethyl, aminoethyl, aminopropyl, dimethylaminomethyl, trimethylsilyl, dimethylethylsilyl, dimethylisopropylsilyl, t-butyldimethylsilyl, triethylsilyl, triisopropylsilyl, trimethylsilylmethyl, trimethylsilylethyl, and trimethylsilylisopropyl. Additionally, the heteroalkyl group may be optionally substituted.

Alkenyl—as used herein includes straight chain, branched chain, and cyclic alkene groups. Alkenyl may be those having 2 to 20 carbon atoms, preferably those having 2 to 10 carbon atoms. Examples of alkenyl include vinyl, propenyl, 1-butenyl, 2-butenyl, 3-butenyl, 1,3-butandienyl, 1-methylvinyl, styryl, 2,2-diphenylvinyl, 1,2-diphenylvinyl, 1-methylallyl, 1,1-dimethylallyl, 2-methylallyl, 1-phenylallyl, 2-phenylallyl, 3-phenylallyl, 3,3-diphenylallyl, 1,2-dimethylallyl, 1-phenyl-1-butenyl, 3-phenyl-1-butenyl, cyclopentenyl, cyclopentadienyl, cyclohexenyl, cycloheptenyl, cycloheptatrienyl, cyclooctenyl, cyclooctatetraenyl, and norbornenyl. Additionally, the alkenyl group may be optionally substituted.

Alkynyl—as used herein includes straight chain alkynyl groups. Alkynyl may be those having 2 to 20 carbon atoms, preferably those having 2 to 10 carbon atoms. Examples of alkynyl groups include ethynyl, propynyl, propargyl, 1-butynyl, 2-butynyl, 3-butynyl, 1-pentynyl, 2-pentynyl, 3,3-dimethyl-1-butynyl, 3-ethyl-3-methyl-1-pentynyl, 3,3-diisopropyl-1-pentynyl, phenylethynyl, phenylpropynyl, etc. Of the above, preferred are ethynyl, propynyl, propargyl, 1-butynyl, 2-butynyl, 3-butynyl, 1-pentynyl, and phenylethynyl. Additionally, the alkynyl group may be optionally substituted.

Aryl or an aromatic group—as used herein includes non-condensed and condensed systems. Aryl may be those having 6 to 30 carbon atoms, preferably those having 6 to 20 carbon atoms, and more preferably those having 6 to 12 carbon atoms. Examples of aryl groups include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Examples of non-condensed aryl groups include phenyl, biphenyl-2-yl, biphenyl-3-yl, biphenyl-4-yl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-(2-phenylpropyl)phenyl, 4'-methylbiphenylyl, 4"-t-butyl-p-terphenyl-4-yl, o-cumenyl, m-cumenyl, p-cumenyl, 2,3-xylyl, 3,4-xylyl, 2,5-xylyl, mesityl, and m-quarterphenyl. Additionally, the aryl group may be optionally substituted.

Heterocyclic groups or heterocycle—as used herein include non-aromatic cyclic groups. Non-aromatic heterocyclic groups include saturated heterocyclic groups having 3 to 20 ring atoms and unsaturated non-aromatic heterocyclic groups having 3 to 20 ring atoms, where at least one ring atom is selected from the group consisting of a nitrogen atom, an oxygen atom, a sulfur atom, a selenium atom, a silicon atom, a phosphorus atom, a germanium atom, and a boron atom. Preferred non-aromatic heterocyclic groups are those having 3 to 7 ring atoms, each of which includes at least one hetero-atom such as nitrogen, oxygen, silicon, or sulfur. Examples of non-aromatic heterocyclic groups include oxiranyl, oxetanyl, tetrahydrofuranyl, tetrahydropyranyl, dioxolanyl, dioxanyl, aziridinyl, dihydropyrrolyl, tetrahydropyrrolyl, piperidinyl, oxazolidinyl, morpholinyl, piperazinyl, oxepinyl, thiepinyl, azepinyl, and tetrahydrosilolyl. Additionally, the heterocyclic group may be optionally substituted.

Heteroaryl—as used herein, includes non-condensed and condensed hetero-aromatic groups having 1 to 5 hetero-atoms, wherein at least one hetero-atom is selected from the group consisting of a nitrogen atom, an oxygen atom, a sulfur atom, a selenium atom, a silicon atom, a phosphorus atom, a germanium atom, and a boron atom. A hetero-aromatic group is also referred to as heteroaryl. Heteroaryl may be those having 3 to 30 carbon atoms, preferably those having 3 to 20 carbon atoms, and more preferably those having 3 to 12 carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridoindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indenoazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—as used herein, is represented by —O-alkyl, —O-cycloalkyl, —O-heteroalkyl, or —O-heterocyclic group. Examples and preferred examples of alkyl, cycloalkyl, heteroalkyl, and heterocyclic groups are the same as those described above. Alkoxy groups may be those having 1 to 20 carbon atoms, preferably those having 1 to 6 carbon atoms. Examples of alkoxy groups include methoxy, ethoxy, propoxy, butoxy, pentyloxy, hexyloxy, cyclopropyloxy, cyclobutyloxy, cyclopentyloxy, cyclohexyloxy, tetrahydrofuranyloxy, tetrahydropyranyloxy, methoxypropyloxy, ethoxyethyloxy, methoxymethyloxy, and ethoxymethyloxy. Additionally, the alkoxy group may be optionally substituted.

Aryloxy—as used herein, is represented by —O-aryl or —O-heteroaryl. Examples and preferred examples of aryl and heteroaryl are the same as those described above. Aryloxy groups may be those having 6 to 30 carbon atoms, preferably those having 6 to 20 carbon atoms. Examples of aryloxy groups include phenoxy and biphenyloxy. Additionally, the aryloxy group may be optionally substituted.

Arylalkyl—as used herein, contemplates alkyl substituted with an aryl group. Arylalkyl may be those having 7 to 30 carbon atoms, preferably those having 7 to 20 carbon atoms, and more preferably those having 7 to 13 carbon atoms. Examples of arylalkyl groups include benzyl, 1-phenylethyl, 2-phenylethyl, 1-phenylisopropyl, 2-phenylisopropyl, phenyl-t-butyl, alpha-naphthylmethyl, 1-alpha-naphthylethyl, 2-alpha-naphthylethyl, 1-alpha-naphthylisopropyl, 2-alpha-naphthylisopropyl, beta-naphthylmethyl, 1-beta-naphthylethyl, 2-beta-naphthylethyl, 1-beta-naphthylisopropyl, 2-beta-naphthylisopropyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, and 1-chloro-2-phenylisopropyl. Of the above, preferred are benzyl, p-cyanobenzyl, m-cyanobenzyl, o-cyanobenzyl, 1-phenylethyl, 2-phenylethyl, 1-phenylisopropyl, and 2-phenylisopropyl. Additionally, the arylalkyl group may be optionally substituted.

Alkylsilyl—as used herein, contemplates a silyl group substituted with an alkyl group. Alkylsilyl groups may be those having 3 to 20 carbon atoms, preferably those having 3 to 10 carbon atoms. Examples of alkylsilyl groups include trimethylsilyl, triethylsilyl, methyldiethylsilyl, ethyldimethylsilyl, tripropylsilyl, tributylsilyl, triisopropylsilyl, methyldiisopropylsilyl, dimethylisopropylsilyl, tri-t-butylsilyl, triisobutylsilyl, dimethyl t-butylsilyl, and methyl di-t-butylsilyl. Additionally, the alkylsilyl group may be optionally substituted.

Arylsilyl—as used herein, contemplates a silyl group substituted with at least one aryl group. Arylsilyl groups may be those having 6 to 30 carbon atoms, preferably those having 8 to 20 carbon atoms. Examples of arylsilyl groups include triphenylsilyl, phenyldibiphenylylsilyl, diphenylbiphenylsilyl, phenyldiethylsilyl, diphenylethylsilyl, phenyldimethylsilyl, diphenylmethylsilyl, phenyldiisopropylsilyl, diphenylisopropylsilyl, diphenylbutylsilyl, diphenylisobutylsilyl, diphenyl t-butylsilyl. Additionally, the arylsilyl group may be optionally substituted.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline, dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

In the present disclosure, unless otherwise defined, when any term of the group consisting of substituted alkyl, substituted cycloalkyl, substituted heteroalkyl, a substituted heterocyclic group, substituted arylalkyl, substituted alkoxy, substituted aryloxy, substituted alkenyl, substituted alkynyl, substituted aryl, substituted heteroaryl, substituted alkylsilyl, substituted arylsilyl, substituted amino, substituted acyl, substituted carbonyl, a substituted carboxylic acid group, a substituted ester group, substituted sulfinyl, substituted sulfonyl and substituted phosphino is used, it means that any group of alkyl, cycloalkyl, heteroalkyl, heterocyclic group, arylalkyl, alkoxy, aryloxy, alkenyl, alkynyl, aryl, heteroaryl, alkylsilyl, arylsilyl, amino, acyl, carbonyl, carboxylic acid group, ester group, sulfinyl, sulfonyl and phosphino may be substituted with one or more groups selected from the group consisting of deuterium, halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted heterocyclic group having 3 to 20 ring atoms, an unsubstituted arylalkyl group having 7 to 30 carbon atoms, an unsubstituted alkoxy group having 1 to 20 carbon atoms, an unsubstituted aryloxy group having 6 to 30 carbon atoms, an unsubstituted alkenyl group having 2 to 20 carbon atoms, an unsubstituted alkynyl group having 2 to 20 carbon atoms, an unsubstituted aryl group having 6 to 30 carbon atoms, an unsubstituted heteroaryl group having 3 to 30 carbon atoms, an unsubstituted alkylsilyl group having 3 to 20 carbon atoms, an unsubstituted arylsilyl group having 6 to 20 carbon atoms, an unsubstituted amino group having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in the present disclosure, the hydrogen atoms can be partially or fully replaced by deuterium. Other atoms such as carbon and nitrogen can also be replaced by their other stable isotopes. The replacement by other stable isotopes in the compounds may be preferred due to its enhancements of device efficiency and stability.

In the compounds mentioned in the present disclosure, multiple substitutions refer to a range that includes a double substitution, up to the maximum available substitutions. When a substitution in the compounds mentioned in the present disclosure represents multiple substitutions (including di, tri, tetra substitutions etc.), that means the substituent may exist at a plurality of available substitution positions on its linking structure, the substituents present at a plurality of available substitution positions may be the same structure or different structures.

In the compounds mentioned in the present disclosure, adjacent substituents in the compounds cannot connect to form a ring unless otherwise explicitly defined, for example, adjacent substituents can be optionally joined to form a ring. In the compounds mentioned in the present disclosure, adjacent substituents can be optionally joined to form a ring, including both the case where adjacent substituents can be joined to form a ring, and the case where adjacent substituents are not joined to form a ring. When adjacent substituents can be optionally joined to form a ring, the ring formed may be monocyclic or polycyclic, as well as alicyclic, heteroalicyclic, aromatic or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

The expression that adjacent substituents can be optionally joined to form a ring is also intended to mean that two substituents bonded to the same carbon atom are joined to each other via a chemical bond to form a ring, which can be exemplified by the following formula:

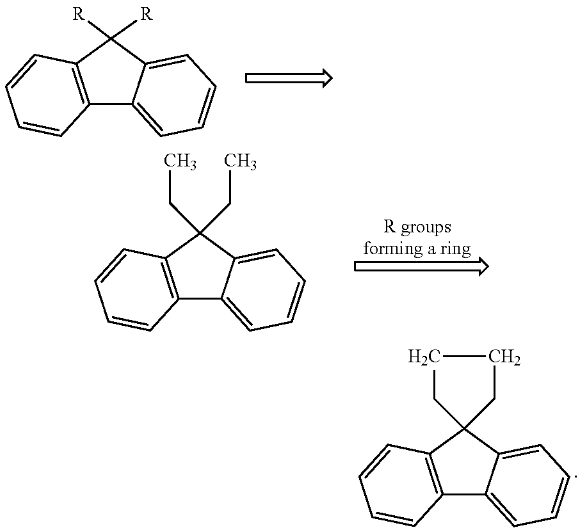

The expression that adjacent substituents can be optionally joined to form a ring is also intended to mean that two substituents bonded to carbon atoms which are directly bonded to each other are joined to each other via a chemical bond to form a ring, which can be exemplified by the following formula:

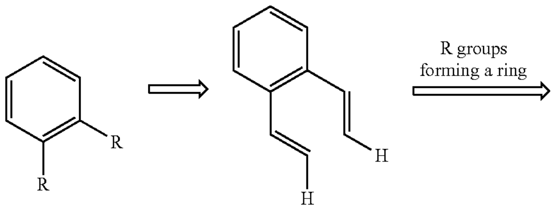

-continued

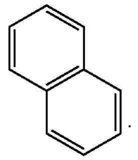

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

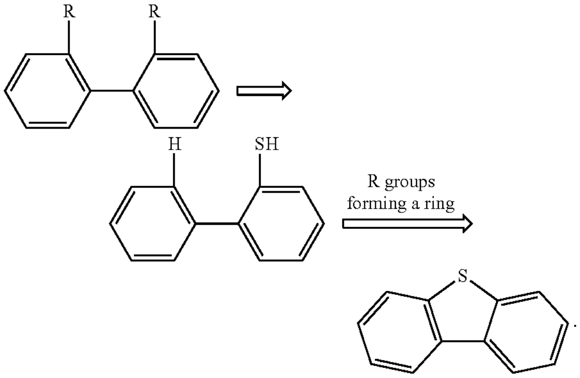

According to an embodiment of the present disclosure, disclosed is an electroluminescent device, comprising:

an anode, a cathode, and an organic layer disposed between the anode and the cathode, wherein the organic layer comprises at least a first compound and a second compound, and the first compound and the second compound are different;

the first compound has a structure of $H_1$-$L_1$-$Ar_1$; wherein the $H_1$ has a structure represented by Formula 1:

Formula 1

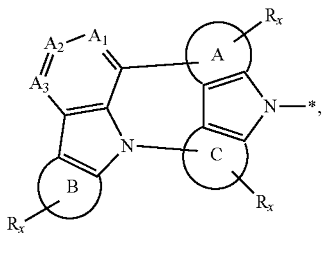

in Formula 1, $A_1$, $A_2$, and $A_3$ are, at each occurrence identically or differently, selected from N or CR, and ring A, ring B, and ring C are, at each occurrence identically or differently, selected from a carbocyclic ring having 5 to 30 carbon atoms or a heterocyclic ring having 3 to 30 carbon atoms;

$R_x$ represents, at each occurrence identically or differently, mono-substitution, multiple substitutions or non-substitution;

adjacent substituents R, $R_x$ can be optionally joined to form a ring;

$L_1$ is selected from a single bond, substituted or unsubstituted arylene having 6 to 30 carbon atoms, substituted or unsubstituted heteroarylene having 3 to 30 carbon atoms, or combinations thereof;

$Ar_1$ is selected from substituted or unsubstituted aryl having 6 to 30 carbon atoms or substituted or unsubstituted heteroaryl having 3 to 30 carbon atoms;

the second compound has a structure of $H_2$-$L_2$-$Ar_2$;

wherein the $H_2$ has a structure represented by Formula 2:

Formula 2

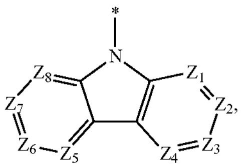

in Formula 2, $Z_1$ to $Z_3$ and $Z_6$ to $Z_8$ are, at each occurrence identically or differently, selected from $CR_{z1}$ or N, $Z_4$ and $Z_5$ are, at each occurrence identically or differently, selected from $CR_{z2}$, and two substituents $R_{z2}$ in $Z_4$ and $Z_5$ are joined to form a ring;

$Ar_2$ is selected from substituted or unsubstituted aryl having 6 to 30 carbon atoms or substituted or unsubstituted heteroaryl having 3 to 30 carbon atoms;

$L_2$ is selected from a single bond, substituted or unsubstituted arylene having 6 to 30 carbon atoms, substituted or unsubstituted heteroarylene having 3 to 30 carbon atoms, or combinations thereof;

R, $R_x$, and $R_{z1}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

$R_{z2}$ is, at each occurrence identically or differently, selected from the group consisting of: hydrogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a hydroxyl group, a sulfanyl group, a sulfinyl group, a sulfonyl group, a phosphino group, and combinations thereof;

adjacent substituents $R_{z1}$, $R_{z2}$ can be optionally joined to form a ring.

In this embodiment, the expression that adjacent substituents R, $R_x$ can be optionally joined to form a ring is intended to mean that any one or more of groups of adjacent substituents, such as substituents R, substituents $R_x$, and substituents R and $R_x$, can be joined to form a ring. Obviously, it is possible that none of these groups of adjacent substituents are joined to form a ring.

In this embodiment, the expression that adjacent substituents $R_{z1}$, $R_{z2}$ can be optionally joined to form a ring is intended to mean that any one or more of groups of adjacent substituents in Formula 2, such as adjacent substituents $R_{z1}$ in $Z_1$ to $Z_3$, adjacent substituents $R_{z1}$ in $Z_6$ to $Z_8$, substituent $R_{z1}$ in $Z_3$ and substituent $R_{z2}$ in $Z_4$, substituent $R_{z1}$ in $Z_3$ and substituent $R_{z2}$ in $Z_8$, substituent $R_{z1}$ in $Z_6$ and substituent $R_{z2}$ in $Z_4$, and substituent $R_{z1}$ in $Z_6$ and substituent $R_{z2}$ in $Z_5$, can be joined to form a ring. Obviously, it is possible that none of these groups of adjacent substituents are joined to form a ring.

According to an embodiment of the present disclosure, wherein, in Formula 1, the ring A, the ring B, and the ring C are, at each occurrence identically or differently, selected from a 5-membered carbocyclic ring, an aromatic ring having 6 to 18 carbon atoms or a heteroaromatic ring having 3 to 18 carbon atoms.

According to an embodiment of the present invention, wherein, in Formula 1, the ring A, the ring B, and the ring C are, at each occurrence identically or differently, selected from a 5-membered carbocyclic ring, a benzene ring, a 5-membered heteroaromatic ring or a 6-membered heteroaromatic ring.

According to an embodiment of the present disclosure, wherein, in the first compound, the $H_1$ has a structure represented by Formula 1-a:

Formula 1-a

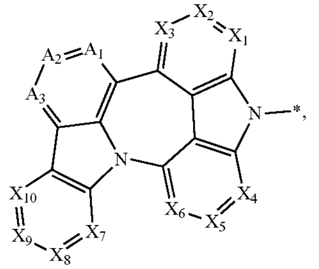

wherein $A_1$ to $A_3$ are, at each occurrence identically or differently, selected from N or CR, and $X_1$ to $X_{10}$ are, at each occurrence identically or differently, selected from N or $CR_x$;

R and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents R and $R_x$ can be optionally joined to form a ring.

In this embodiment, the expression that adjacent substituents R, $R_x$ can be optionally joined to form a ring is intended to mean that adjacent substituents R can be optionally joined to form a ring, is also intended to mean that adjacent substituents $R_x$ in $X_1$ to $X_3$ can be optionally joined to form a ring, is also intended to mean that that adjacent substituents $R_x$ in $X_4$ to $X_6$ can be optionally joined to form a ring, is also intended to mean that that adjacent substituents $R_x$ in $X_7$ to $X_{10}$ can be optionally joined to form a ring, and is also intended to mean that that adjacent substituents R and $R_x$ can be optionally joined to form a ring, for example, adjacent substituents in $A_1$ and $X_3$, and/or adjacent substituents in $A_3$ and $X_{10}$, and/or adjacent substituents in $X_6$ and $X_7$ can be optionally joined to form a ring. Obviously, for those skilled in the art, it may be that adjacent substituents R, $R_x$ are not joined to form a ring, and in this case, adjacent substituents R are not joined to form a ring, and/or adjacent substituents $R_x$ are not joined to form a ring, and/or adjacent substituents R and $R_x$ are not joined to form a ring.

According to an embodiment of the present disclosure, wherein, in Formula 1-a, R and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, an isocyano group, a hydroxyl group, a sulfanyl group, and combinations thereof;

adjacent substituents R, $R_x$ can be optionally joined to form a ring.

According to an embodiment of the present disclosure, wherein, in Formula 1 or Formula 1-a, at least one of R and $R_x$ is selected from deuterium, substituted or unsubstituted aryl having 6 to 30 carbon atoms or substituted or unsubstituted heteroaryl having 3 to 30 carbon atoms.

According to an embodiment of the present disclosure, wherein, in Formula 1 or Formula 1-a, at least one of R and $R_x$ is selected from deuterium, phenyl, biphenyl or pyridyl.

According to an embodiment of the present disclosure, wherein, in Formula 1-a, at least one of groups of adjacent substituents: adjacent substituents R in $A_1$ to $A_3$, adjacent substituents $R_x$ in $X_1$ to $X_3$, adjacent substituents $R_x$ in $X_4$ to $X_6$ or adjacent substituents $R_x$ in $X_7$ to $X_{10}$ is joined to form a ring.

In this embodiment, the expression that at least one of groups of adjacent substituents is joined to form a ring is intended to mean that for groups of adjacent substituents in Formula 1-a, such as two adjacent substituents R in $A_1$ and $A_2$, two adjacent substituents R in $A_2$ and $A_3$, two adjacent substituents $R_x$ in $X_1$ and $X_2$, two adjacent substituents $R_x$ in $X_2$ and $X_3$, two adjacent substituents $R_x$ in $X_4$ and $X_5$, two adjacent substituents $R_x$ in $X_5$ and $X_6$, two adjacent substituents $R_x$ in $X_7$ and $X_8$, two adjacent substituents $R_x$ in $X_8$ and $X_9$, and two adjacent substituents $R_x$ in $X_9$ and $X_{10}$, at least one of these groups of substituents is joined to form a ring.

According to an embodiment of the present disclosure, wherein, in the first compound, the $H_1$ is selected from the group consisting of the following structures:

H-1

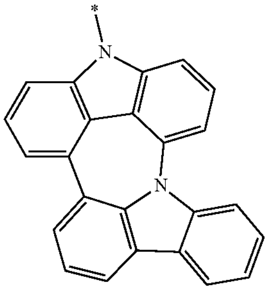

,

H-2

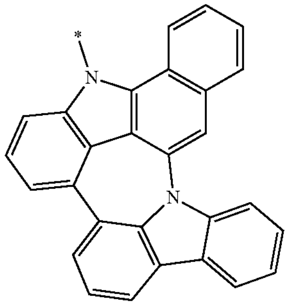

,

H-3

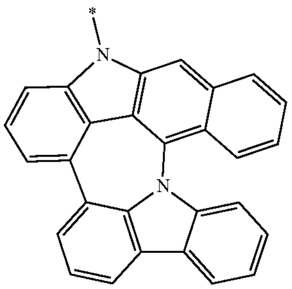

,

-continued

H-4

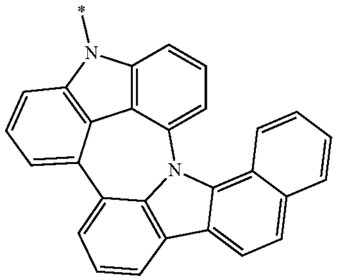

,

H-5

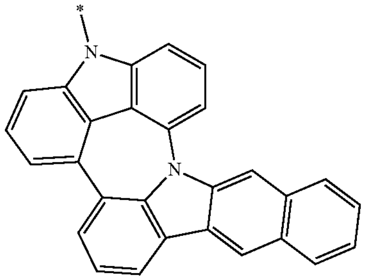

,

H-6

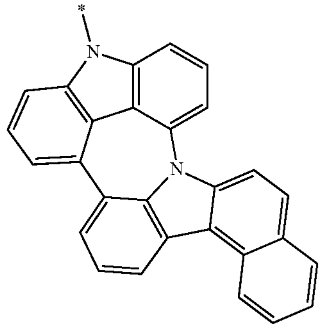

,

H-7

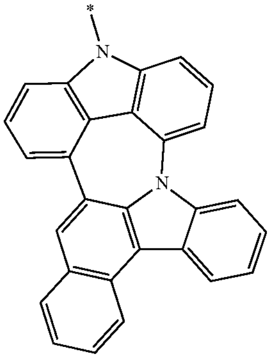

,

H-8

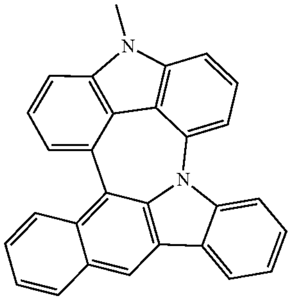

,

-continued
H-9
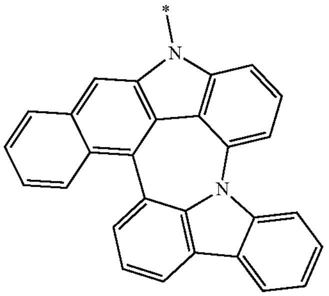
,
H-10
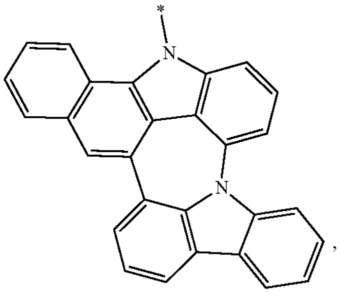
,
H-11
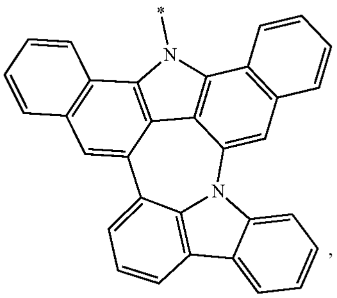
,
H-12
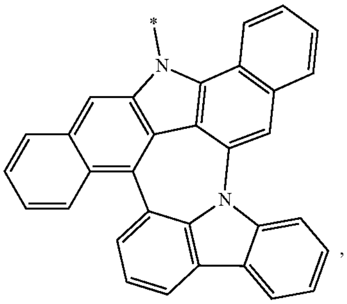
,
H-13
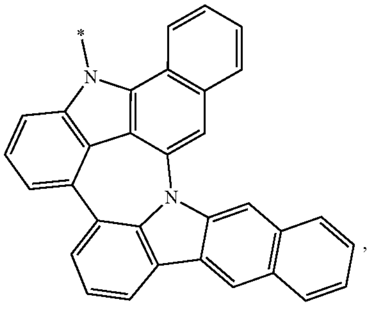
,
-continued
H-14
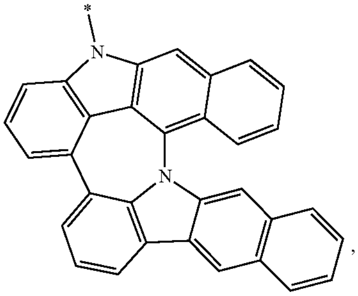
,
H-15
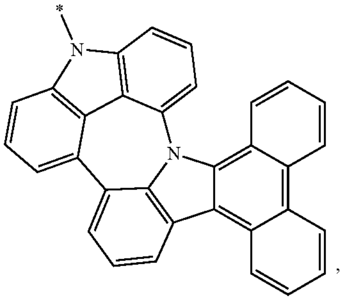
,
H-16
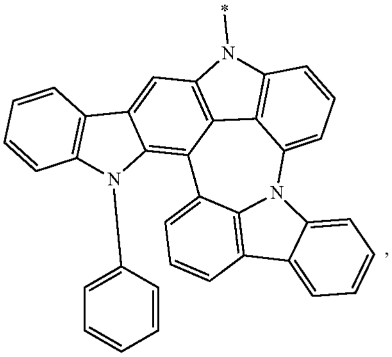
,
H-17
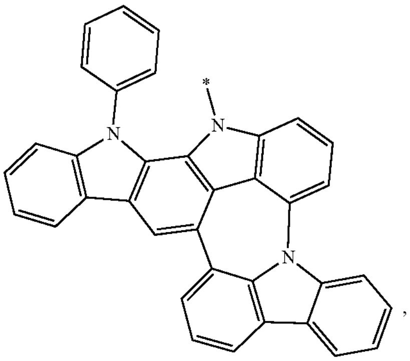
,
H-18
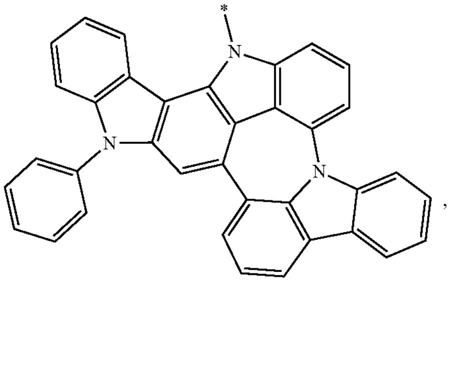
, -continued
H-19
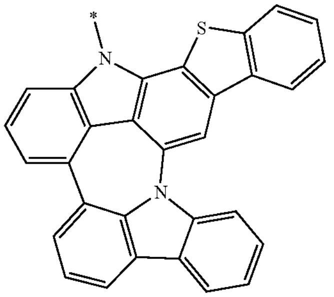
,
H-20
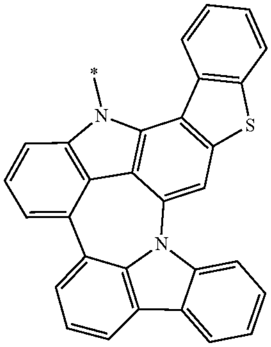
,
H-21
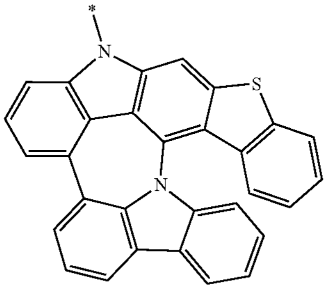
,
H-22
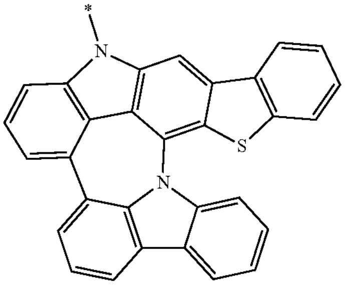
,
H-23
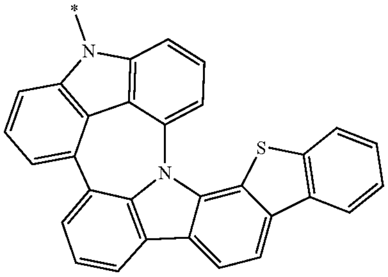
,
-continued
H-24
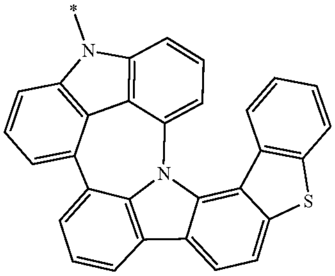
,
H-25
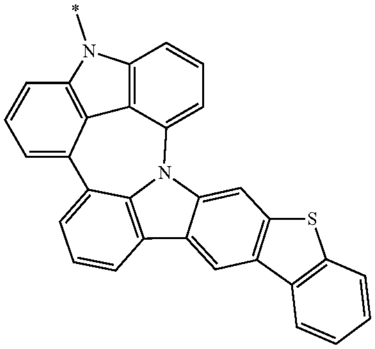
,
H-26
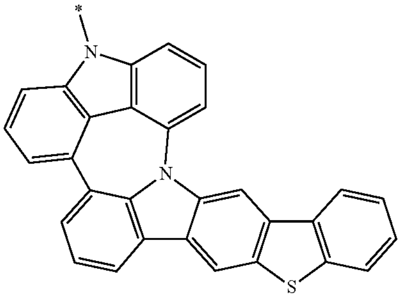
,
H-27
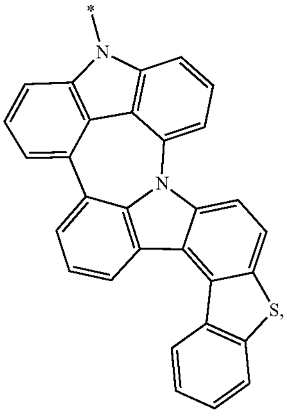
, -continued
H-28
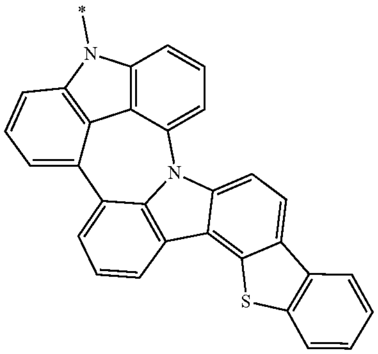
,
H-29
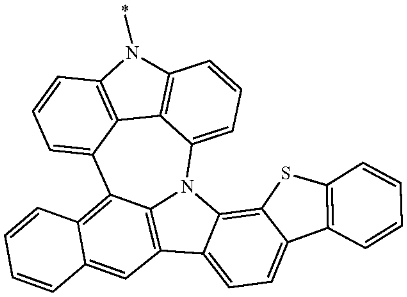
,
H-30
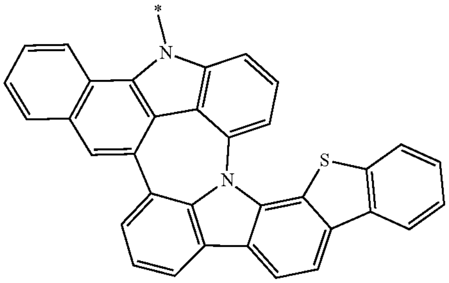
,
H-31
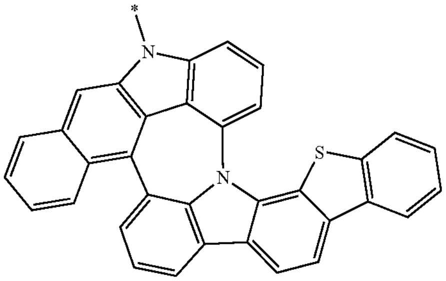
,
H-32
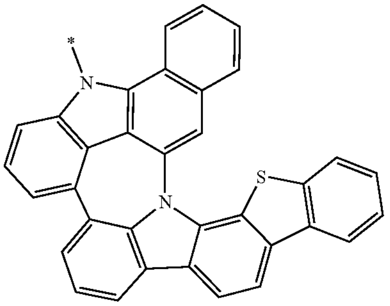
,
-continued
H-33
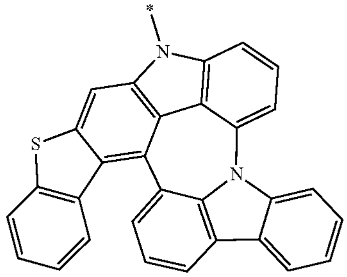
,
H-34
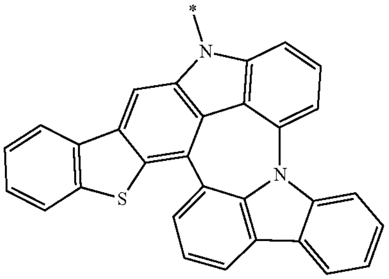
,
H-35
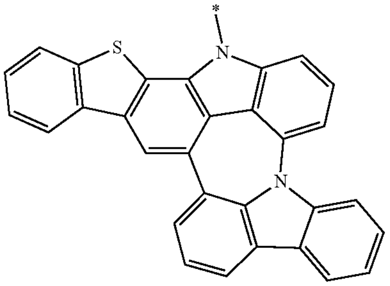
,
H-36
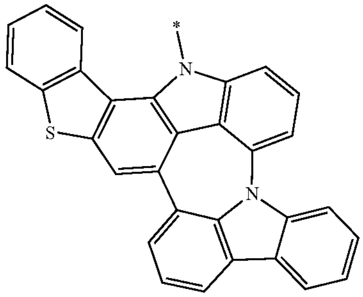
,
H-37
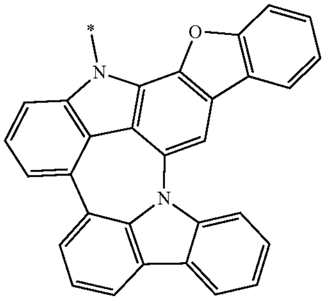
, -continued
H-38
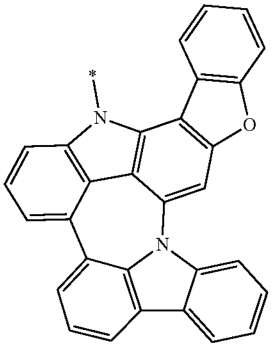
,
H-39
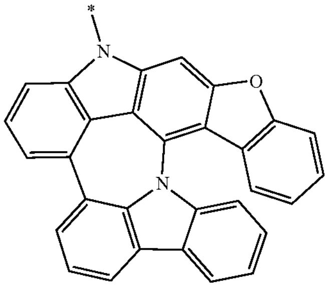
,
H-40
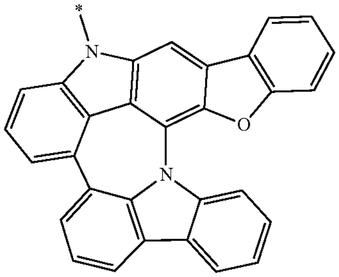
,
H-41
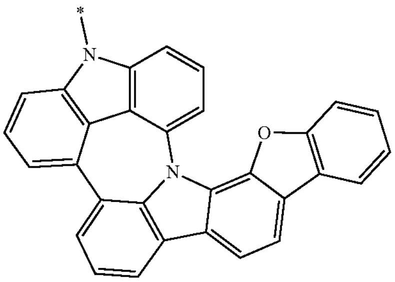
,
H-42
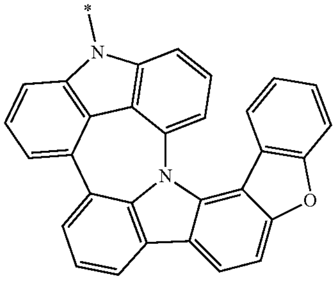
,
-continued
H-43
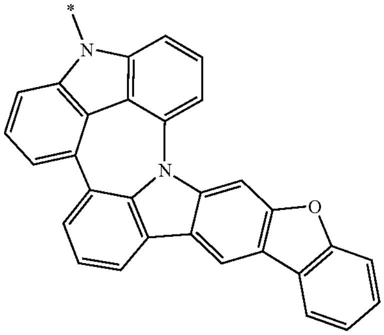
,
H-44
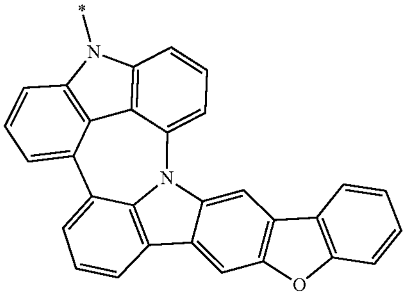
,
H-45
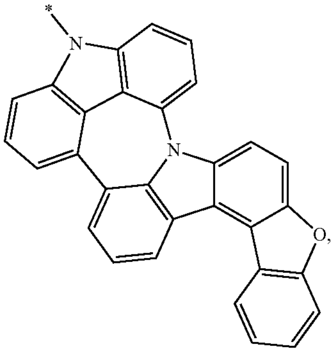
H-46
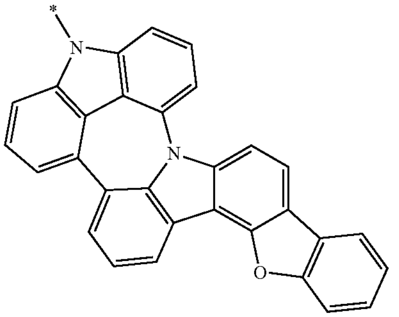
,
H-47
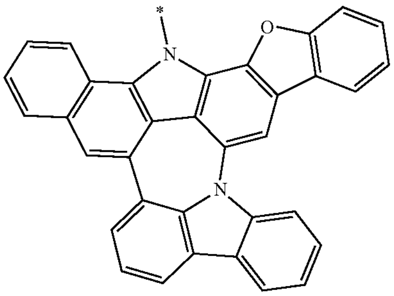
, H-48
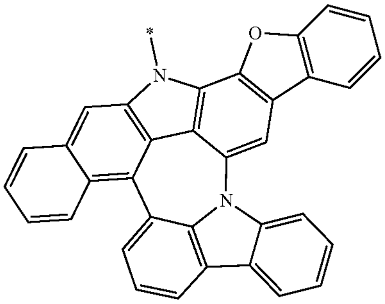
,
H-49
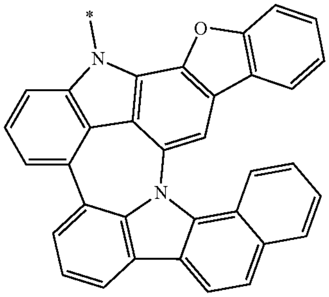
,
H-50
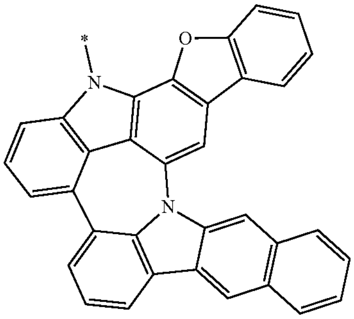
,
H-51
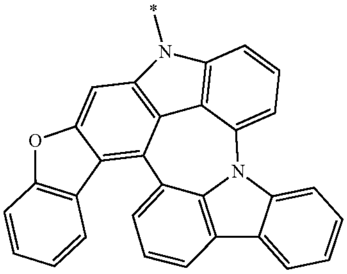
,
H-52
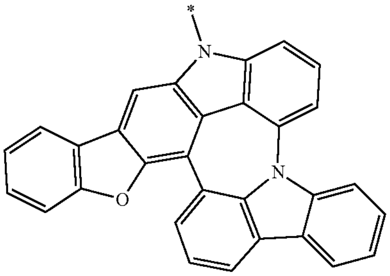
,
H-53
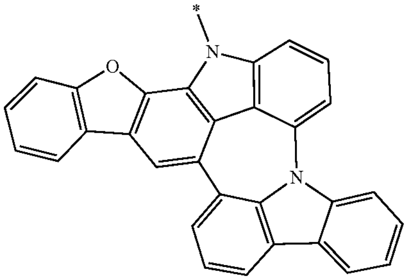
,
H-54
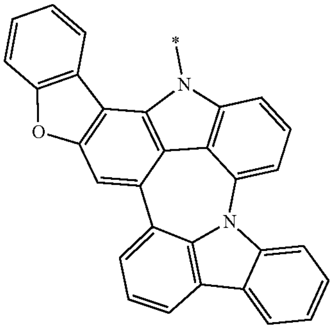
,
H-55
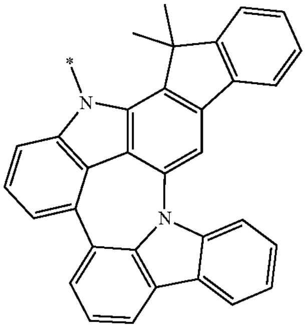
,
H-56
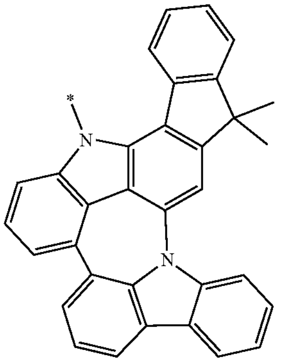
,
H-57
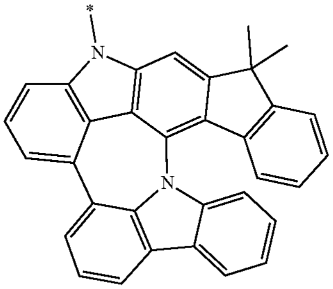
, -continued
H-58
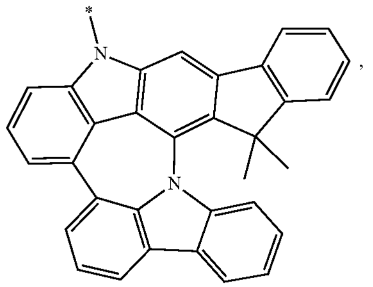
H-59
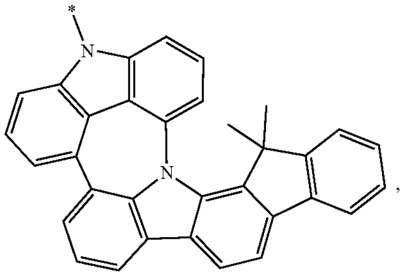
H-60
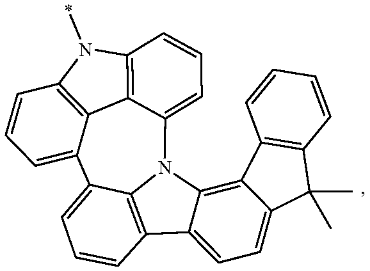
H-61
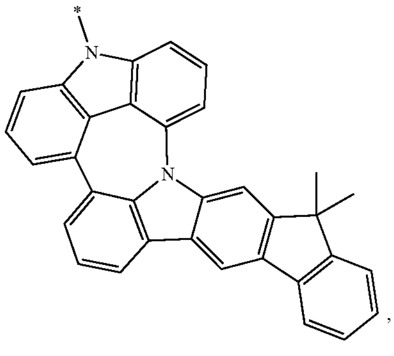
H-62
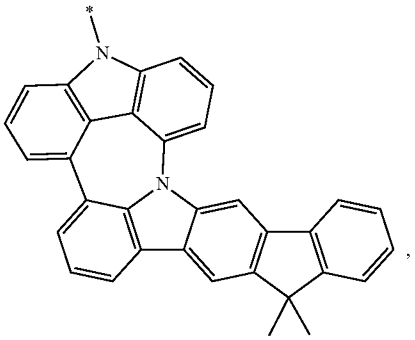
-continued
H-63
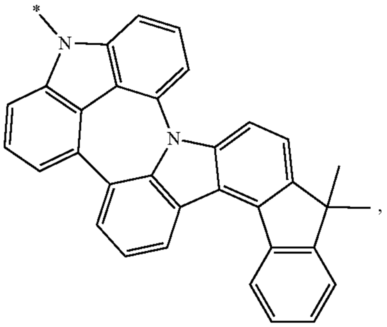
H-64
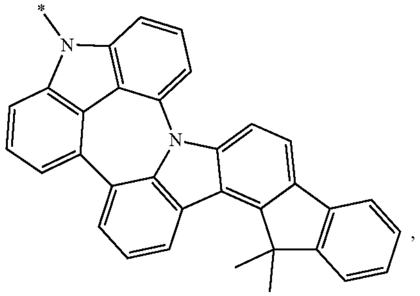
H-65
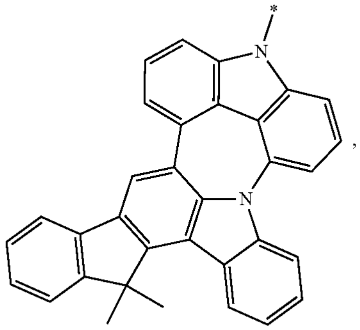
H-66
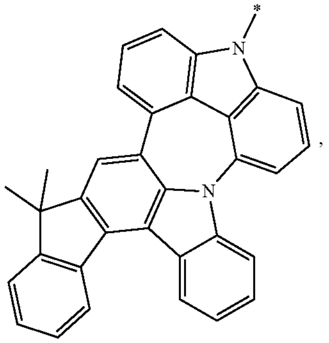
H-67
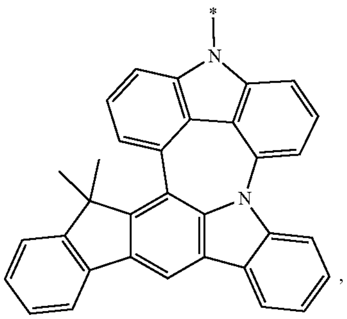

-continued
H-68
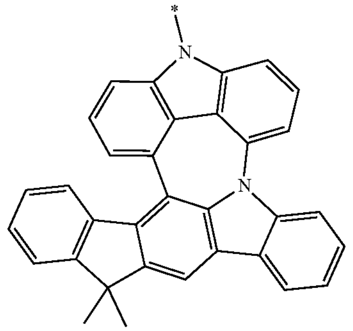
,
H-69
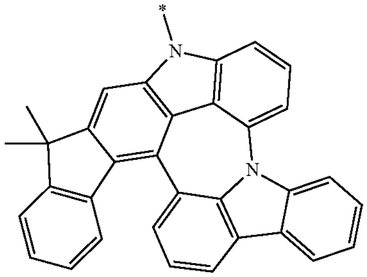
,
H-70
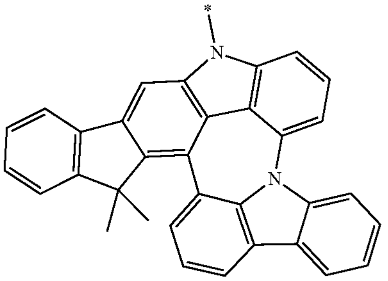
,
H-71
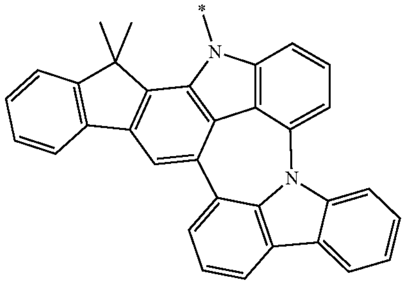
,
H-72
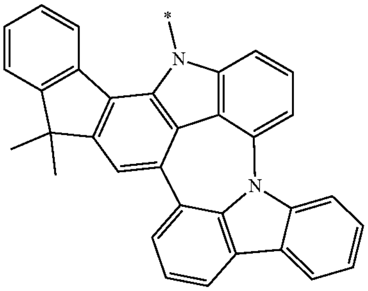
,
-continued
H-73
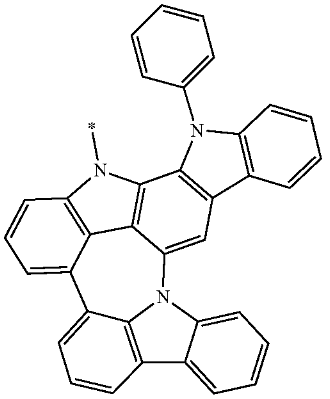
,
H-74
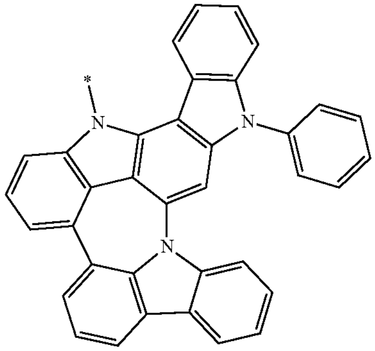
,
H-75
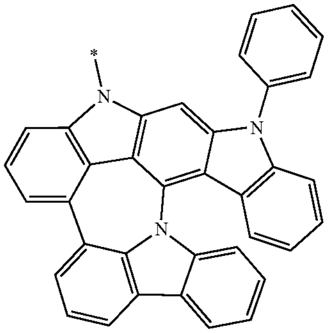
,
H-76
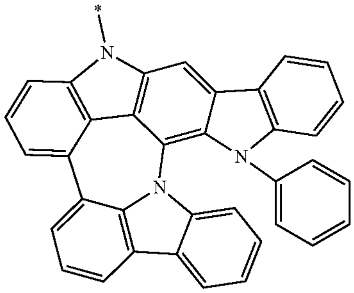
, H-77
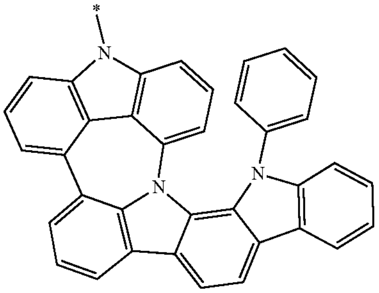
,
H-78
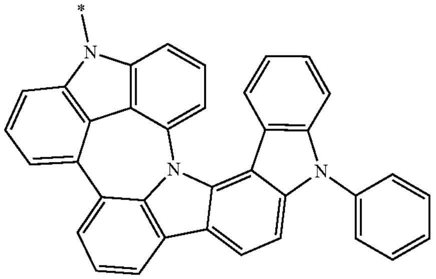
,
H-79
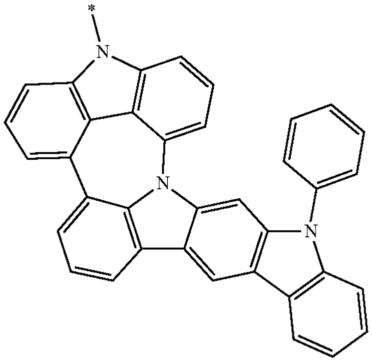
,
H-80
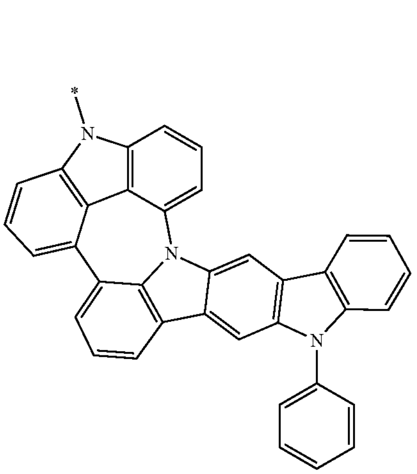
,
H-81
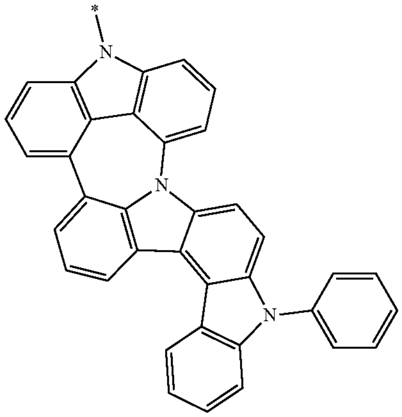
,
H-82
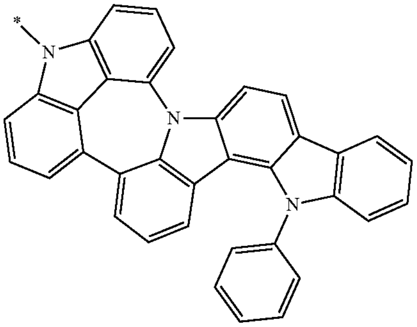
,
H-83
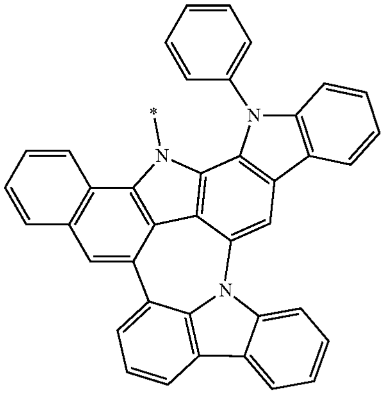
,
H-84
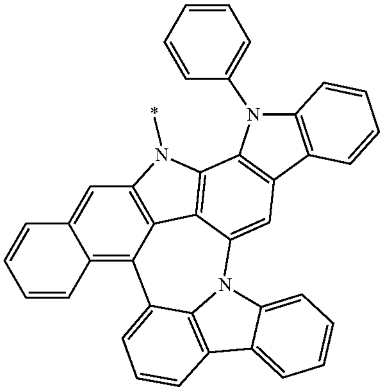

-continued
H-85
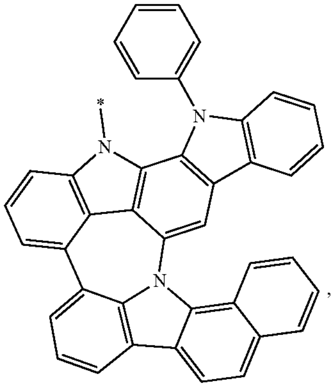
,
H-86
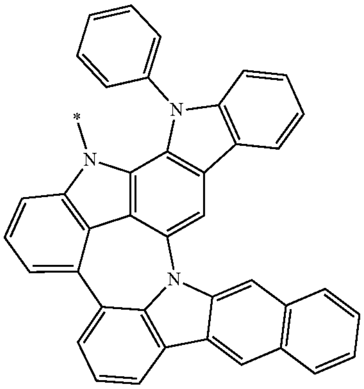
,
H-87
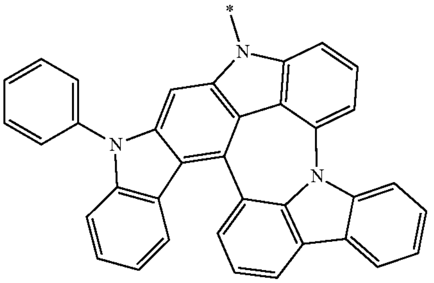
,
H-88
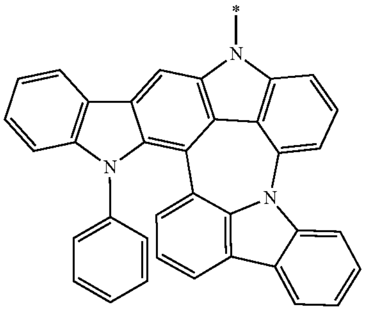
,
-continued
H-89
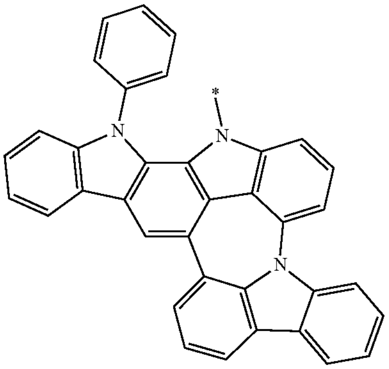
,
H-90
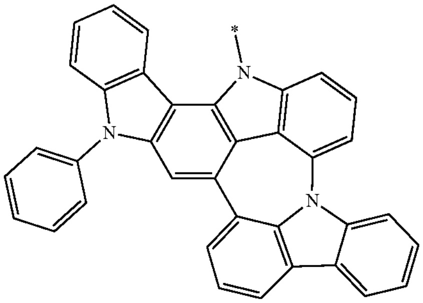
,
H-91
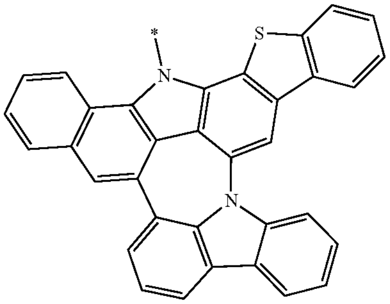
,
H-92
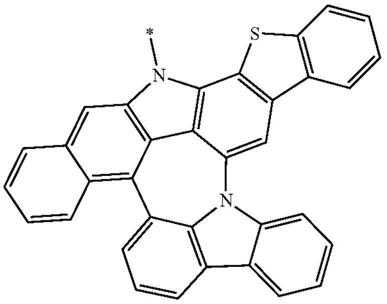
, -continued
H-93
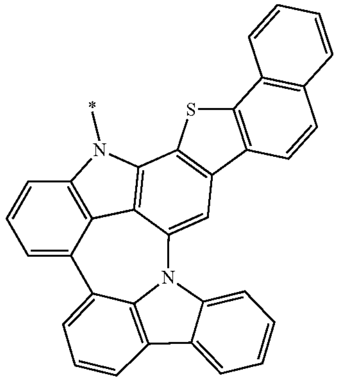
,
H-94
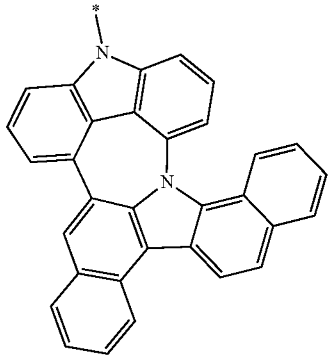
,
H-95
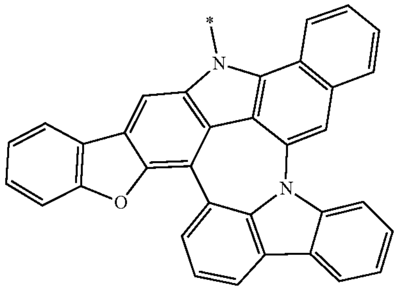
,
H-96
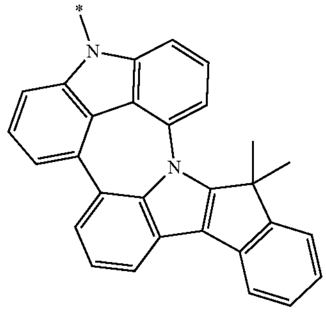
,
-continued
H-97
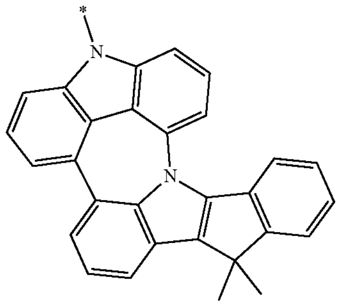
,
H-98
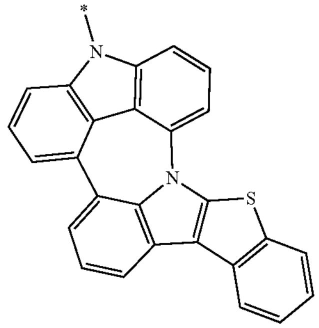
,
H-99
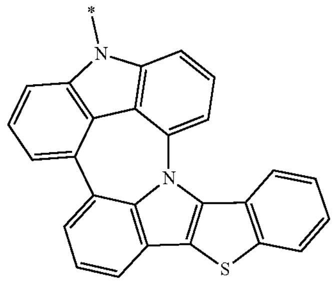
,
H-100
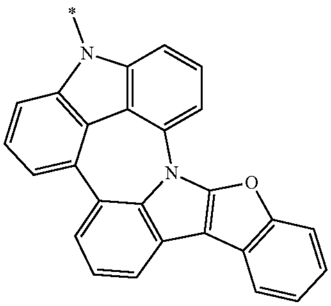
,
H-101
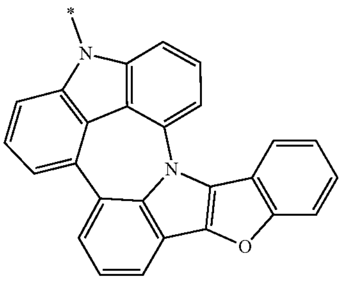
, -continued
H-102
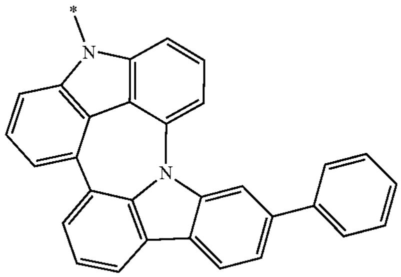
,
H-103
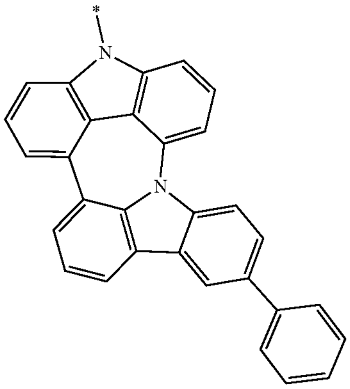
,
H-104
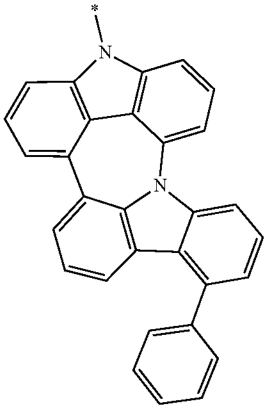
,
H-105
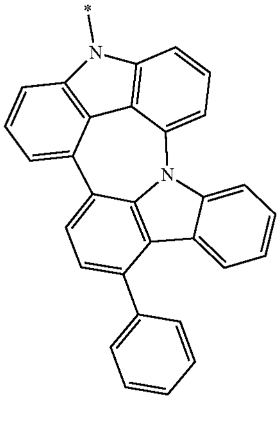
,
-continued
H-106
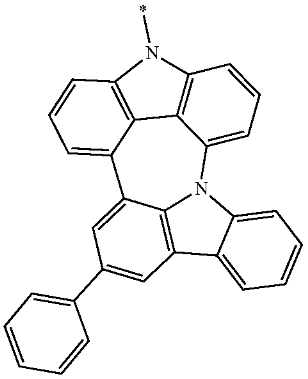
,
H-107
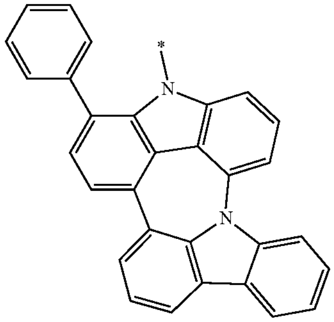
,
H-108
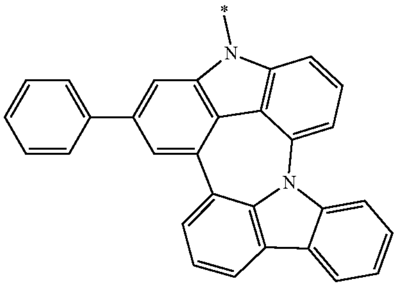
,
H-109
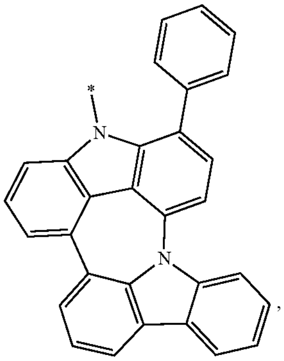
, -continued
H-110
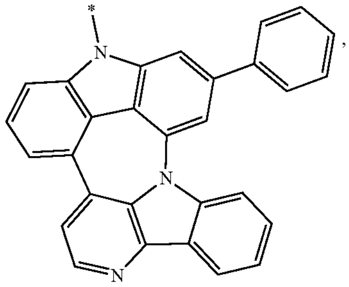
,
H-111
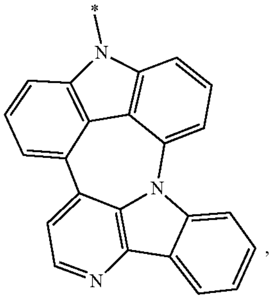
,
H-112
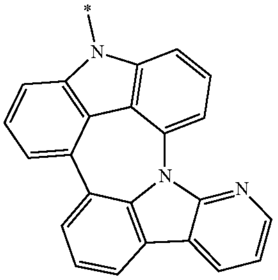
,
H-113
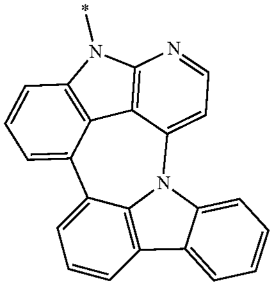
,
H-114
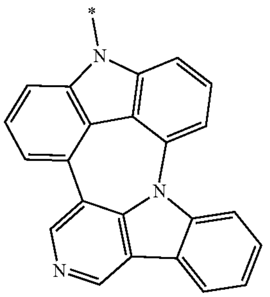
,
-continued
H-115
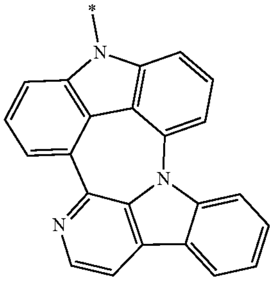
,
H-116
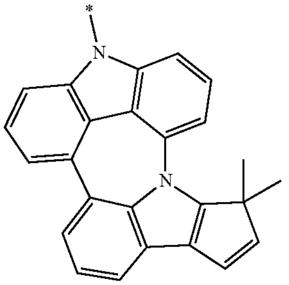
,
H-117
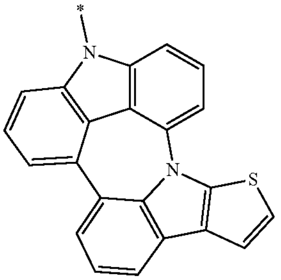
,
H-118
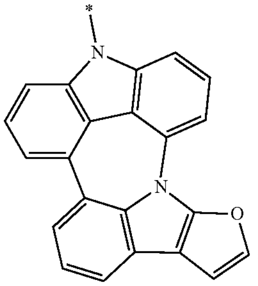
,
H-119
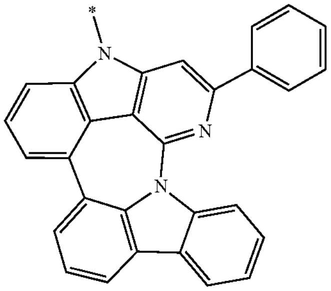
, -continued
H-120
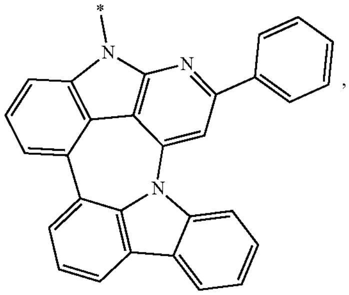
H-121
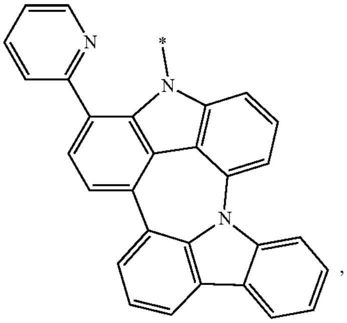
H-122
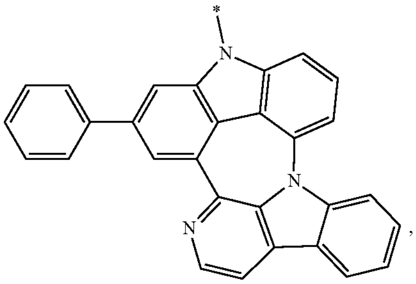
H-123
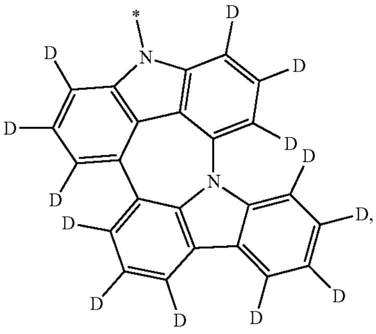
H-124
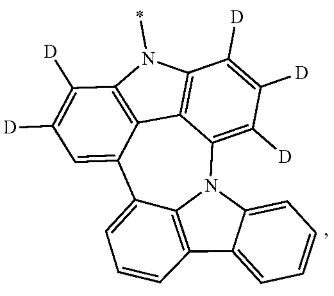
-continued
H-125
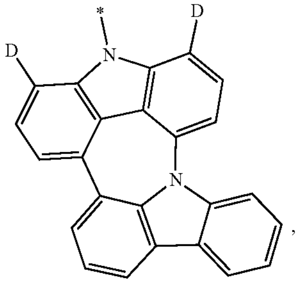
H-126
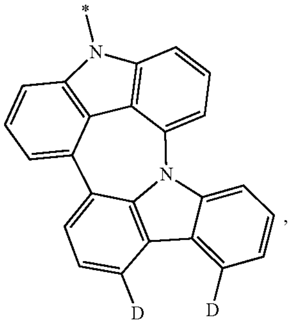
H-127
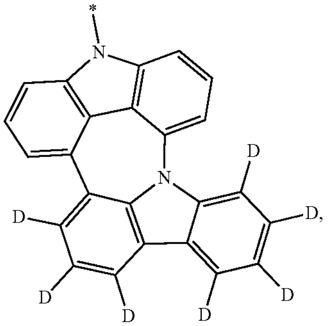
H-128
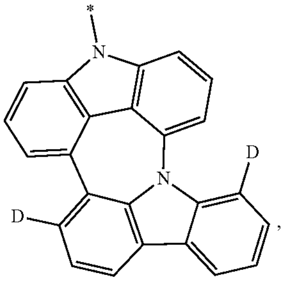
H-129
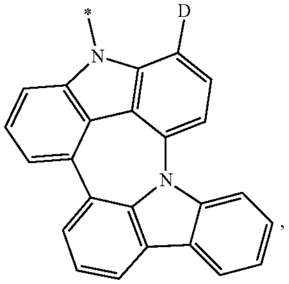

-continued
H-130
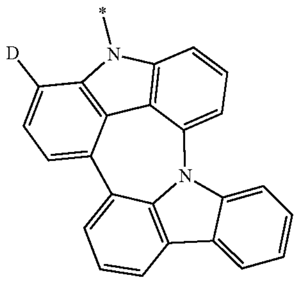
,
H-131
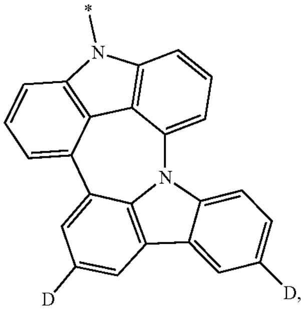
H-132
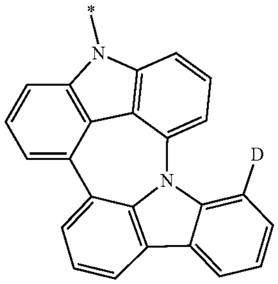
,
H-133
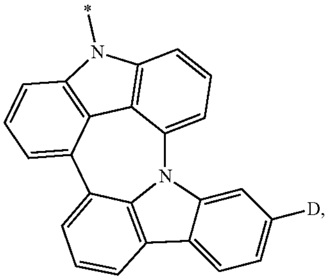
H-134
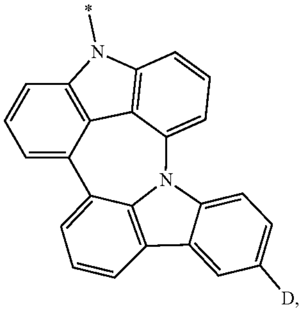
-continued
H-135
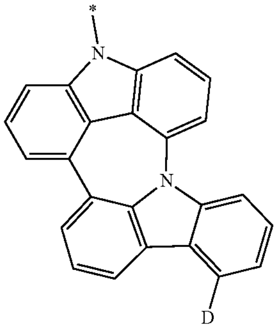
,
H-136
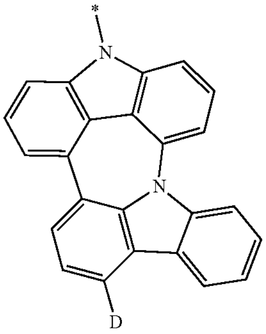
,
H-137
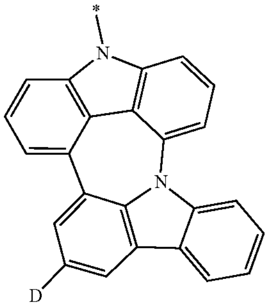
,
H-138
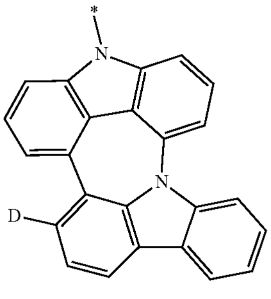
, and
H-139
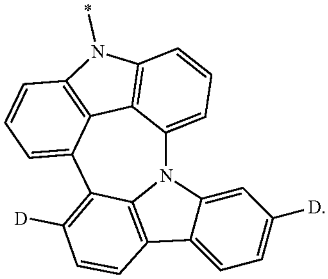
In this embodiment, "*" represents the position at which any of structures H-1 to H-139 is joined to the $L_1$.

According to an embodiment of the present disclosure, wherein, hydrogens in H-1 to H-139 can be partially or completely substituted with deuterium.

According to an embodiment of the present disclosure, wherein, in Formula 2, two substituents $R_{z2}$ in $Z_4$ and $Z_5$ are joined to form a ring, and the ring has at least 6 ring atoms.

According to an embodiment of the present disclosure, wherein, in Formula 2, two substituents $R_{z2}$ in $Z_4$ and $Z_5$ are joined to form a ring, and the ring has at least 7 ring atoms.

According to an embodiment of the present disclosure, wherein, in the second compound, the $H_2$ has a structure represented by any one of Formula 2-1 to Formula 2-8:

Formula 2-1

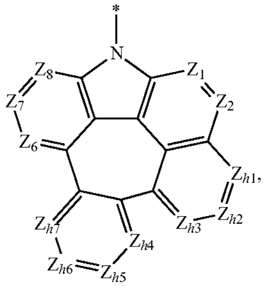

Formula 2-2

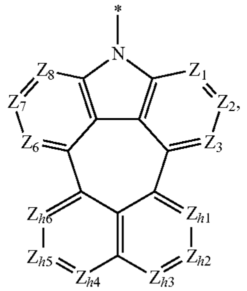

Formula 2-3

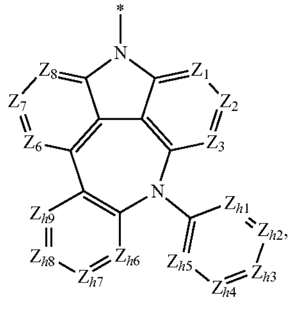

Formula 2-4

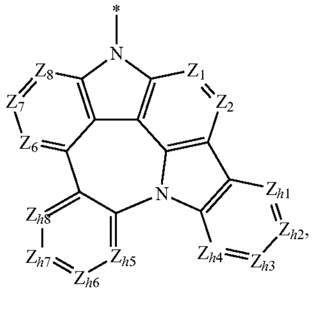

-continued

Formula 2-5

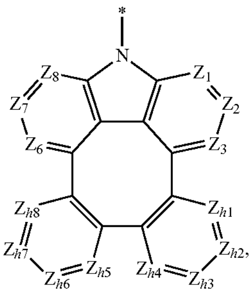

Formula 2-6

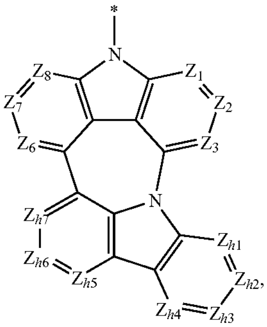

Formula 2-7

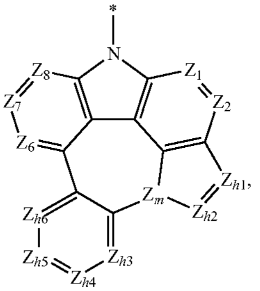

and

Formula 2-8

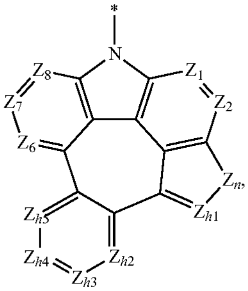

in Formula 2-1 to Formula 2-8, $Z_1$ to $Z_3$ and $Z_6$ to $Z_8$ are, at each occurrence identically or differently, selected from $CR_{z1}$ or N;

$Z_{h1}$ to $Z_{h8}$ are, at each occurrence identically or differently, selected from $CR_{zh}$ or N; $Z_m$ is selected from $CR_{zm}$ or N;

$Z_n$ is selected from $CR_{zn}R_{zn}$, O, S or $NR_{zn}$; when $Z_n$ is selected from $CR_{zn}R_{zn}$, two $R_{zn}$ can be identical or different;

$R_{z1}$, $R_{zh}$, $R_{zm}$, and $R_{zn}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents $R_{z1}$, $R_{zh}$, $R_{zm}$, $R_{zn}$ can be optionally joined to form a ring.

In the present disclosure, the expression that adjacent substituents $R_{z1}$, $R_{zh}$, $R_{zm}$, $R_{zn}$ can be optionally joined to form a ring is intended to mean that any one or more of groups of adjacent substituents, such as adjacent substituents $R_{z1}$ in $Z_1$ to $Z_3$, adjacent substituents $R_{z1}$ in $Z_6$ to $Z_8$, adjacent substituents $R_{zh}$, adjacent substituents $R_{zh}$ and $R_{zm}$, adjacent substituents $R_{zn}$, and adjacent substituents $R_{zh}$ and $R_{zn}$, can be joined to form a ring. Obviously, it is possible that none of these groups of adjacent substituents are joined to form a ring.

According to an embodiment of the present disclosure, wherein, in Formula 2-1 to Formula 2-8, $R_{z1}$, $R_{zh}$, $R_{zm}$, and $R_{zn}$, are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, an isocyano group, a hydroxyl group, a sulfanyl group, and combinations thereof; adjacent substituents $R_{z1}$, $R_{zh}$, $R_{zm}$, $R_{zn}$ can be optionally joined to form a ring.

According to an embodiment of the present disclosure, wherein, in the second compound, the $H_2$ has a structure represented by any one of Formula 2-1 to Formula 2-8:

Formula 2-1

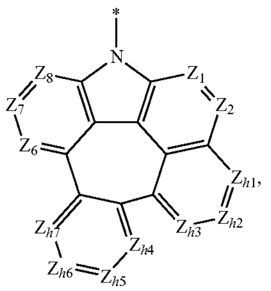

-continued

Formula 2-2

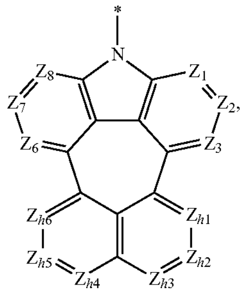

Formula 2-3

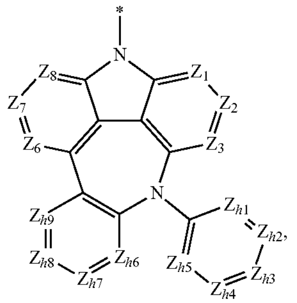

Formula 2-4

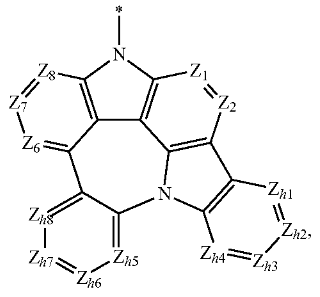

Formula 2-5

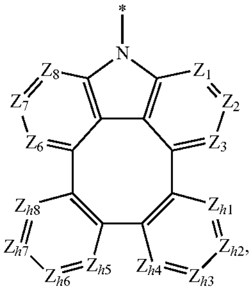

Formula 2-6

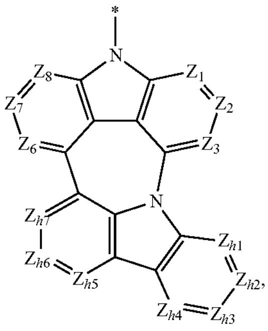

-continued

Formula 2-7

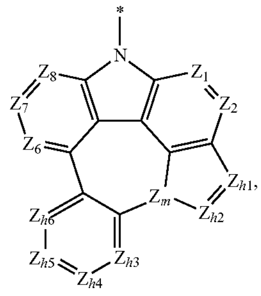

and

Formula 2-8

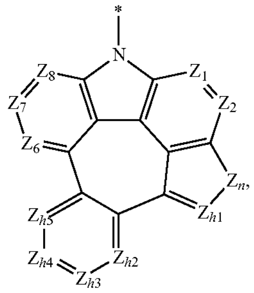

in Formula 2-1 to Formula 2-8, $Z_1$ to $Z_3$ and $Z_6$ to $Z_8$ are, at each occurrence identically or differently, selected from $CR_{z1}$;

$Z_{h1}$ to $Z_{h8}$ are, at each occurrence identically or differently, selected from $CR_{zh}$ or N;

$Z_m$ is selected from N;

$Z_n$ is selected from O, S or $NR_{zn}$;

$R_{z1}$, $R_{zh}$, and $R_{zn}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents $R_{z1}$, $R_{zh}$, $R_{zn}$ can be optionally joined to form a ring.

In the present disclosure, the expression that adjacent substituents $R_{z1}$, $R_{zh}$, $R_{zn}$ can be optionally joined to form a ring is intended to mean that any one or more of groups of adjacent substituents, such as adjacent substituents $R_{z1}$ in $Z_1$ to $Z_3$, adjacent substituents $R_{z1}$ in $Z_6$ to $Z_8$, adjacent substituents $R_{zh}$, adjacent substituents $R_{zn}$, and adjacent substituents $R_{zh}$ and $R_{zn}$, can be joined to form a ring. Obviously, it is possible that none of these groups of adjacent substituents are joined to form a ring.

According to an embodiment of the present disclosure, wherein, in the second compound, the $H_2$ has a structure represented by any one of Formula 2-1 to Formula 2-8:

Formula 2-1

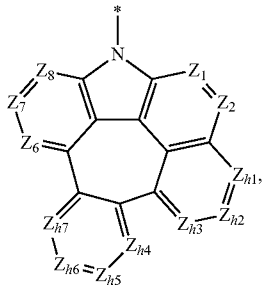

Formula 2-2

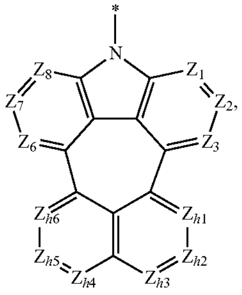

Formula 2-3

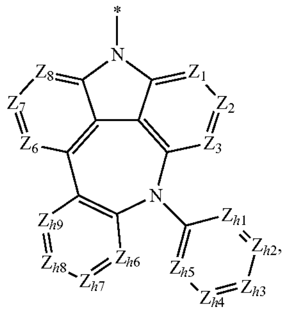

Formula 2-4

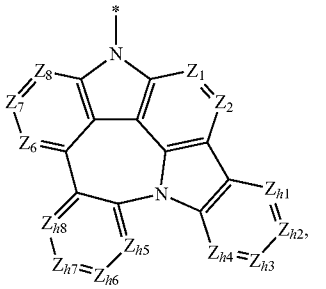

Formula 2-5

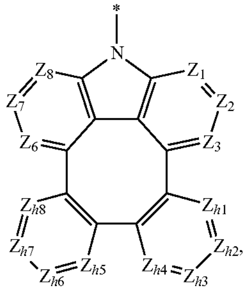

-continued

Formula 2-6

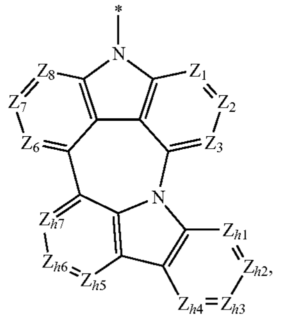

Formula 2-7

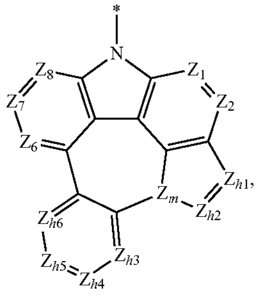

and

Formula 2-8

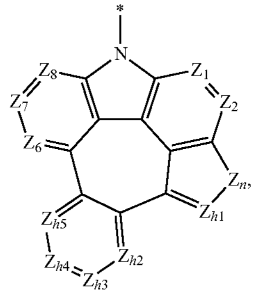

in Formula 2-1 to Formula 2-8, $Z_1$ to $Z_3$ and $Z_6$ to $Z_8$ are, at each occurrence identically or differently, selected from $CR_{z1}$;

$Z_{h1}$ to $Z_{h8}$ are, at each occurrence identically or differently, selected from $CR_{zh}$ or N;

$Z_m$ is selected from N;

$Z_n$ is selected from O, S or $NR_{zn}$;

$R_{z1}$, $R_{zh}$, and $R_{zn}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, an isocyano group, a hydroxyl group, a sulfanyl group, and combinations thereof;

adjacent substituents $R_{z1}$, $R_{zh}$, $R_{zn}$ can be optionally joined to form a ring.

According to an embodiment of the present disclosure, wherein, the $H_2$ is selected from the group consisting of H-1 to H-139 and the following structures:

H2-1

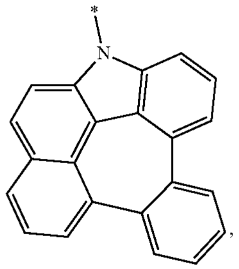

H2-2

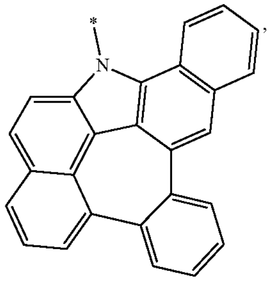

H2-3

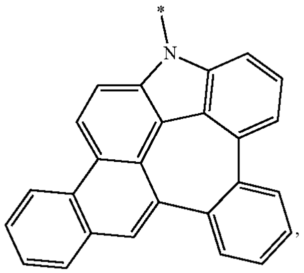

H2-4

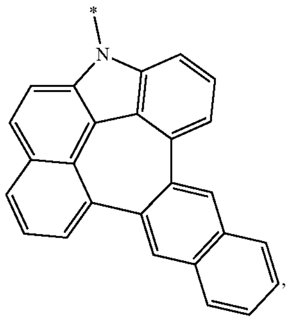

H2-5

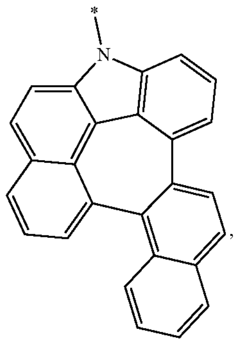

-continued
H2-6
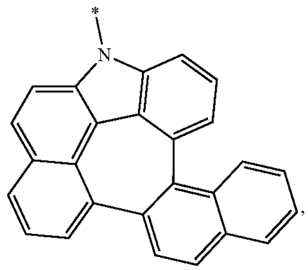
,
H2-7
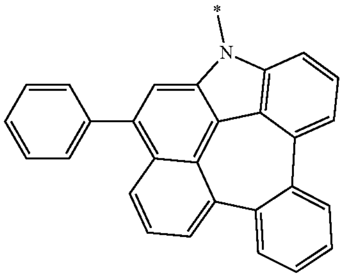
,
H2-8
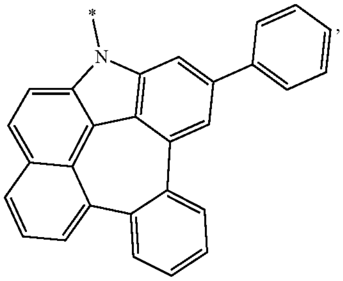
,
H2-9
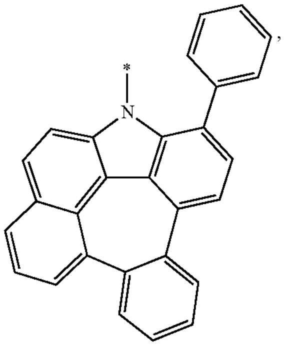
,
H2-10
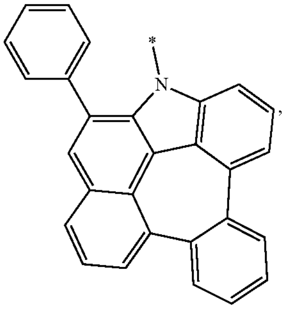
,
-continued
H2-11
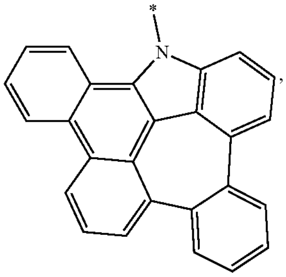
,
H2-12
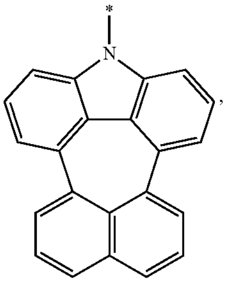
,
H2-13
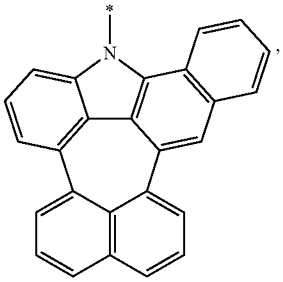
,
H2-14
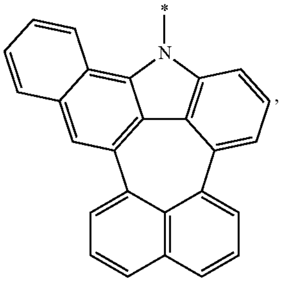
,
H2-15
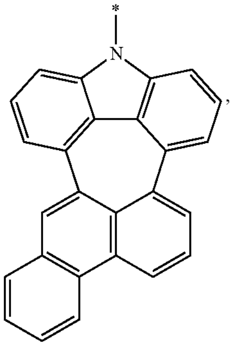
, -continued
H2-16
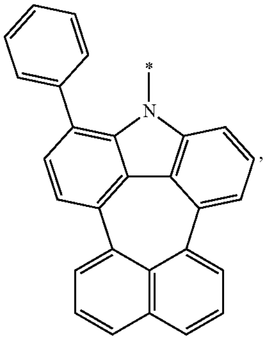
,
H2-17
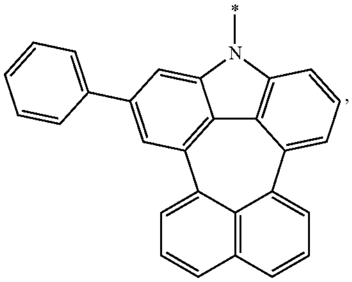
,
H2-18
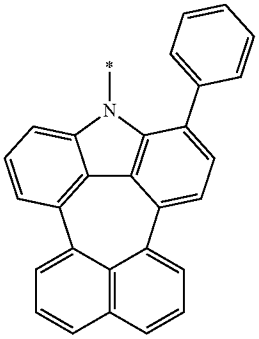
,
H2-19
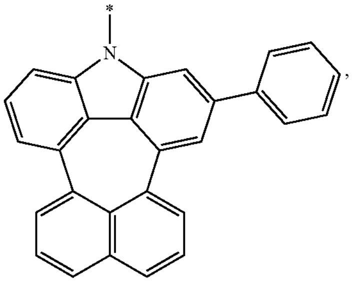
,
H2-20
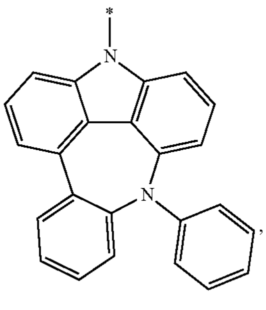
,
-continued
H2-21
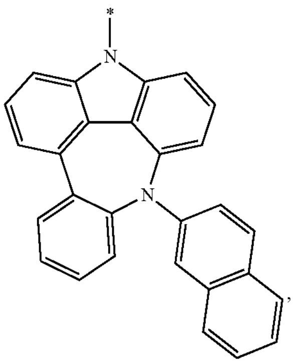
,
H2-22
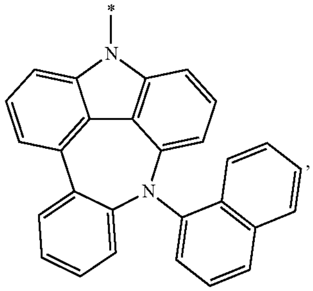
,
H2-23
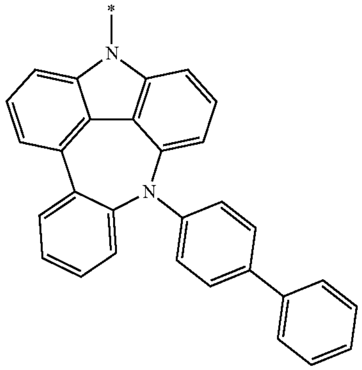
,
H2-24
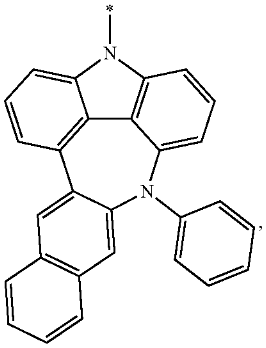
, -continued
H2-25
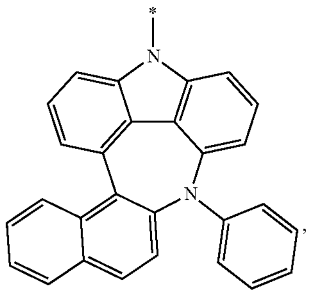
H2-26
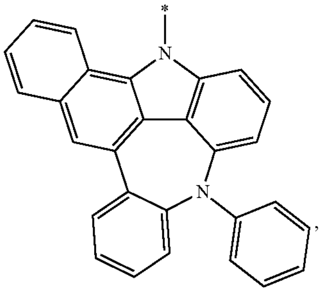
H2-27
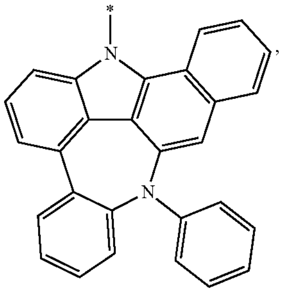
H2-28
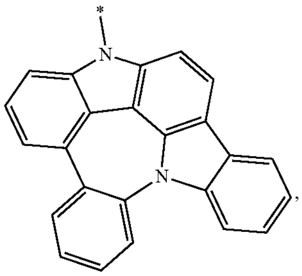
H2-29
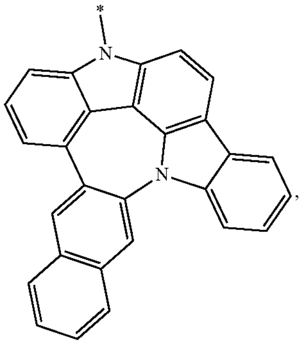
-continued
H2-30
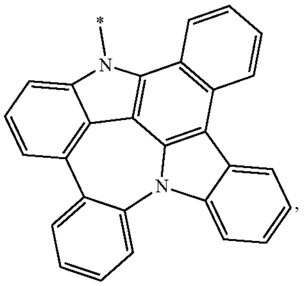
H2-31
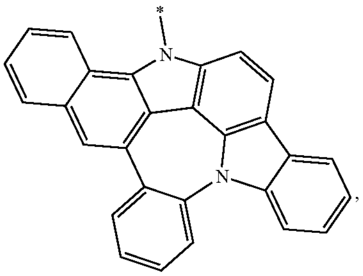
H2-32
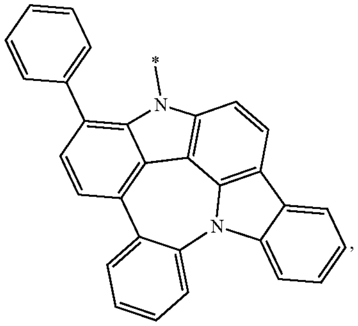
H2-33
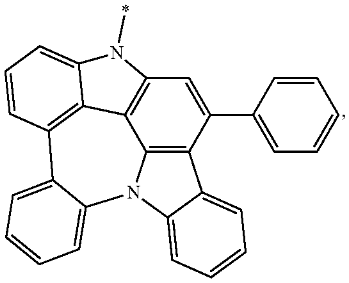
H2-34
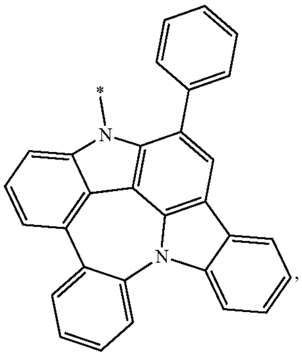

-continued
H2-35
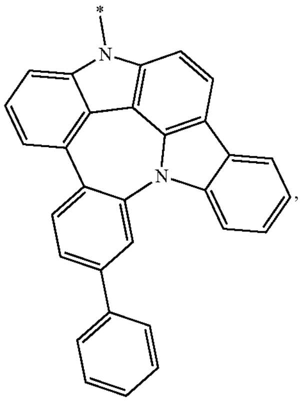
H2-36
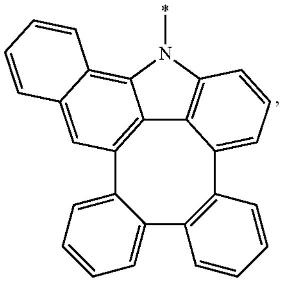
H2-37
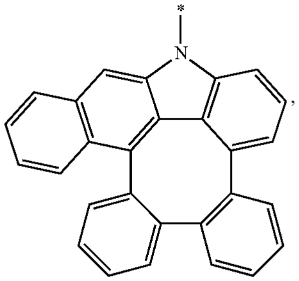
H2-38
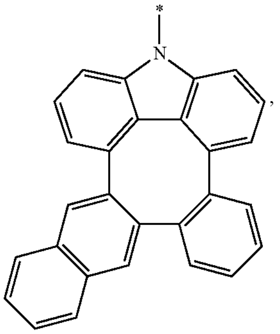
-continued
H2-39
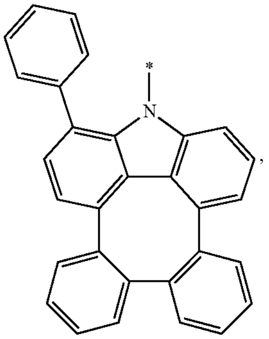
H2-40
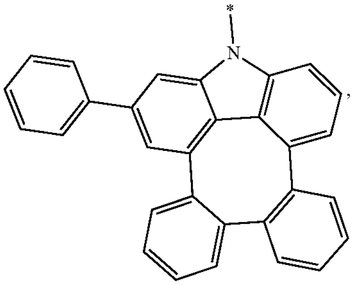
H2-41
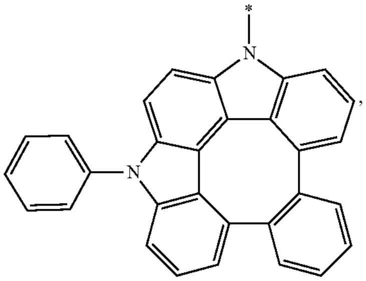
H2-42
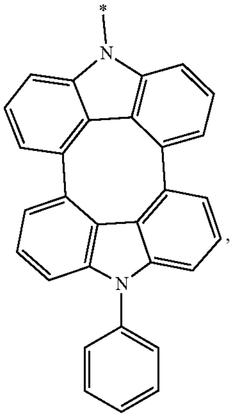
H2-43
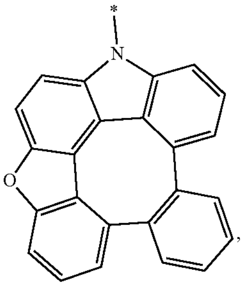

-continued
H2-44
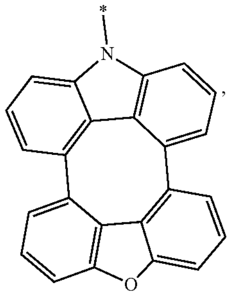,
H2-45
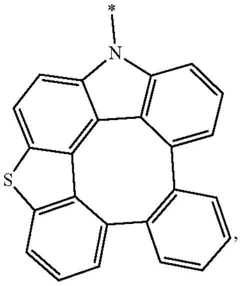,
H2-46
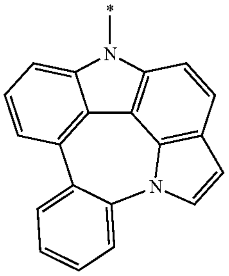,
H2-47
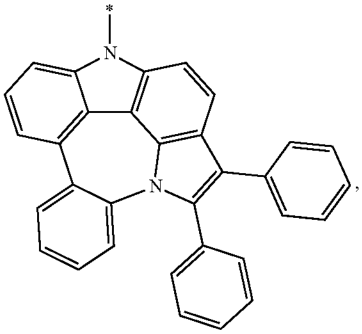,
H2-48
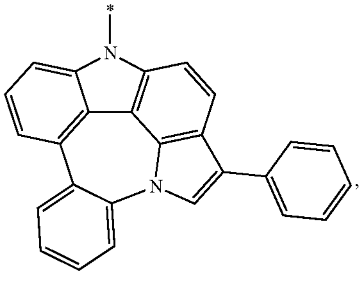,
-continued
H2-49
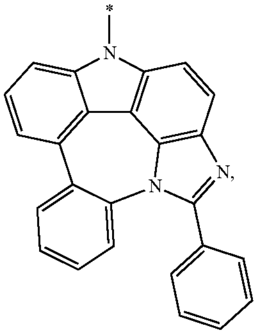
H2-50
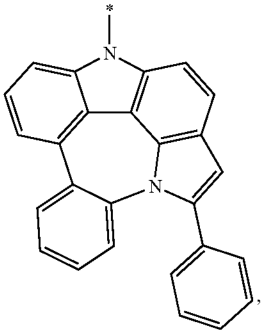,
H2-51
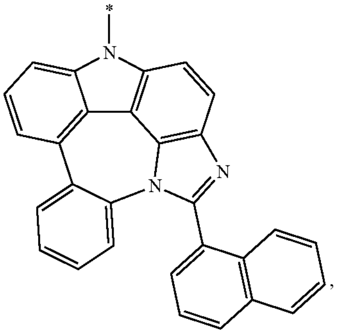,
H2-52
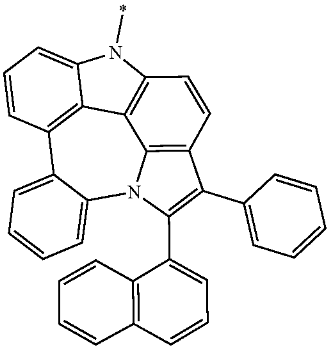, and -continued

H2-53

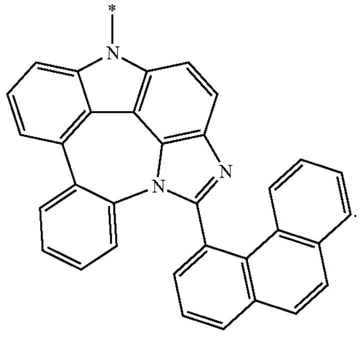

In this embodiment, "*" represents the position at which any of structures H2-1 to H2-53 is joined to the $L_2$.

According to an embodiment of the present disclosure, wherein, hydrogens in the H2-1 to H2-53 can be partially or completely substituted with deuterium.

According to an embodiment of the present disclosure, wherein, in the first compound and the second compound, at least one of $Ar_1$ or $Ar_2$ is, at each occurrence identically or differently, selected from substituted or unsubstituted heteroaryl having 3 to 30 carbon atoms. For example, the $Ar_1$ is selected from substituted or unsubstituted aryl having 6 to 30 carbon atoms, and the $Ar_2$ is selected from substituted or unsubstituted heteroaryl having 3 to 30 carbon atoms; or the $Ar_1$ is selected from substituted or unsubstituted heteroaryl having 3 to 30 carbon atoms, and the $Ar_2$ is selected from substituted or unsubstituted aryl having 6 to 30 carbon atoms; or the $Ar_1$ and the $Ar_2$ are, at each occurrence identically or differently, selected from substituted or unsubstituted heteroaryl having 3 to 30 carbon atoms.

According to an embodiment of the present disclosure, wherein, in the first compound and the second compound, the $Ar_1$ and the $Ar_2$ have, at each occurrence identically or differently, a structure represented by any one of the following structures:

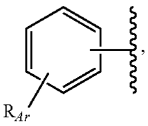,
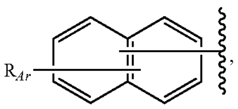,
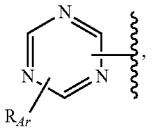,
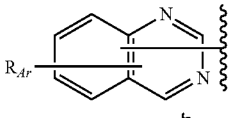,
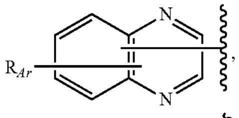,
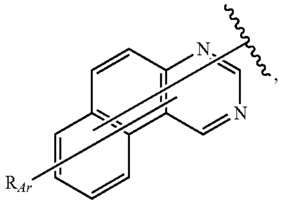,
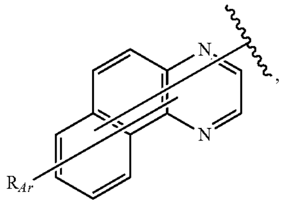,
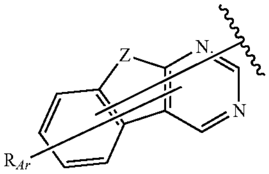, -continued

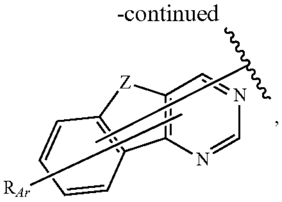, and

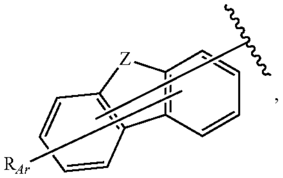, wherein, Z is selected from O, S, $CR_zR_z$, $SiR_zR_z$, $NR_z$, $BR_z$ or $PR_z$; when two $R_z$ exist at the same time, the two $R_z$ can be identical or different;

$R_{Ar}$ represents, at each occurrence identically or differently, mono-substitution, multiple substitutions or non-substitution;

$R_z$ and $R_{Ar}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, an isocyano group, a hydroxyl group, a sulfanyl group, and combinations thereof;

adjacent substituents $R_z$, $R_{Ar}$ can be optionally joined to form a ring.

In this embodiment, "" ~~~ "" represents the position at which any of structures $Ar_1$ and $Ar_2$ is joined to the $L_1$ or the $L_2$.

In the present disclosure, the expression that adjacent substituents $R_z$, $R_A$, can be optionally joined to form a ring is intended to mean that any one or more of groups of adjacent substituents, such as adjacent substituents $R_z$, adjacent substituents $R_{Ar}$, and adjacent substituents $R_z$ and $R_{Ar}$, can be joined to form a ring. Obviously, it is possible that none of these groups of adjacent substituents are joined to form a ring.

According to an embodiment of the present disclosure, wherein, in the first compound and the second compound, the $Ar_1$ and the $Ar_2$ have, at each occurrence identically or differently, a structure represented by any one of the following structures:

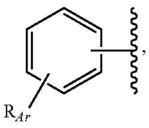,
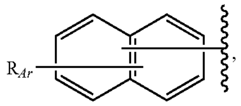,
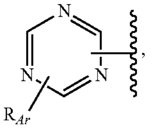,
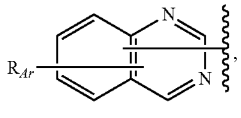,
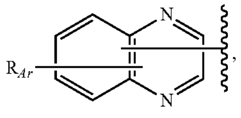,

-continued

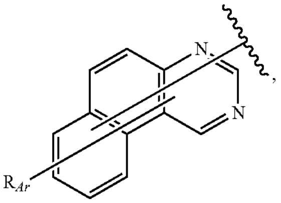

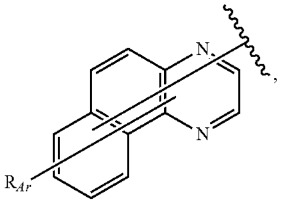

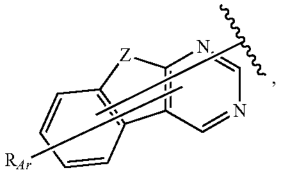

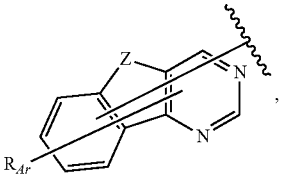

, and

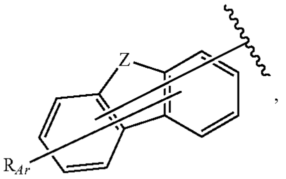

wherein, Z is selected from O, S, $CR_zR_z$, $SiR_zR_z$ or $NR_z$; when two $R_z$ exist at the same time, the two $R_z$ can be identical or different;

$R_{Ar}$ represents, at each occurrence identically or differently, mono-substitution, multiple substitutions or non-substitution;

$R_z$ and $R_{Ar}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, and combinations thereof;

adjacent substituents $R_z$, $R_{Ar}$ can be optionally joined to form a ring.

In this embodiment, "" "" represents the position at which any of structures $Ar_1$ and $Ar_2$ is joined to the $L_1$ or the $L_2$.

According to an embodiment of the present disclosure, wherein, in the first compound and the second compound, $Ar_1$ and $Ar_2$ have, at each occurrence identically or differently, a structure represented by any one of the following structures:

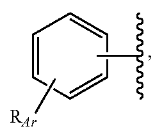

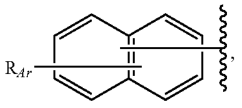

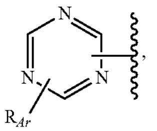

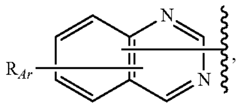

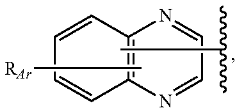

-continued

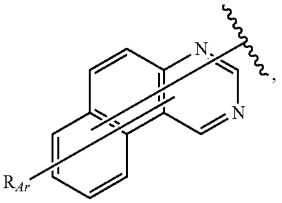

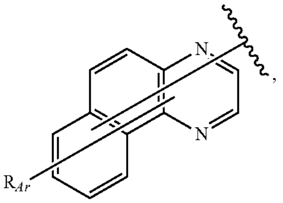

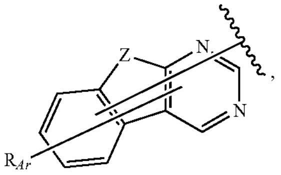

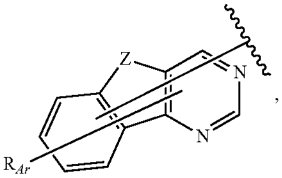

, and

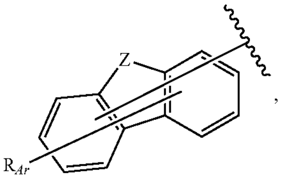

wherein, Z is selected from O, S, $CR_zR_z$, $SiR_zR_z$ or $NR_z$; when two $R_z$ exist at the same time, the two $R_z$ can be identical or different;

$R_{Ar}$ represents, at each occurrence identically or differently, mono-substitution, multiple substitutions or non-substitution;

$R_z$ and $R_{Ar}$ are, at each occurrence identically or differently, selected from the group consisting of: hydrogen, deuterium, fluorine, cyano, methyl, ethyl, propyl, isopropyl, tert-butyl, phenyl, biphenyl, naphthyl, 9-phenylcarbazolyl, naphthylphenyl, phenylpyridyl, dibenzofuranyl, dibenzothiophenyl, 9,9-dimethylfluorenyl, silafluorenyl, carbazolyl, pyridyl, pyrimidyl, 4-cyanophenyl, triphenylenyl, terphenyl, and combinations thereof;

adjacent substituents $R_z$, $R_{Ar}$ can be optionally joined to form a ring.

In this embodiment, "" "" represents the position at which any of structures $Ar_1$ and $Ar_2$ is joined to the $L_1$ or the $L_2$.

According to an embodiment of the present disclosure, wherein, in the first compound and the second compound, the $Ar_1$ and $Ar_2$ are, at each occurrence identically or differently, selected from the group consisting of the following structures:

Ar-1

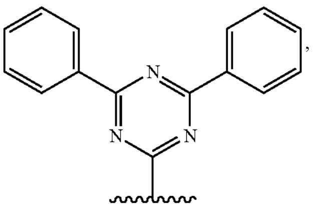

-continued
Ar-2
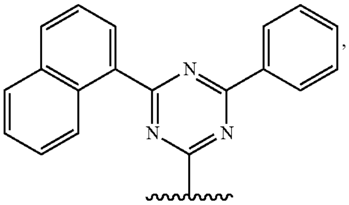
,
Ar-3
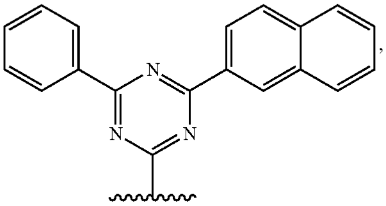
,
Ar-4
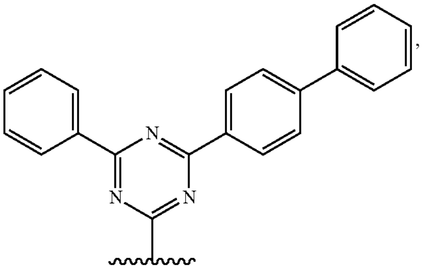
,
Ar-5
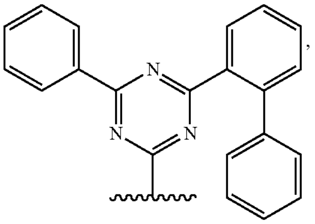
,
Ar-6
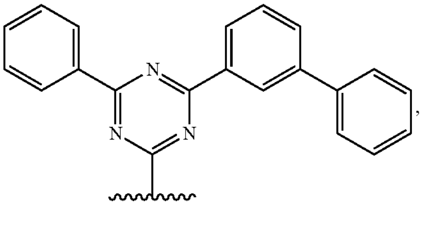
,
Ar-7
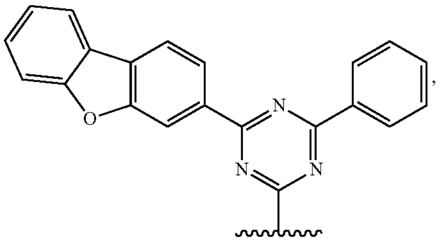
,
-continued
Ar-8
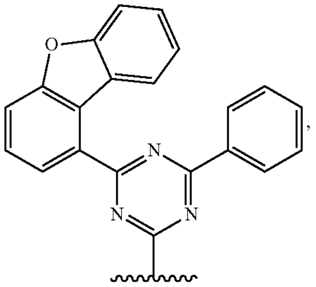
,
Ar-9
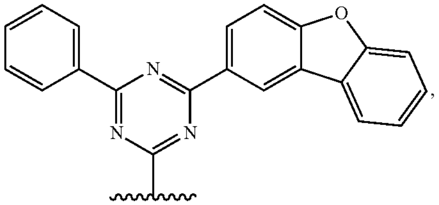
,
Ar-10
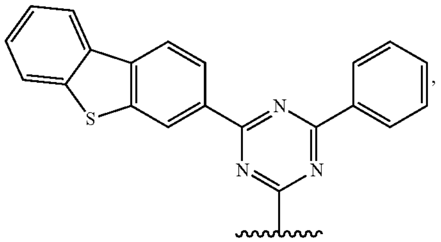
,
Ar-11
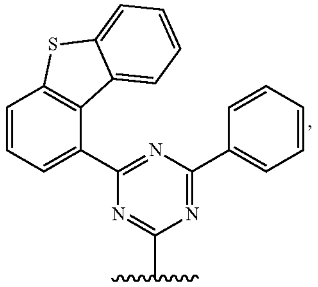
,
Ar-12
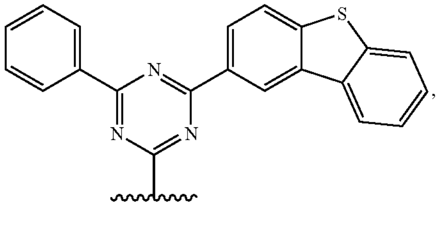
,
Ar-13
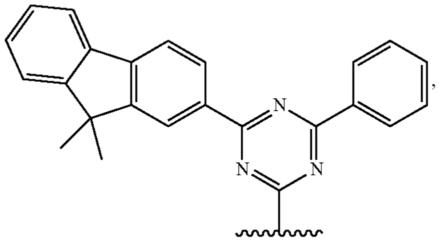
, -continued
Ar-14
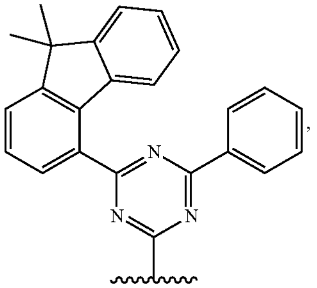
Ar-15
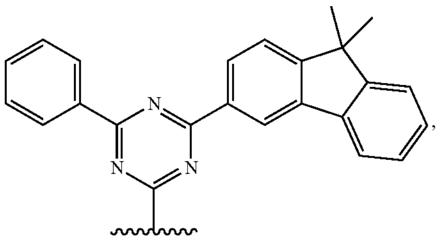
Ar-16
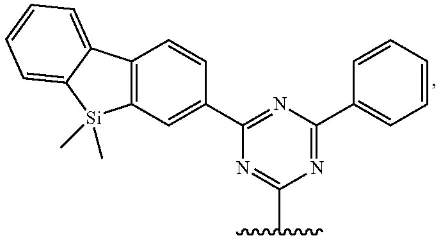
Ar-17
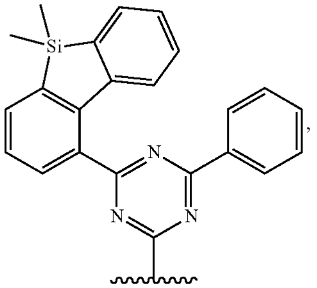
Ar-18
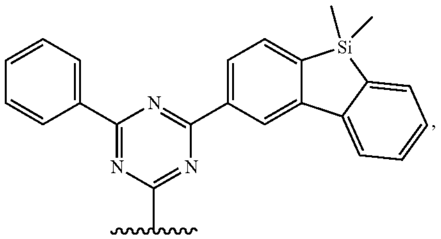
Ar-19
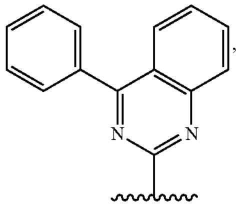
-continued
Ar-20
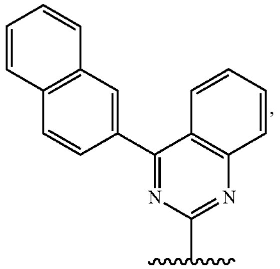
Ar-21
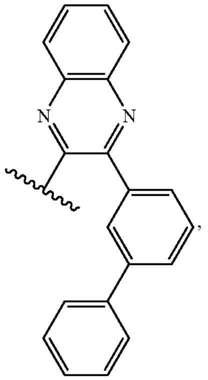
Ar-22
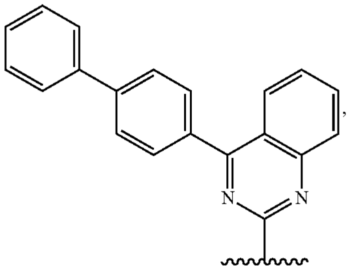
Ar-23
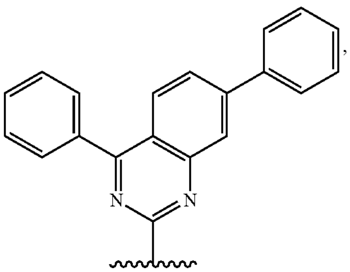
Ar-24
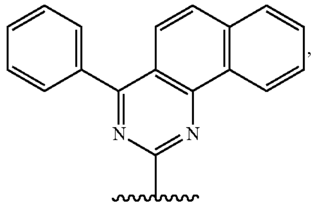

-continued
Ar-25
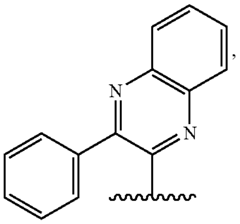
Ar-26
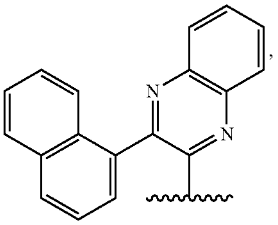
Ar-27
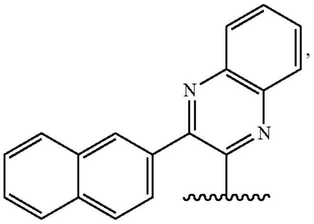
Ar-28
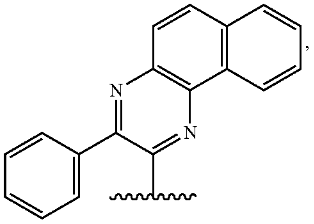
Ar-29
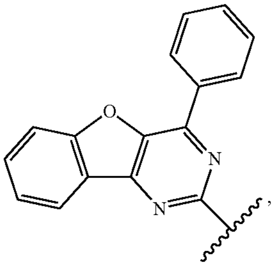
Ar-30
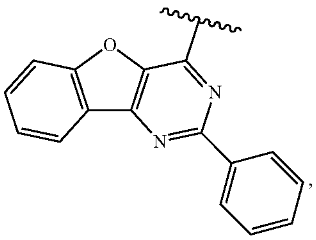
-continued
Ar-31
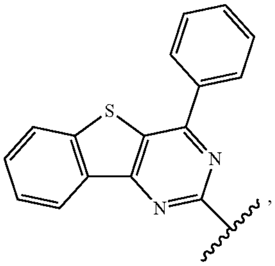
Ar-32
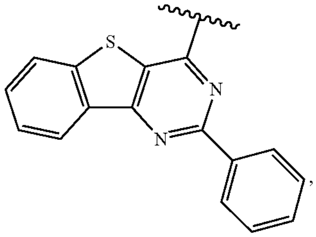
Ar-33
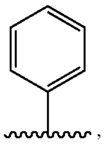
Ar-34
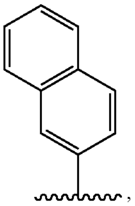
Ar-35
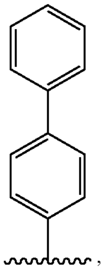
Ar-36
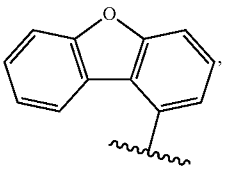
Ar-37
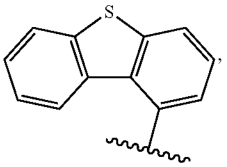

-continued
Ar-38
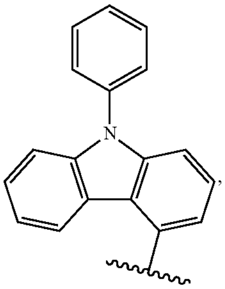,
Ar-39
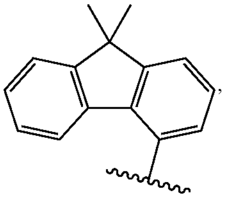,
Ar-40
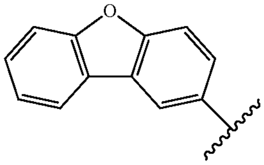,
Ar-41
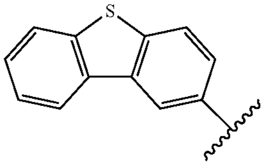,
Ar-42
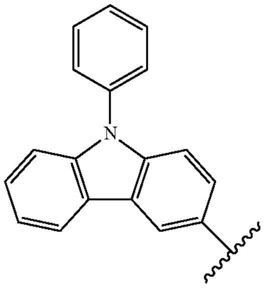,
Ar-43
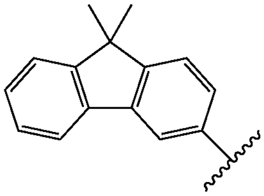,
Ar-44
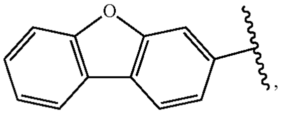,
Ar-45
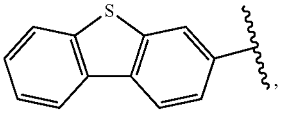,
-continued
Ar-46
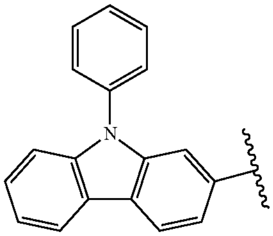,
Ar-47
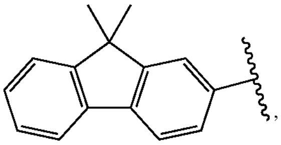,
Ar-48
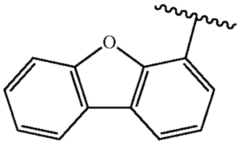,
Ar-49
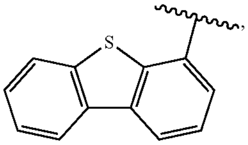,
Ar-50
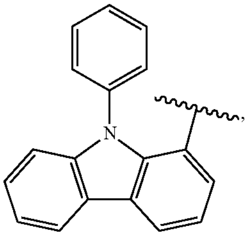,
Ar-51
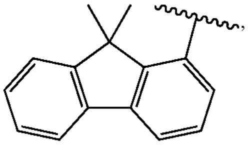,
Ar-52
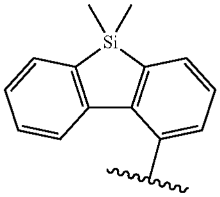, and
Ar-53
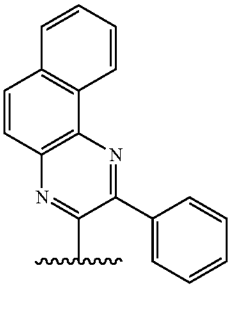.

In this embodiment, “"∼∼"” represents the position at which any of structures Ar-1 to Ar-53 is joined to the $L_1$ or the $L_2$.

According to an embodiment of the present disclosure, wherein, hydrogens in the Ar-1 to Ar-53 can be partially or completely substituted with deuterium.

According to an embodiment of the present disclosure, wherein, in the first compound and the second compound, the $L_1$ and $L_2$ are, at each occurrence identically or differently, selected from the group consisting of: a single bond, substituted or unsubstituted arylene having 6 to 24 carbon atoms, substituted or unsubstituted heteroarylene having 3 to 24 carbon atoms, and combinations thereof.

According to an embodiment of the present disclosure, wherein, in the first compound and the second compound, $L_1$ and $L_2$ are, at each occurrence identically or differently, selected from the group consisting of: a single bond, phenylene, naphthylene, biphenylene, terphenylene, triphenylenylene, dibenzofuranylene, dibenzothiophenylene, pyridinylene, thiophenylene, and combinations thereof.

According to an embodiment of the present disclosure, $L_1$ and $L_2$ are, at each occurrence identically or differently, selected from the group consisting of the following structures:

L-0 a single bond

L-1

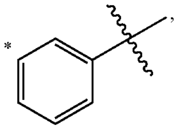

L-2

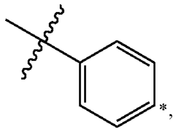

L-3

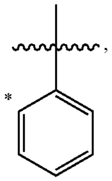

L-4

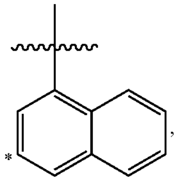

L-5

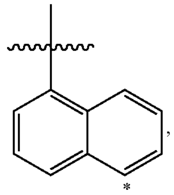

-continued

L-6

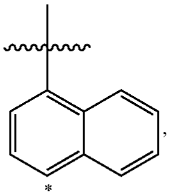

L-7

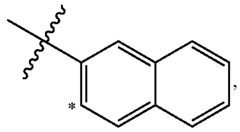

L-8

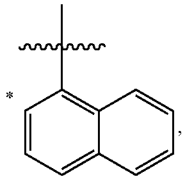

L-9

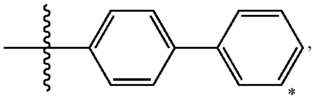

L-10

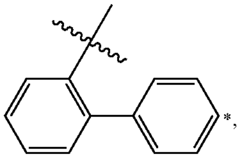

L-11

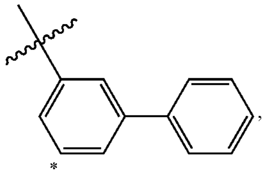

L-12

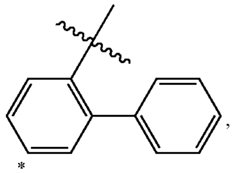

L-13

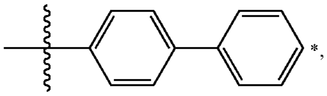

L-14

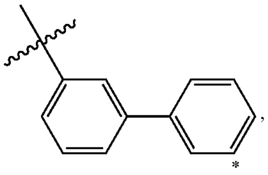

-continued

L-15

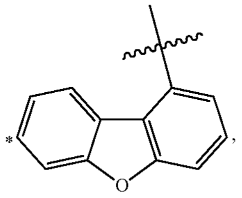

L-16

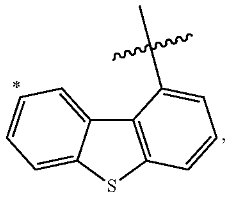

L-17

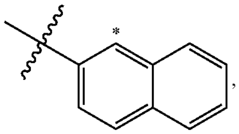

L-18

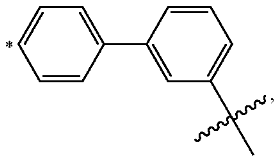

L-19

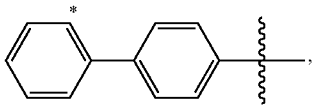

L-20

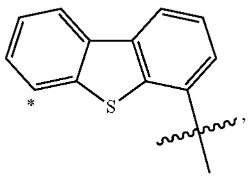

L-21

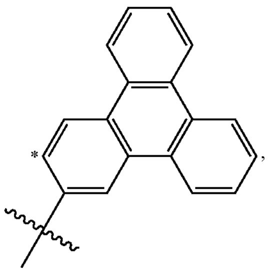

L-22

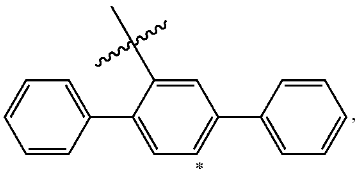

-continued

L-23

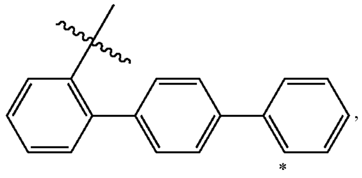

L-24

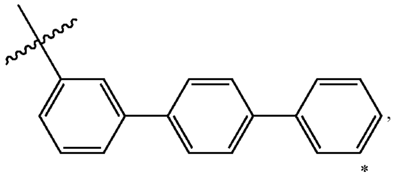

L-25

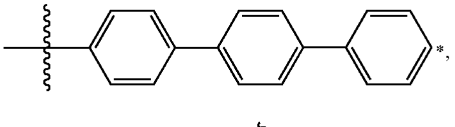

L-26

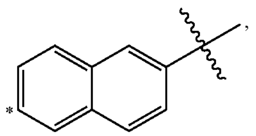

, and

L-27

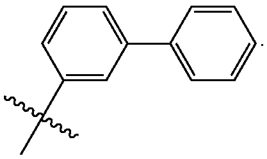

In this embodiment, in the structures of the L-1 to L-27, "*" represents the position at which structure $L_1$ or $L_2$ is joined to the $H_1$ or the $H_2$, and "〰" represents the position at which structure $L_1$ or $L_2$ is joined to the $Ar_1$ or the $Ar_2$.

According to an embodiment of the present disclosure, wherein, hydrogens in the structures of the L-1 to L-27 can be partially or completely substituted with deuterium.

According to an embodiment of the present disclosure, wherein, the first compound has a structure of $H_1$-$L_1$-$Ar_1$, wherein the $H_1$ is selected from any one of the group consisting of H-1 to H-139, the $L_1$ is selected from any one of the group consisting of L-0 to L-27, and the $Ar_1$ is selected from any one of the group consisting of Ar-1 to Ar-53. Optionally, hydrogens in the structure of the first compound can be partially or completely substituted with deuterium.

According to an embodiment of the present disclosure, wherein, the first compound is selected from the group consisting of Compound 1-1 to Compound 1-322, and specific structures of the Compound 1-1 to Compound 1-322 are shown in claim 14.

According to an embodiment of the present disclosure, wherein, hydrogens in the Compound 1-1 to Compound 1-322 can be partially or completely substituted with deuterium.

According to an embodiment of the present disclosure, wherein, the second compound has a structure of $H_2$-$L_2$-$Ar_2$, wherein the $H_2$ is selected from the group consisting of H-1 to H-139 and H2-1 to H2-53, the $L_2$ is selected from any one of the group consisting of L-0 to L-27, and the $Ar_2$ is selected from any one of the group consisting of Ar-1 to Ar-53.

Optionally, hydrogens in the structure of the second compound can be partially or completely substituted with deuterium.

According to an embodiment of the present disclosure, wherein, the second compound is selected from the group consisting of Compound 1-1 to Compound 1-322 and Compound 2-1 to Compound 2-316, and specific structures of the Compound 2-1 to Compound 2-316 are shown in claim 15.

According to an embodiment of the present disclosure, wherein, hydrogens in the Compound 1-1 to Compound 1-322 and Compound 2-1 to Compound 2-316 can be partially or completely substituted with deuterium.

According to an embodiment of the present disclosure, wherein, the organic layer is an emissive layer, and the first compound and the second compound are host materials.

According to an embodiment of the present disclosure, wherein, the emissive layer further comprises at least one phosphorescent material.

According to an embodiment of the present disclosure, wherein, in the emissive layer, the at least one phosphorescent material is a metal complex, and the metal complex has a general formula of $M(L_a)_m(L_b)_n(L_c)_q$;

wherein the M is selected from a metal with a relative atomic mass greater than 40;

$L_a$, $L_b$, and $L_c$ are a first ligand, a second ligand and a third ligand coordinated to the M, respectively; $L_a$, $L_b$, and $L_c$ can be optionally joined to form a multidentate ligand;

$L_a$, $L_b$, and $L_c$ can be identical or different; m is 1, 2 or 3; n is 0, 1 or 2; q is 0 or 1; the sum of m, n, and q equals to an oxidation state of the M; when m is greater than or equal to 2, the plurality of $L_a$ can be identical or different; when n is equal to 2, two $L_b$ can be identical or different;

$L_a$ has a structure represented by Formula 3:

Formula 3

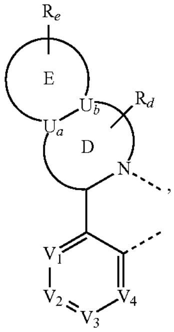

wherein, the ring D is selected from a 5-membered heteroaromatic ring or a 6-membered heteroaromatic ring;

the ring E is selected from a 5-membered unsaturated carbocyclic ring, a benzene ring, a 5-membered heteroaromatic ring or a 6-membered heteroaromatic ring;

the ring D and ring E are fused via $U_a$ and $U_b$;

$U_a$ and $U_b$ are, at each occurrence identically or differently, selected from C or N;

$R_d$ and $R_e$ represent, at each occurrence identically or differently, mono-substitution, multiple substitutions or non-substitution;

$V_1$ to $V_4$ are, at each occurrence identically or differently, selected from $CR_v$ or N;

$R_d$, $R_e$, and $R_v$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon.atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents $R_d$, $R_e$, $R_v$ can be optionally joined to form a ring;

$L_b$ and $L_c$ are, at each occurrence identically or differently, selected from the group consisting of the following structures:

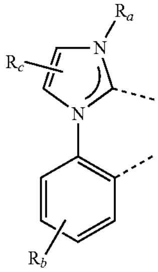
,
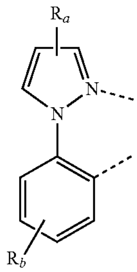
,
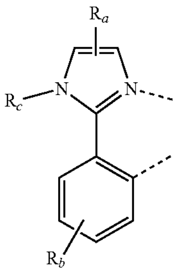
,
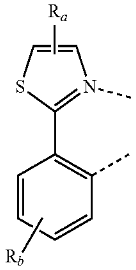
,
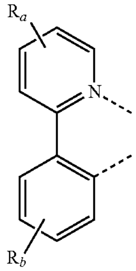
,
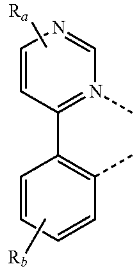
,
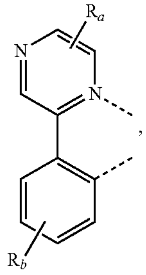
,
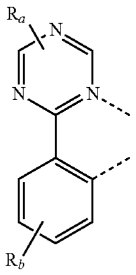
,
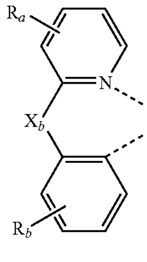
, -continued

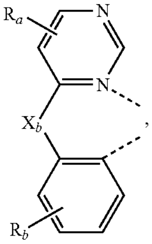
,
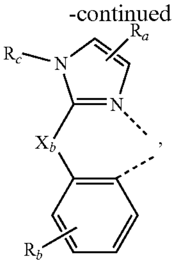
, and
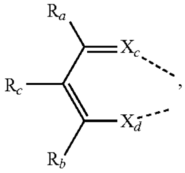
, wherein, $R_a$, $R_b$, and $R_c$ represent, at each occurrence identically or differently, mono-substitution, multiple substitutions or non-substitution;

$X_b$ is, at each occurrence identically or differently, selected from the group consisting of: O, S, Se, $NR_{N1}$, and $CR_{C1}R_{C2}$;

$X_c$ and $X_d$ are, at each occurrence identically or differently, selected from the group consisting of: O, S, Se, and $NR_{N2}$;

$R_a$, $R_b$, $R_c$, $R_{N1}$, $R_{N2}$, $R_{C1}$, and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

in structures of the ligands $L_b$ and $L_c$, adjacent substituents $R_a$, $R_b$, $R_e$, $R_{N1}$, $R_{N2}$, $R_{C1}$, and $R_{C2}$ can be optionally joined to form a ring.

In the present disclosure, the expression that adjacent substituents $R_d$, $R_e$, $R_v$ can be optionally joined to form a ring is intended to mean that when substituents $R_d$, $R_e$, and $R_v$ exist, any one or more of groups of adjacent substituents, such as adjacent substituents $R_d$, adjacent substituents $R_c$, adjacent substituents $R_v$, adjacent substituents $R_d$ and $R_e$, adjacent substituents $R_d$ and $R_v$, and adjacent substituents $R_e$ and $R_v$, can be joined to form a ring. Obviously, when substituents $R_d$, $R_e$ and $R_v$ exist, it is possible that none of these groups of substituents are joined to form a ring.

In this embodiment, the expression that adjacent substituents $R_a$, $R_b$, $R_c$, $R_{N1}$, $R_{N2}$, $R_{C1}$, and $R_{C2}$ can be optionally joined to form a ring is intended to mean that any one or more of groups of adjacent substituents, such as two substituents $R_a$, two substituents $R_b$, two substituents $R_c$, substituents $R_a$ and $R_b$, substituents $R_a$ and $R_c$, substituents $R_b$ and $R_c$, substituents $R_a$ and $R_{N1}$, substituents $R_b$ and $R_{N1}$, substituents $R_a$ and $R_{C1}$, substituents $R_a$ and $R_{C2}$, substituents $R_b$ and $R_{C1}$, substituents $R_b$ and $R_{C2}$, substituents $R_a$ and $R_{N2}$, substituents $R_b$ and $R_{N2}$, and substituents $R_{C1}$ and $R_{C2}$, can be joined to form a ring. Obviously, it is possible that none of these groups of substituents are joined to form a ring.

According to an embodiment of the present disclosure, wherein, in the emissive layer, the at least one phosphorescent material is a metal complex, and the metal complex has a general formula of $M(L_a)_m(L_b)_n$;

wherein the M is selected from a metal with a relative atomic mass greater than 40;

$L_a$ and $L_b$ are a first ligand and a second ligand coordinated to the M, respectively; $L_a$ and $L_b$ can be optionally joined to form a multidentate ligand;

m is 1, 2 or 3; n is 0, 1 or 2; the sum of m and n equals to the oxidation state of the M; when m is greater than or equal to 2, the plurality of $L_a$ can be identical or different; when n is equal to 2, two $L_b$ can be identical or different;

$L_a$ has a structure represented by Formula 3:

Formula 3

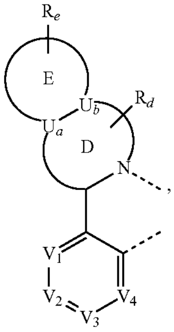
, wherein, the ring D is selected from a 5-membered heteroaromatic ring or a 6-membered heteroaromatic ring;

the ring E is selected from a 5-membered unsaturated carbocyclic ring, a benzene ring, a 5-membered heteroaromatic ring or a 6-membered heteroaromatic ring;

the ring D and the ring E are fused via $U_a$ and $U_b$;

$U_a$ and $U_b$ are, at each occurrence identically or differently, selected from C or N;

$R_d$ and $R_e$ represent, at each occurrence identically or differently, mono-substitution, multiple substitutions or non-substitution;

$V_1$ to $V_4$ are, at each occurrence identically or differently, selected from $CR_v$ or N;

$R_d$, $R_e$, and $R_v$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof;

adjacent substituents $R_d$, $R_e$, $R_v$ can be optionally joined to form a ring;

the ligand $L_b$ has the following structure:

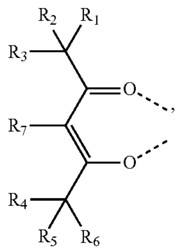

wherein $R_1$ to $R_7$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

According to an embodiment of the present disclosure, wherein, in the metal complex, the ligand $L_b$ has the following structure:

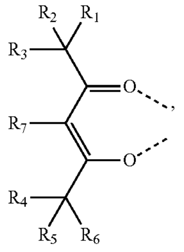

wherein at least one of $R_1$ to $R_3$ is selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms or combinations thereof; and/or at least one of $R_4$ to $R_6$ are selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, or combinations thereof.

According to an embodiment of the present disclosure, wherein, in the metal complex, the ligand $L_b$ has the following structure:

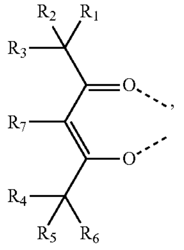

wherein at least two of $R_1$ to $R_3$ are, at each occurrence identically or differently, selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms or combinations thereof; and/or at least two of $R_4$ to $R_6$ are, at each occurrence identically or differently, selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, or combinations thereof.

According to an embodiment of the present disclosure, wherein, in the metal complex, the ligand $L_b$ has the following structure:

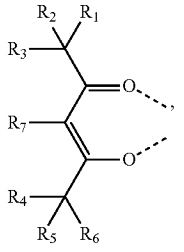

wherein at least two of $R_1$ to $R_3$ are, at each occurrence identically or differently, selected from substituted or unsubstituted alkyl having 2 to 20 carbon atoms, substituted or unsubstituted cycloalkyl having 3 to 20 ring carbon atoms, substituted or unsubstituted heteroalkyl having 2 to 20 carbon atoms, or combinations thereof; and/or at least two of $R_4$ to $R_6$ are, at each occurrence identically or differently, selected from substituted or unsubstituted alkyl having 2 to 20 carbon atoms, substituted or unsubstituted cycloalkyl having 3 to 20 ring carbon atoms, substituted or unsubstituted heteroalkyl having 2 to 20 carbon atoms or combinations thereof.

According to an embodiment of the present disclosure, in the device, wherein the at least one phosphorescent material is an Ir complex, a Pt complex or an Os complex.

According to an embodiment of the present disclosure, in the device, wherein the at least one phosphorescent material is an Ir complex and has a structure represented by any one of $Ir(L_a)(L_b)(L_c)$, $Ir(L_a)_2(L_b)$, $Ir(L_a)_2(L_c)$ or $Ir(L_a)(L_c)_2$.

According to an embodiment of the present disclosure, wherein, in the electroluminescent device, the at least one phosphorescent material is an Ir complex and contains the ligand $L_a$, and the ligand $L_a$ has a structure represented by Formula 3 and contains at least one structural unit selected from the group consisting of a 6-membered-fused-6-membered aromatic ring, a 6-membered-fused-6-membered heteroaromatic ring, a 6-membered-fused-5-membered aromatic ring, and a 6-membered-fused-5-membered heteroaromatic ring.

According to an embodiment of the present disclosure, wherein, in the electroluminescent device, the at least one phosphorescent material is an Ir complex and contains the ligand $L_a$, and the ligand $L_a$ has a structure represented by Formula 3 and contains at least one structural unit selected from the group consisting of naphthalene, phenanthrene, quinoline, isoquinoline, and azaphenanthrene.

According to an embodiment of the present disclosure, wherein, in the electroluminescent device, the at least one phosphorescent material is an Ir complex and contains the ligand $L_a$, and the ligand $L_a$ is, at each occurrence identically or differently, selected from any one of the group consisting of the following structures:

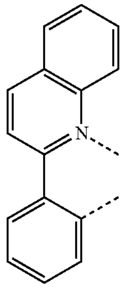
,
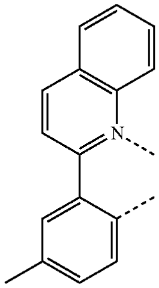
,
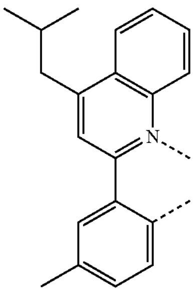
,
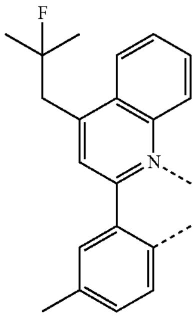
,
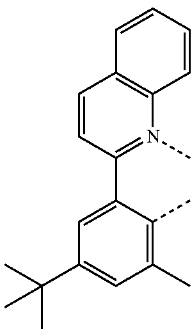
,
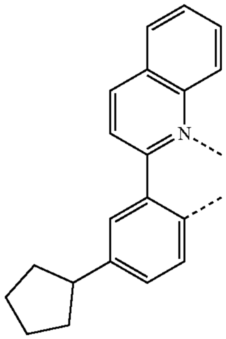
, -continued

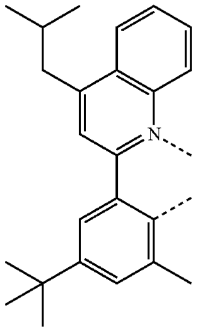
,
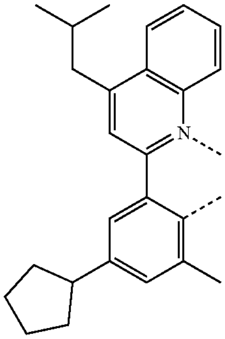
,
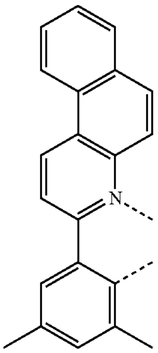
,
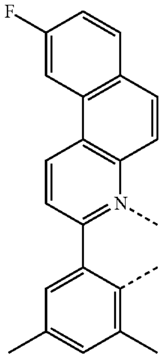
,
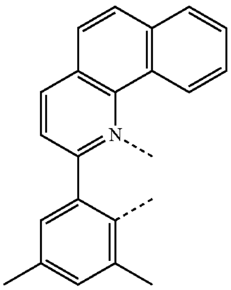
,
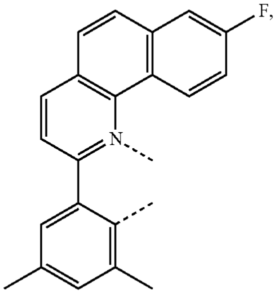
,
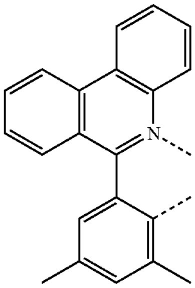
,
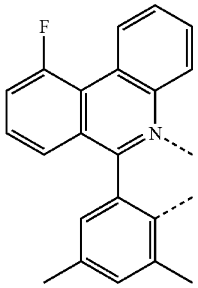
,
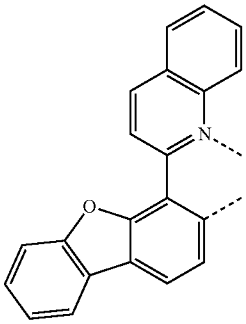
,
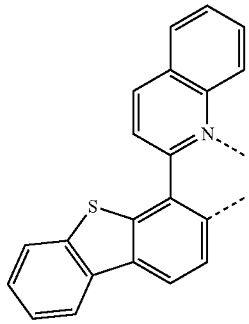
, -continued
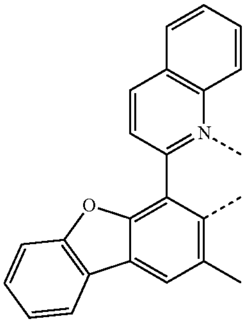
,
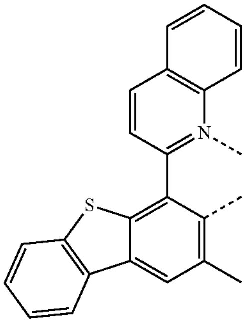
,
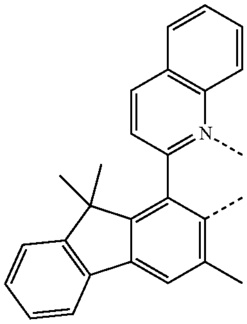
,
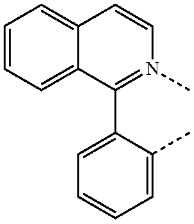
,
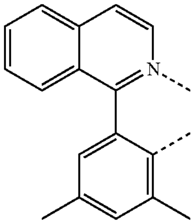
,
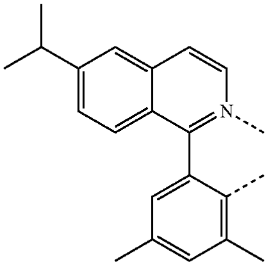
,
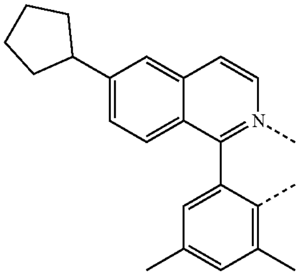
,
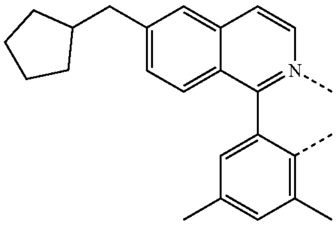
,
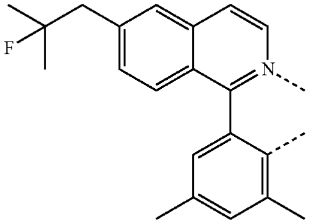
,
-continued
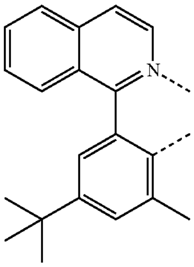
,
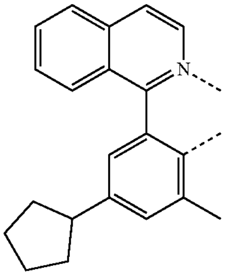
,
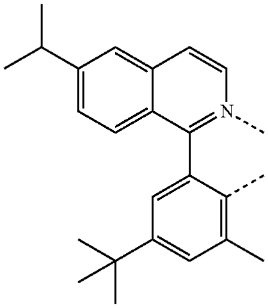
,
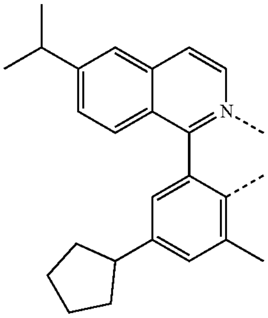
,
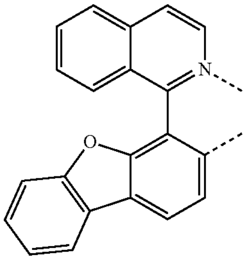
,
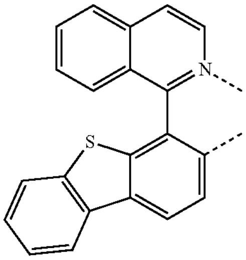
,
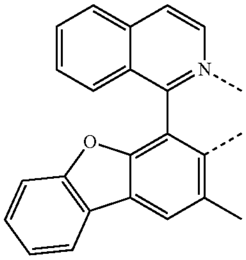
,
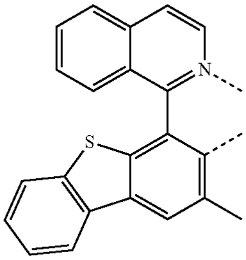
,
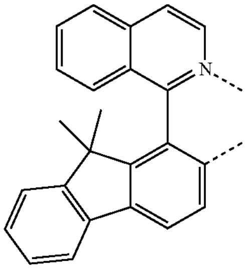
,
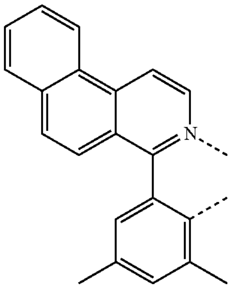
,
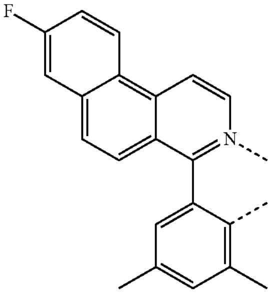
, -continued
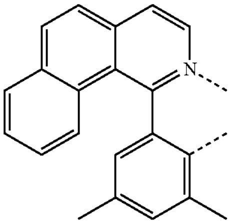 , 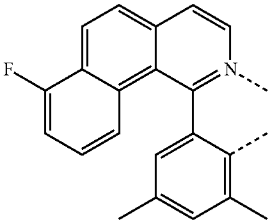 ,
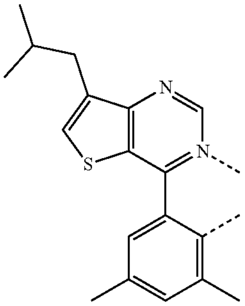 , 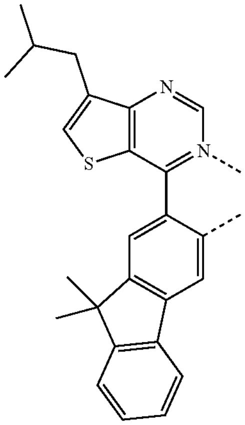 ,
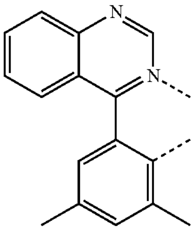 , 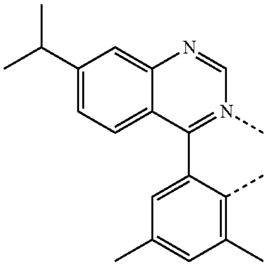 ,
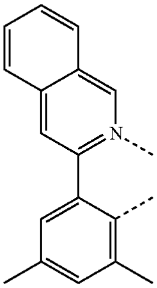 , 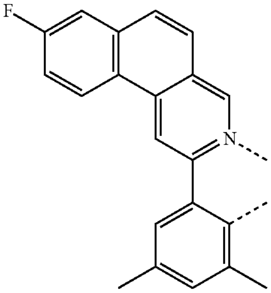 ,
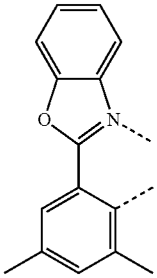 , 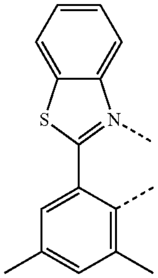 , and
-continued
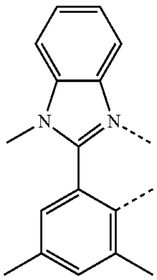 .
According to an embodiment of the present disclosure, wherein, in the electroluminescent device, the at least one phosphorescent material is an Ir complex and contains the ligand $L_b$, and the ligand $L_b$ is, at each occurrence identically or differently, selected from any one of the group consisting of the following structures:
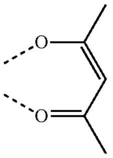 , 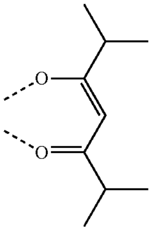 ,
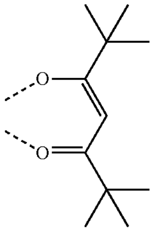 , 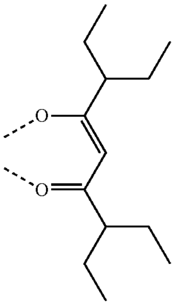 ,
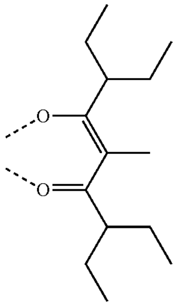 , 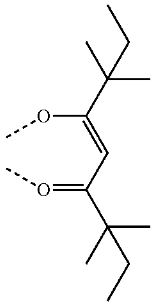 ,
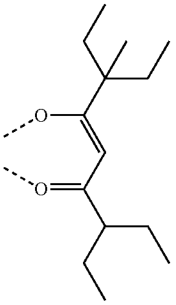 , 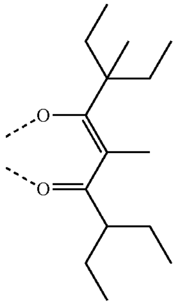 , -continued
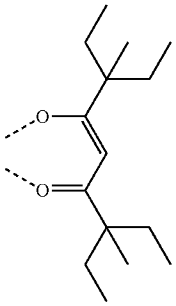
,
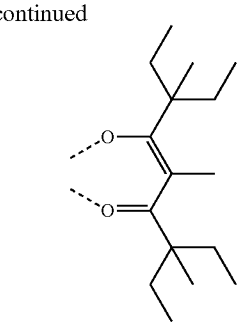
,
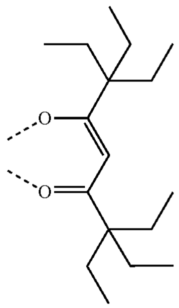
,
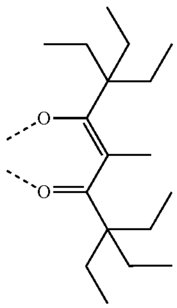
,
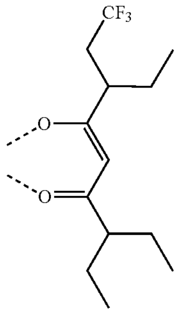
,
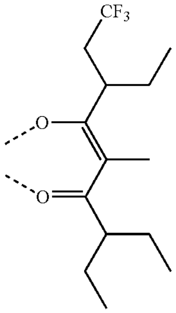
,
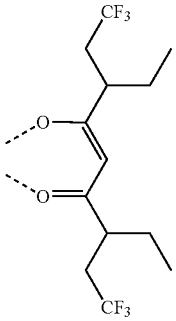
,
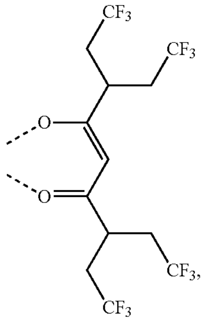
,
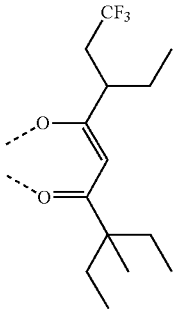
,
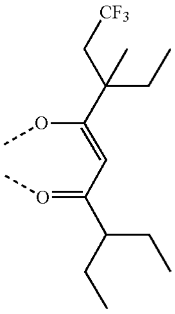
,
-continued
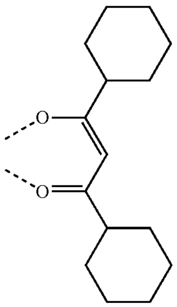
,
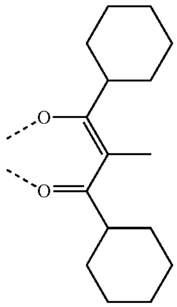
,
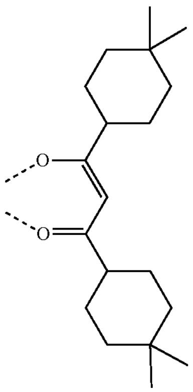
,
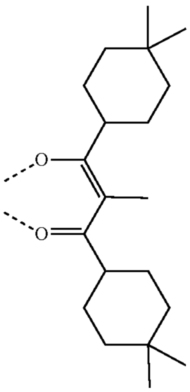
, and
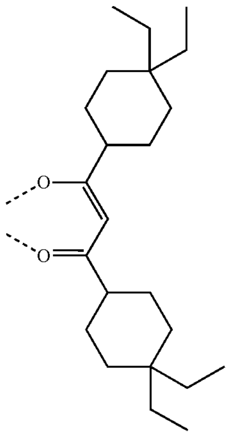
.
According to an embodiment of the present disclosure, wherein, in the electroluminescent device, the at least one phosphorescent material is selected from the group
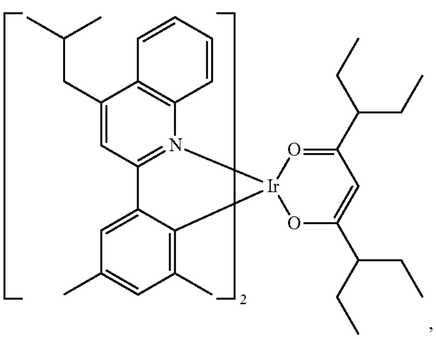
, -continued
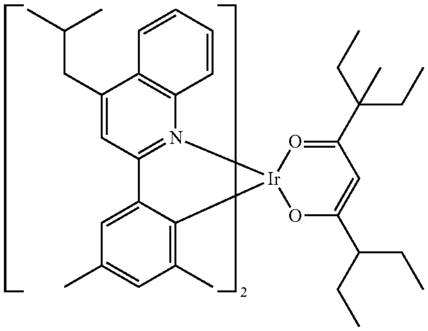
,
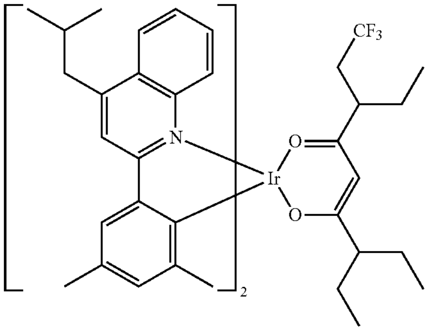
,
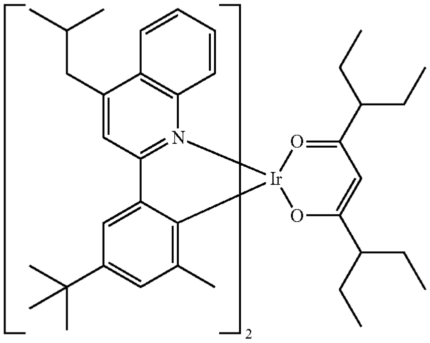
,
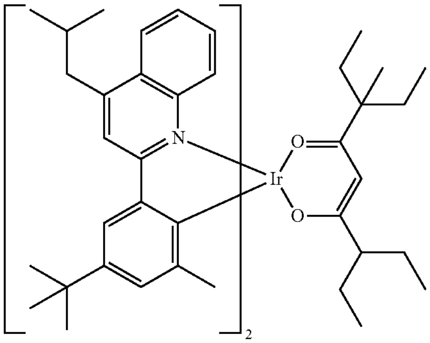
,
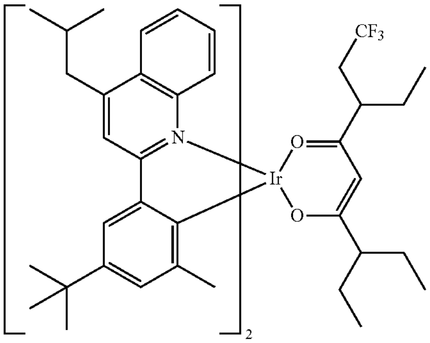
,
-continued
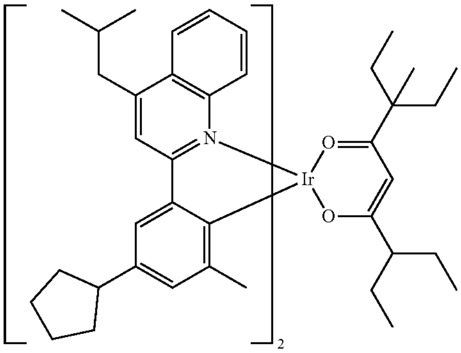
,
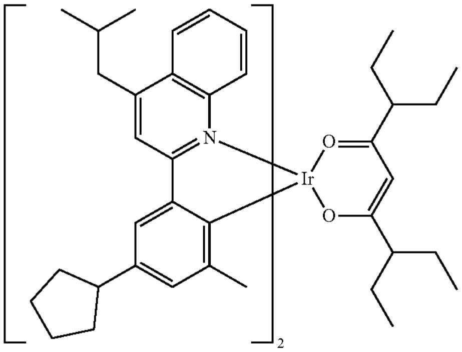
,
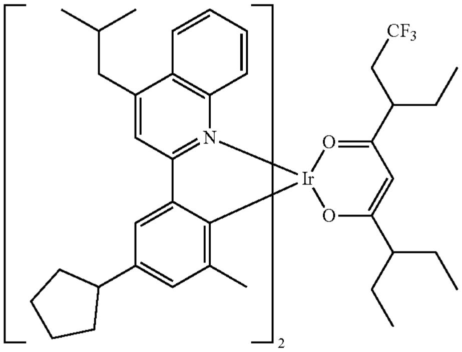
,
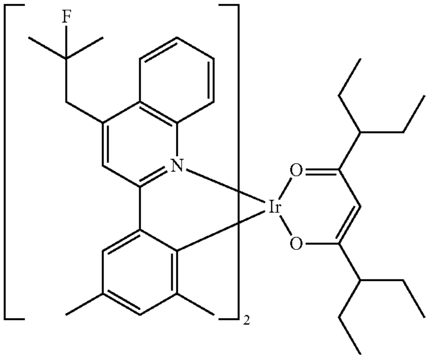
, -continued
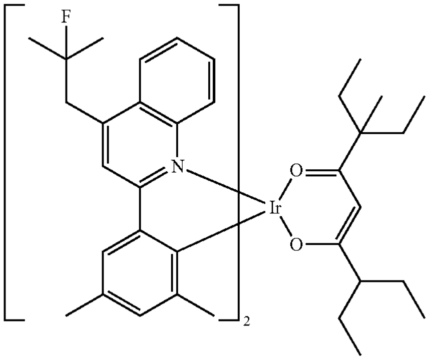
,
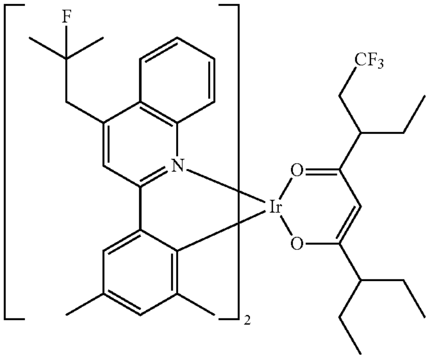
,
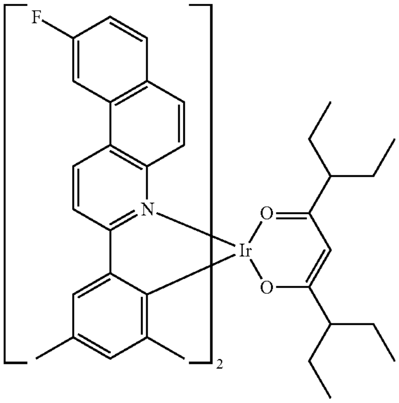
,
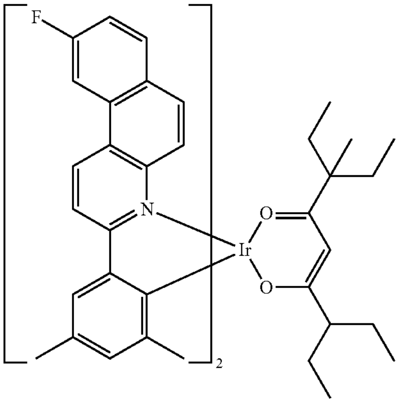
,
-continued
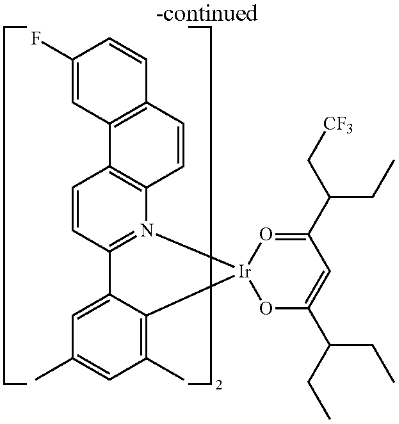
,
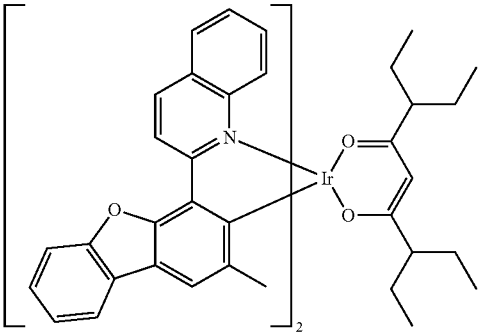
,
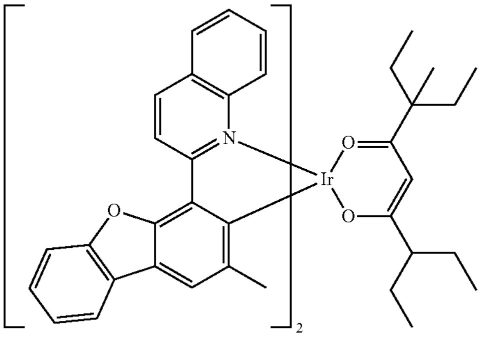
,
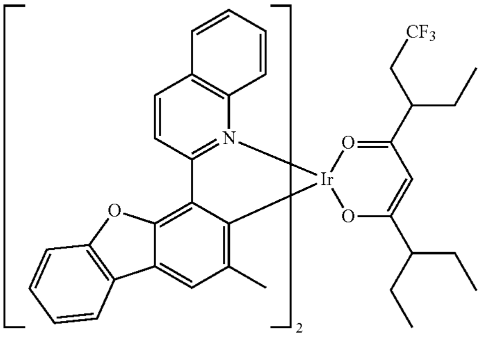
,
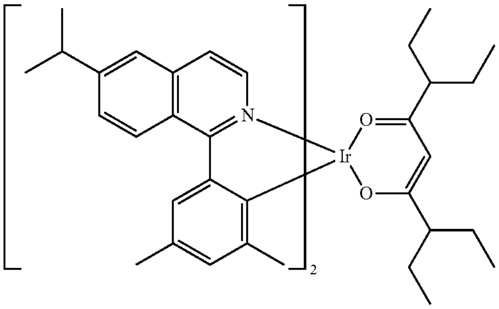
, -continued
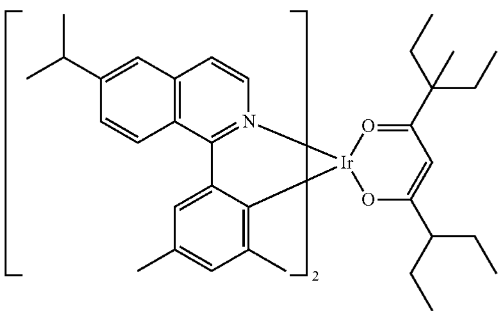
,
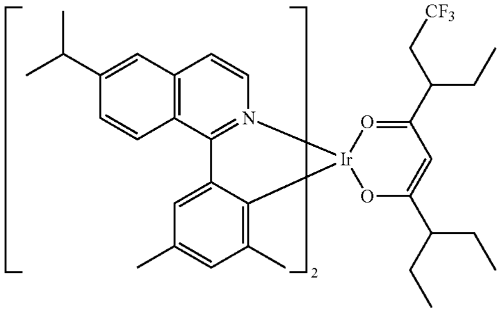
,
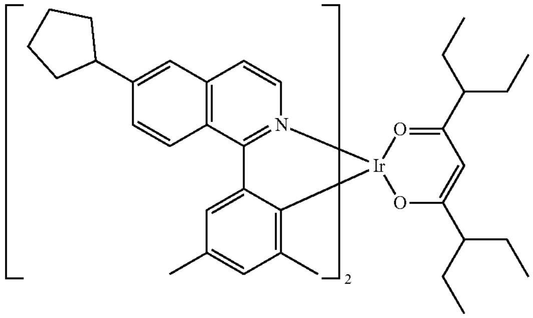
,
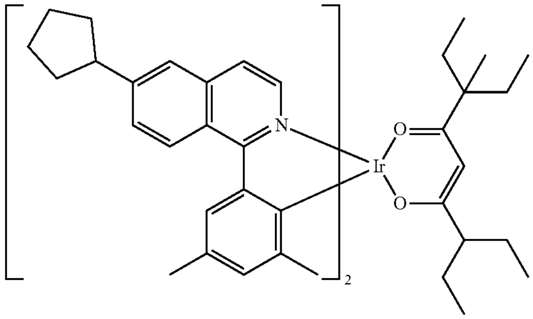
,
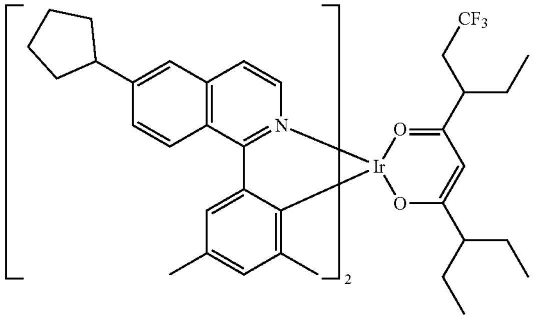
,
-continued
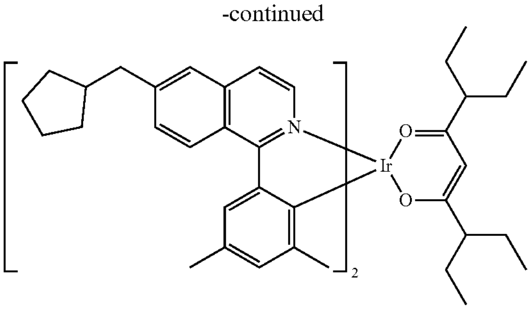
,
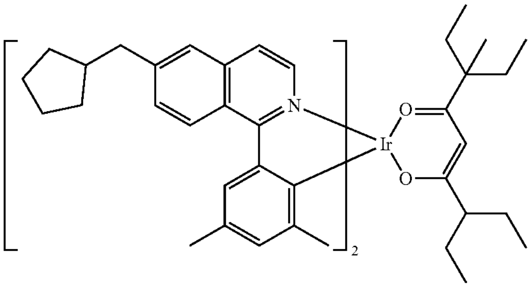
,
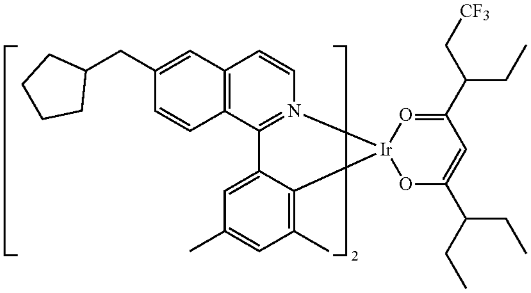
,
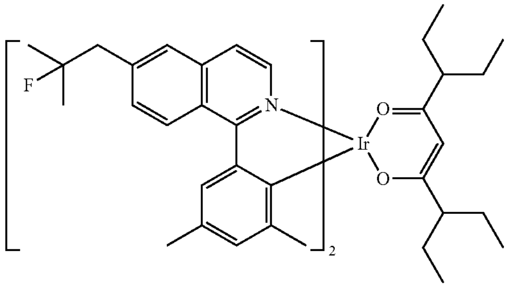
,
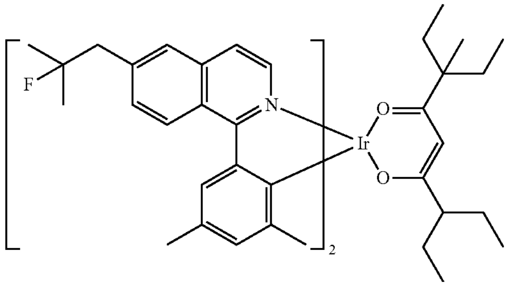
,
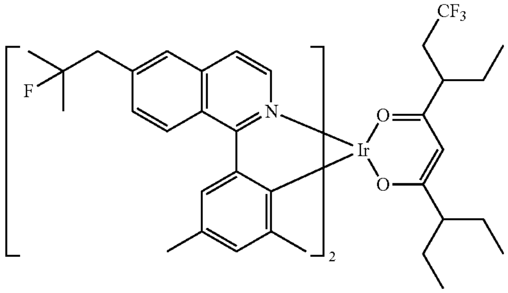
, -continued
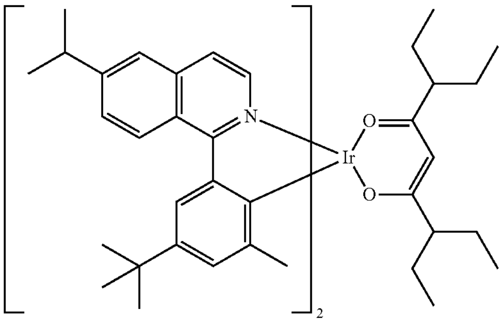
,
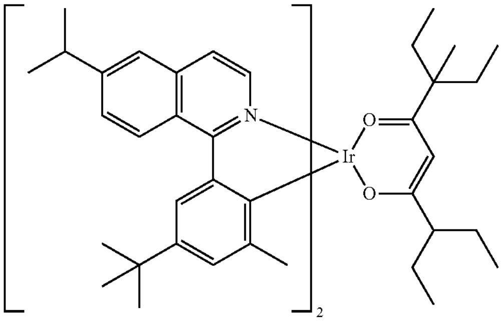
,
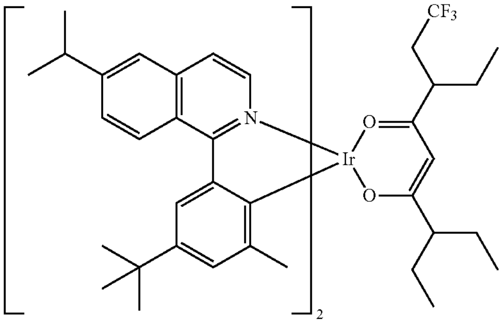
,
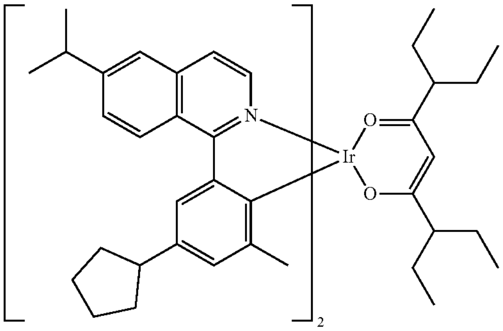
,
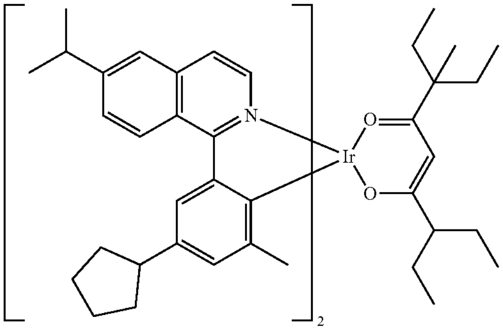
,
-continued
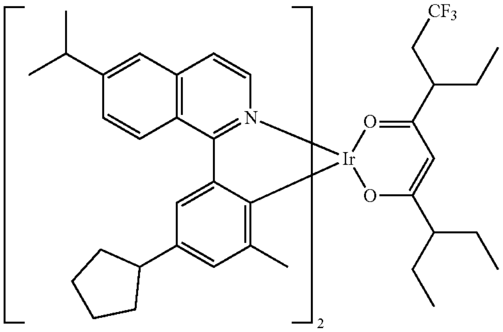
,
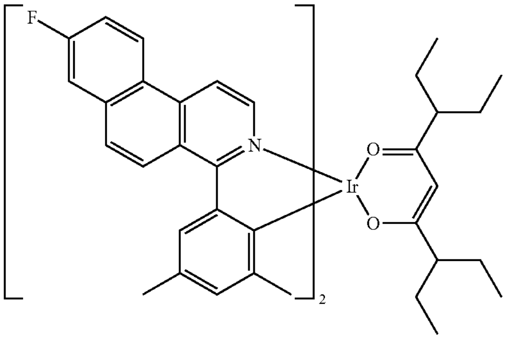
,
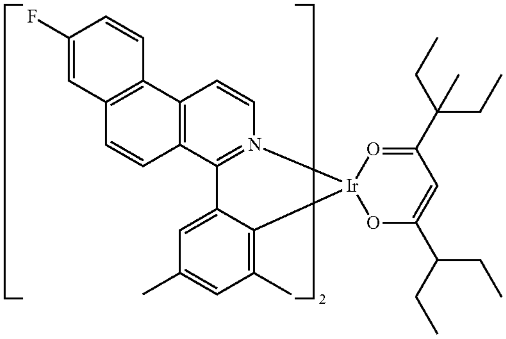
,
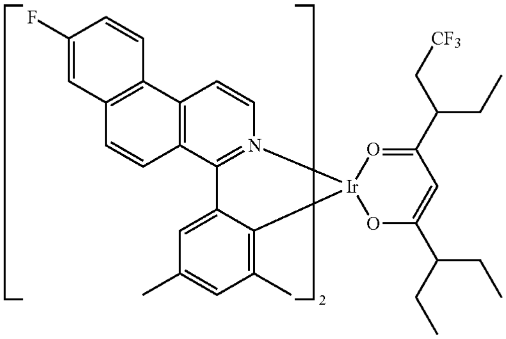
,
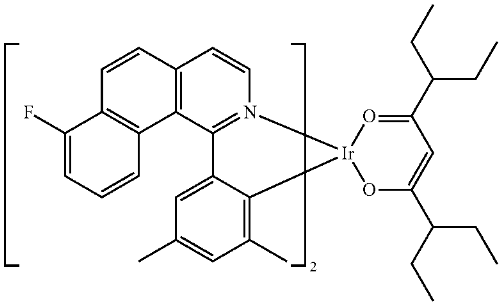
, -continued

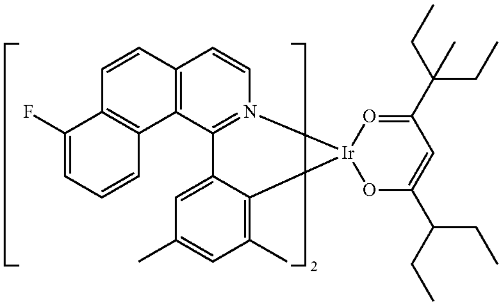

,

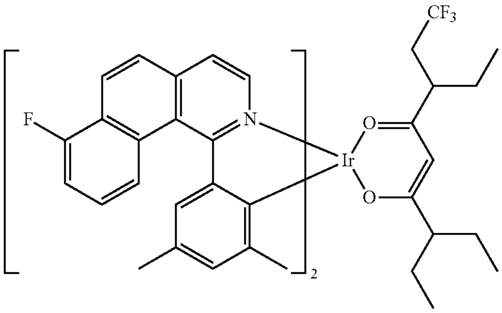

,

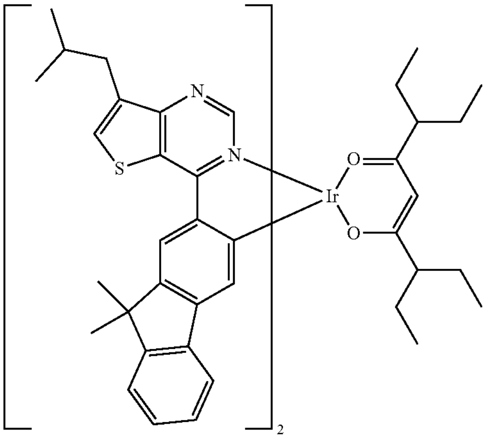

,

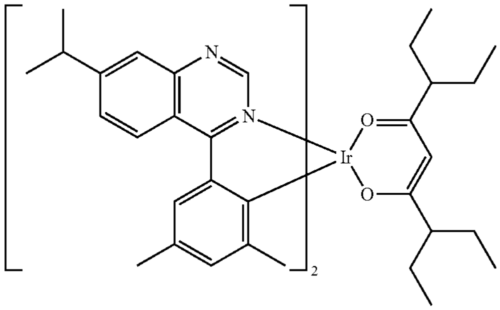

,

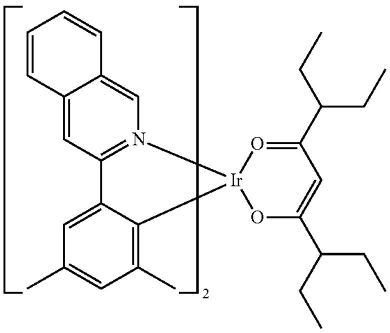

,

-continued

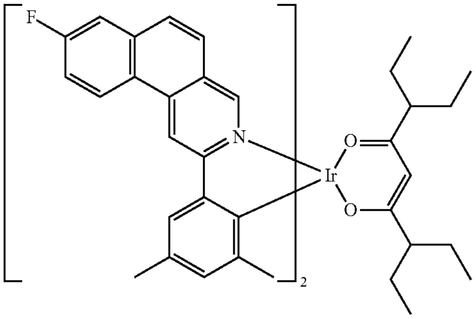

, and

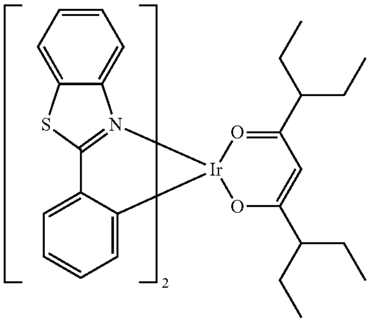

.

According to another embodiment of the present disclosure, further disclosed is a display assembly comprising an electroluminescent device whose specific structure is represented by any one of the preceding embodiments.

Combination with Other Materials

The materials described in the present disclosure for a particular layer in an organic light emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, materials disclosed herein may be used in combination with a wide variety of emissive dopants, hosts, transporting layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

Compound Synthesis

Synthesis Example 1: Synthesis of Compound 1-89

Step 1: Synthesis of Intermediate 3

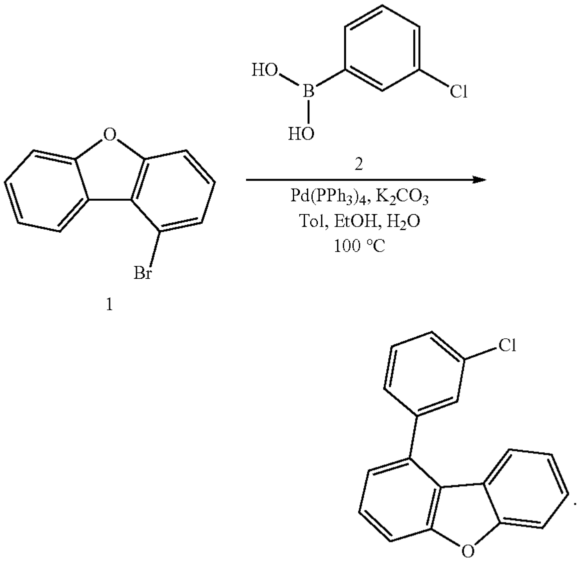

1

3

Under nitrogen protection, Intermediate 1 (5 g, 20.2 mmol), Intermediate 2 (3.5 g, 22.3 mmol), tetrakis(triphenylphosphine)palladium (230 mg, 0.2 mmol), potassium carbonate (5.6 g, 40.4 mmol), toluene (Tol, 50 mL), ethanol (50 mL), and water (20 mL) were added to a three-necked flask and reacted at 100° C. for 16 hours. After the reaction was complete, the reaction solution was cooled to room temperature, distilled water was added, and the mixture was extracted with ethyl acetate. The organic phases were washed with water and concentrated to remove the solvent, and the crude product was purified by column chromatography (PE/DCM=10/1) to give 5 g of Intermediate 3 as a white solid (yield: 89%).

Step 2: Synthesis of Compound 1-89

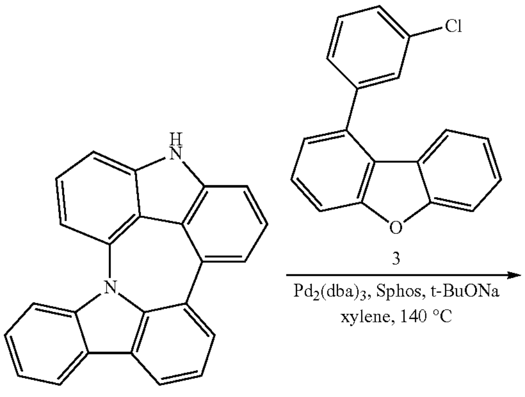

4

-continued

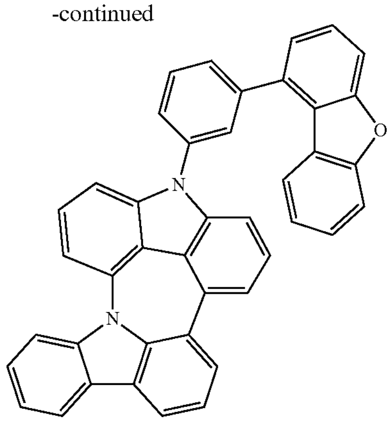

Compound 1-89

Under nitrogen protection, Intermediate 3 (1.85 g, 6.66 mmol), Intermediate 4 (2 g, 6.06 mmol), tris(dibenzylideneacetone)dipalladium (54 mg, 0.06 mmol), 2-dicyclohexylphosphino-2',6'-dimethoxybiphenyl (50 mg, 0.12 mmol), sodium tert-butoxide (1.2 g, 13.3 mmol), and xylene (80 mL) were added to a three-necked flask and reacted at 140° C. for 16 hours. After the reaction was complete, the reaction solution was cooled to room temperature, distilled water was added, and the mixture was extracted with ethyl acetate. The organic phases were washed with water and concentrated to remove the solvent, and the crude product was purified by column chromatography (PE/DCM=6/1) to give 2 g of Compound 1-89 as a yellow solid (yield: 59%). The product was confirmed as the target product with a molecular weight of 572.2.

The present disclosure does not limit the preparation methods of the selected first compound and the second compound, and the persons skilled in the art can prepare the two compounds by conventional synthesis methods, or refer to the above-mentioned synthesis method of compound 1-89, or refer to patent applications such as $US20180337340A_1$, CN111868210A, CN202010270250.2, CN202010285016.7, CN202010268985.1, CN202010285026.0, CN202010720191.4, CN202010825242.X, etc. The preparation method of the organic electroluminescent device is not limited, and the preparation methods in the following examples are just illustrative and should not be construed as the limitation. The persons skilled in the art can make reasonable improvements on the preparation methods in the following examples based on the related art. For example, the ratio of the first compound to the second compound is not particularly limited, and the persons skilled in the art can make reasonable selections within a certain range according to the related art. For example, based on the total weight of the emissive layer material, the total weight of the first compound and the second compound accounts for 99.5% to 80.0% of the total weight of the emissive layer, and the weight ratio of the first compound to the second compound is between 1:99 to 99:1; or the weight ratio of the first compound to the second compound is between 20:80 to 99:1; or the weight ratio of the first compound to the second compound is between 50:50 to 90:10. In the device examples, devices were tested for properties using conventional equipment in the art (including, but not limited to, evaporator produced by ANG- STROM ENGINEERING, optical measurement system and lifetime test system produced by SUZHOU F STAR, ellipsometer manufactured by BEIJING ELLITOP SCIENTIFIC CO., LTD., etc.) by methods well known to the persons skilled in the art. Since the persons skilled in the art are aware of the related content of the use of the above-mentioned equipment and the test methods, the inherent data of the samples can be obtained with certainty and without any influence, and the above-mentioned related content will not be described in detail in this patent.

DEVICE EXAMPLE

Device Example 1

First, a glass substrate having an Indium Tin Oxide (ITO) anode having a thickness of 120 nm was cleaned and then treated with UV ozone and oxygen plasma. After the treatment, the substrate was dried in a nitrogen-filled glovebox to remove moisture, then mounted on a substrate holder and placed in a vacuum chamber. Organic layers specified below were sequentially deposited by vacuum thermal evaporation on the ITO anode at a rate of 0.01 Å/s to 5 Å/s and at a vacuum degree of about $10^{-8}$ torr. Compound HI was used as a hole injection layer (HIL) with a thickness of 100 Å. Compound HT was used as a hole transport layer (HTL) with a thickness of 400 Å. Compound EB was used as an electron blocking layer (EBL) with a thickness of 50 Å. Then, Compound 1-107 as a first host, Compound 2-25 as a second host, and phosphorescent compound RD (whose weight accounted for 2% of the total weight of the emissive layer) were co-deposited as an emissive layer (EML) with a thickness of 400 Å. Compound HB was used as a hole blocking layer (HBL) with a thickness of 50 Å. On the hole blocking layer, Compound ET and 8-hydroxyquinolinolato-lithium (Liq) were co-deposited as an electron transport layer (ETL) with a thickness of 350 Å. Finally, 8-hydroxyquinolinolato-lithium (Liq) with a thickness of 10 Å was deposited as an electron injection layer (EIL), and $A_1$ with a thickness of 1200A was deposited as a cathode. The device was then transferred back to the glovebox and encapsulated with a glass lid to complete the device.

Device Example 2

The implementation mode in Device Example 2 was the same as the implementation mode in Device Example 1 except that Compound 2-25 was replaced with Compound 2-21 as the second host in the emissive layer (EML).

Device Example 3

The implementation mode in Device Example 3 was the same as the implementation mode in Device Example 1 except that Compound 1-107 was replaced with Compound 1-89 as the first host in the emissive layer (EML) and Compound 2-25 was replaced with Compound 2-107 as the second host (Compound 1-89 and Compound 2-107 were at a weight ratio of 49:49).

Device Example 4

The implementation mode in Device Example 4 was the same as the implementation mode in Device Example 1 except that Compound 2-25 was replaced with Compound 1-89 as the second host in the emissive layer (EML) (Compound 1-107 and Compound 1-89 were at a weight ratio of 88:10).

Device Comparative Example 1

The implementation mode in Device Comparative Example 1 was the same as the implementation mode in Device Example 1 except that Compound 1-107 and Compound 2-25 were replaced with Compound 2-25 as the host in the emissive layer (EML) (Compound 2-25 and Compound RD were at a weight ratio of 98:2).

Device Comparative Example 2

The implementation mode in Device Comparative Example 2 was the same as the implementation mode in Device Comparative Example 1 except that Compound 2-25 was replaced with Compound 1-107 as the host in the emissive layer (EML).

Device Comparative Example 3

The implementation mode in Device Comparative Example 3 was the same as the implementation mode in Device Comparative Example 1 except that Compound 2-25 was replaced with Compound 2-21 as the host in the emissive layer (EML).

Device Comparative Example 4

The implementation mode in Device Comparative Example 4 was the same as the implementation mode in Device Comparative Example 1 except that Compound 2-25 was replaced with Compound 2-107 as the host in the emissive layer (EML).

Detailed structures and thicknesses of layers of the devices are shown in Table 1. The layers using more than one material were obtained by doping different compounds at weight ratios as recorded in the following table.

TABLE 1

Device structures in Device Examples and Device Comparative Examples

| Device ID | HIL | HTL | EBL | EML | HBL | ETL |
|---|---|---|---|---|---|---|
| Example 1 | Compound HI (100 Å) | Compound HT (400 Å) | Compound EB (50 Å) | Compound 1-107:Compound 2-25:Compound RD (68.5:29.5:2) (400 Å) | Compound HB (50 Å) | Compound ET:Liq (40:60) (350 Å) |

TABLE 1-continued

Device structures in Device Examples and Device Comparative Examples

| Device ID | HIL | HTL | EBL | EML | HBL | ETL |
|---|---|---|---|---|---|---|
| Example 2 | Compound HI (100 Å) | Compound HT (400 Å) | Compound EB (50 Å) | Compound 1-107:Compound 2-21:Compound RD (68.5:29.5:2) (400 Å) | Compound HB (50 Å) | Compound ET:Liq (40:60) (350 Å) |
| Example 3 | Compound HI (100 Å) | Compound HT (400 Å) | Compound EB (50 Å) | Compound 1-89:Compound 2-107:Compound RD (49:49:2) (400 Å) | Compound HB (50 Å) | Compound ET:Liq (40:60) (350 Å) |
| Example 4 | Compound HI (100 Å) | Compound HT (400 Å) | Compound EB (50 Å) | Compound 1-107:Compound 1-89:Compound RD (88:10:2) (400 Å) | Compound HB (50 Å) | Compound ET:Liq (40:60) (350 Å) |
| Comparative Example 1 | Compound HI (100 Å) | Compound HT (400 Å) | Compound EB (50 Å) | Compound 2-25:Compound RD (98:2) (400 Å) | Compound HB (50 Å) | Compound ET:Liq (40:60) (350 Å) |
| Comparative Example 2 | Compound HI (100 Å) | Compound HT (400 Å) | Compound EB (50 Å) | Compound 1-107:Compound RD (98:2) (400 Å) | Compound HB (50 Å) | Compound ET:Liq (40:60) (350 Å) |
| Comparative Example 3 | Compound HI (100 Å) | Compound HT (400 Å) | Compound EB (50 Å) | Compound 2-21:Compound RD (98:2) (400 Å) | Compound HB (50 Å) | Compound ET:Liq (40:60) (350 Å) |
| Comparative Example 4 | Compound HI (100 Å) | Compound HT (400 Å) | Compound EB (50 Å) | Compound 2-107:Compound RD (98:2) (400 Å) | Compound HB (50 Å) | Compound ET:Liq (40:60) (350 Å) |

The structures of the materials used in the devices are shown as follows:

Compound HI

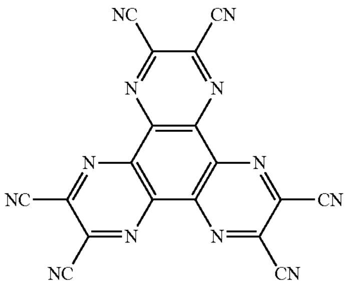

Compound HT

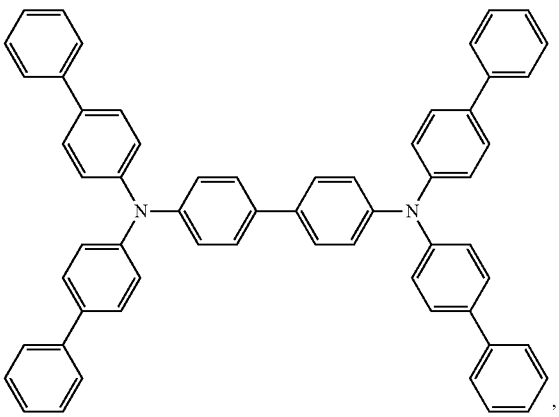
,

-continued

Compound EB

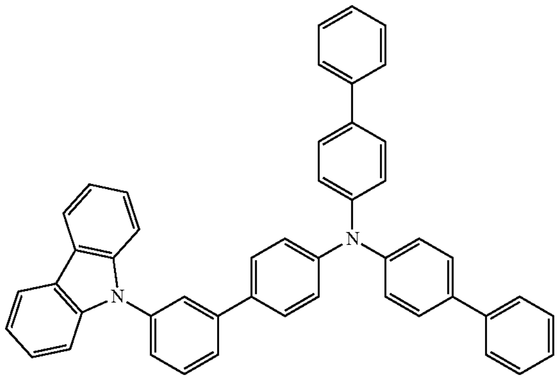
,

Compound RD

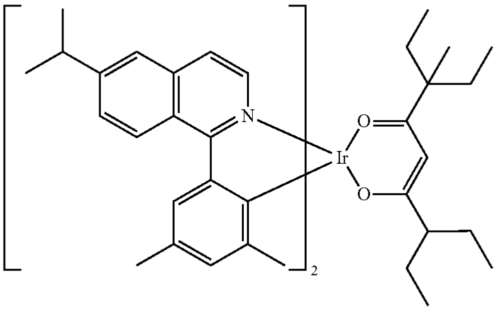
,

-continued

Compound HB

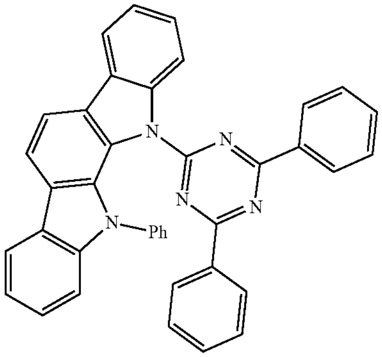

,

Compound ET

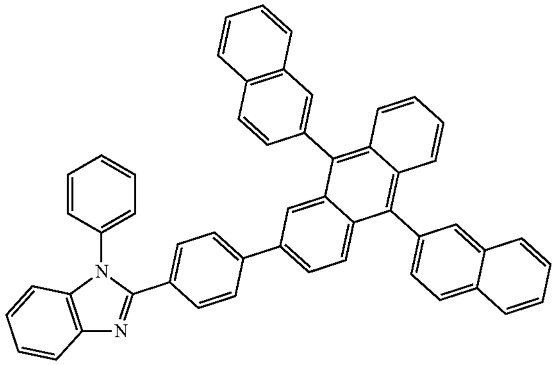

,

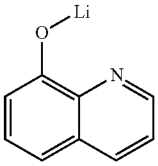

,

Liq

Compound 1-107

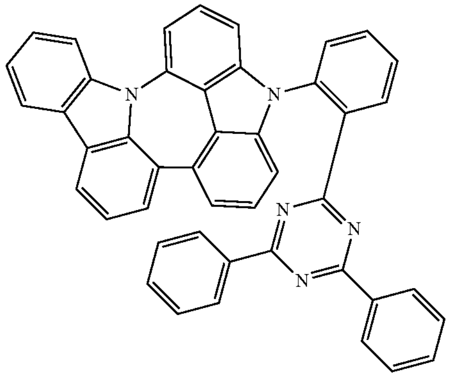

,

Compound 1-89

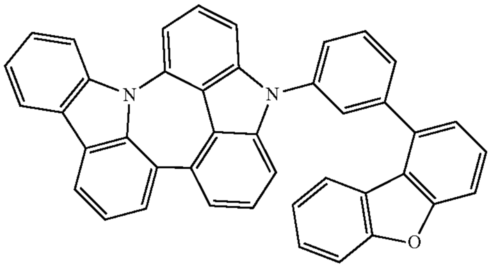

,

-continued

Compound 2-25

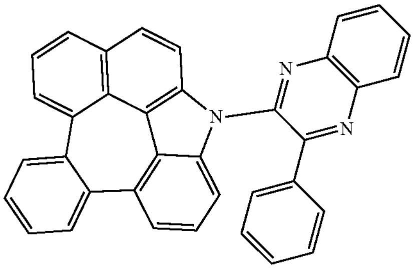

Compound 2-21

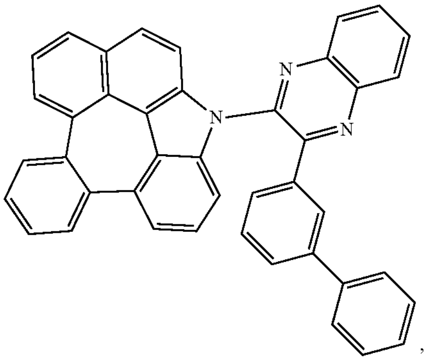

, and

Compound 2-107

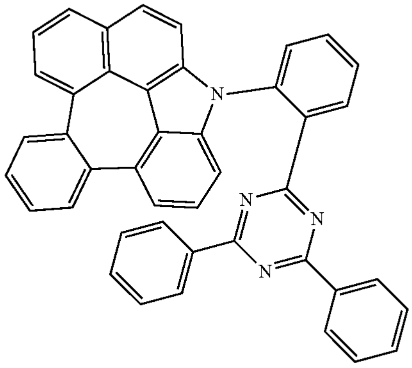

.

The lifetime (LT97) of the device was measured at a constant current of 80 $mA/cm^2$, and LT97 refers to the time required for the brightness of the device to decay to 97% of its initial brightness. The data was recorded and shown in Table 2.

TABLE 2

Device data

| Device ID | At 80 $mA/cm^2$ LT97 (h) |
| --- | --- |
| Example 1 | 102 |
| Example 2 | 136 |
| Example 3 | 166 |
| Example 4 | 124 |
| Comparative Example 1 | 41 |
| Comparative Example 2 | 71 |
| Comparative Example 3 | 42 |
| Comparative Example 4 | 96 |

Discussion

As shown in Table 2, the lifetime of the device in Example 1 was 102 hours, which was 149% and 43.7% higher than the lifetime of the devices in Comparative Examples 1 and 2, respectively; the lifetime of the device in Example 2 was 136 hours, which was 91.5% and 223.8% higher than the lifetime of the devices in Comparative Example 2 and Comparative Example 3, respectively; the lifetime of the device in Example 3 was 166 hours, which was 72.9% higher than the lifetime of the device in Comparative Example 4; the lifetime of the device in Example 4 was 124 hours, which was 74.6% higher than the lifetime of the device in Comparative Example 2. These data prove that the combination of the first compound and the second compound of the present disclosure, when used as the host material, can greatly improve the lifetime of the device and enable the device to have more excellent performance. It is fully proved that the compound combination of the first compound and the second compound of the present disclosure has a very good application prospect.

It is to be understood that various embodiments described herein are merely illustrative and not intended to limit the scope of the present disclosure. Therefore, it is apparent to the persons skilled in the art that the present disclosure as claimed may include variations of specific embodiments and preferred embodiments described herein. Many of the materials and structures described herein may be replaced with other materials and structures without departing from the spirit of the present disclosure. It is to be understood that various theories as to why the present disclosure works are not intended to be limiting.

The invention claimed is:

1. An electroluminescent device, comprising:

an anode, a cathode, and an organic layer disposed between the anode and the cathode, wherein the organic layer comprises at least a first compound and a second compound; the first compound and the second compound are different;

the first compound has a structure of $H_1$-$L_1$-$Ar_1$; wherein the $H_1$ has a structure represented by Formula 1-a:

Formula 1-a

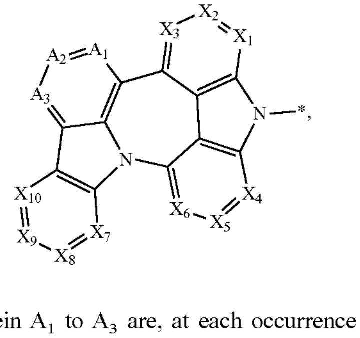

wherein $A_1$ to $A_3$ are, at each occurrence identically or differently, selected from N or CR, and $X_1$ to $X_{10}$ are, at each occurrence identically or differently, selected from N or $CR_x$;

$R_x$ represents, at each occurrence identically or differently, mono-substitution, multiple substitutions or non-substitution;

adjacent substituents R, $R_x$ can be optionally joined to form a ring;

$L_1$ is selected from a single bond, substituted or unsubstituted arylene having 6 to 30 carbon atoms, substituted or unsubstituted heteroarylene having 3 to 30 carbon atoms or combinations thereof;

$Ar_1$ is selected from substituted or unsubstituted aryl having 6 to 30 carbon atoms or substituted or unsubstituted heteroaryl having 3 to 30 carbon atoms;

the second compound has a structure of $H_2$-$L_2$-$Ar_2$;

wherein the $H_2$ has a structure represented by Formula 2-1:

Formula 2-1

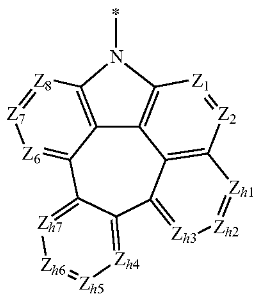

in Formula 2-1, $Z_1$ to $Z_2$ and $Z_6$ to $Z_8$ are, at each occurrence identically or differently, selected from $CR_{z1}$ or N; $Z_{h1}$ to $Z_{h7}$ are, at each occurrence identically or differently, selected from $CR_{zh}$ or N;

$Ar_2$ is selected from substituted or unsubstituted aryl having 6 to 30 carbon atoms or substituted or unsubstituted heteroaryl having 3 to 30 carbon atoms:

$L_2$ is selected from a single bond, substituted or unsubstituted arylene having 6 to 30 carbon atoms, substituted or unsubstituted heteroarylene having 3 to 30 carbon atoms or combinations thereof;

R, $R_x$, $R_{z1}$, and $R_{zh}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof, adjacent substituents $R_{z1}$, $R_{zh}$ can be optionally joined to form a ring.

2. The electroluminescent device of claim 1, wherein $H_1$ has a structure represented by Formula 1-a:

Formula 1-a

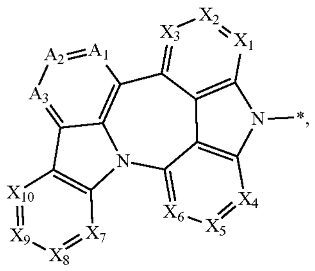

wherein $A_1$ to $A_3$ are, at each occurrence identically or differently, selected from N or CR, and $X_1$ to $X_{10}$ are, at each occurrence identically or differently, selected from N or $CR_x$;

R and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, an isocyano group, a hydroxyl group, a sulfanyl group, and combinations thereof, adjacent substituents R, $R_x$ can be optionally joined to form a ring.

3. The electroluminescent device of claim 1, wherein at least one of R and $R_x$ is selected from deuterium, substituted or unsubstituted aryl having 6 to 30 carbon atoms or substituted or unsubstituted heteroaryl having 3 to 30 carbon atoms.

4. The electroluminescent device of claim 2, wherein at least one of groups of adjacent substituents: adjacent substituents R in $A_1$ to $A_3$, adjacent substituents $R_x$ in $X_1$ to $X_3$, adjacent substituents $R_x$ in $X_4$ to $X_6$ or adjacent substituents $R_x$ in $X_7$ to $X_{10}$ is joined to form a ring.

5. The electroluminescent device of claim 1, wherein the $H_1$ is selected from the group consisting of the following structures:

H-1

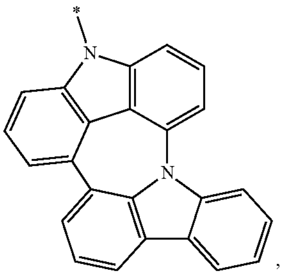

,

-continued

H-2

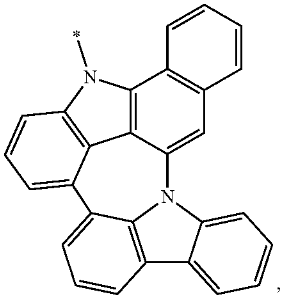

,

H-3

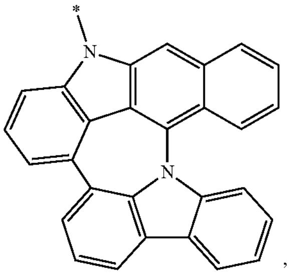

,

H-4

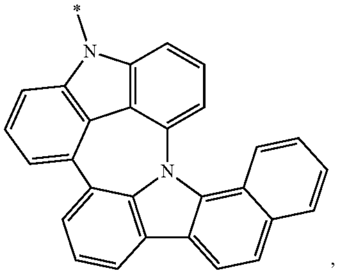

,

H-5

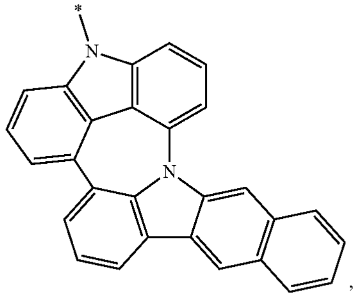

,

H-6

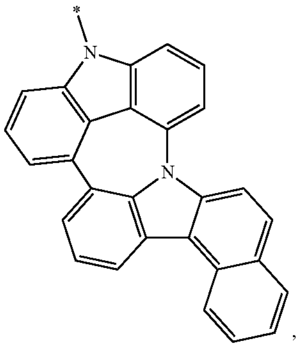

,

-continued
H-7
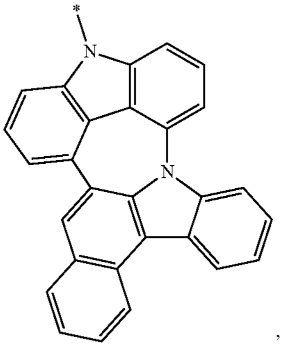
,
H-8
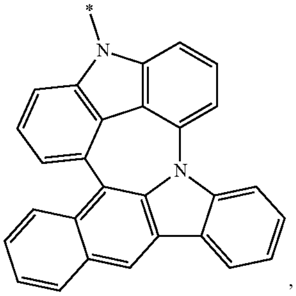
,
H-9
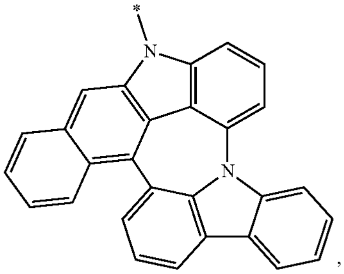
,
H-10
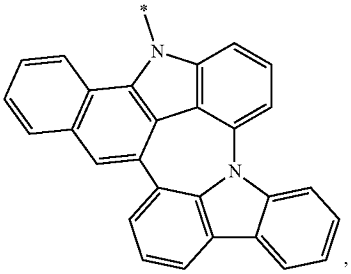
,
H-11
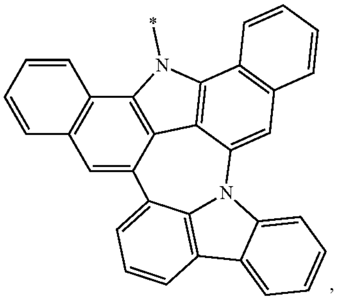
,
-continued
H-12
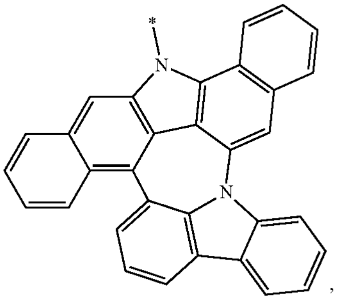
,
H-13
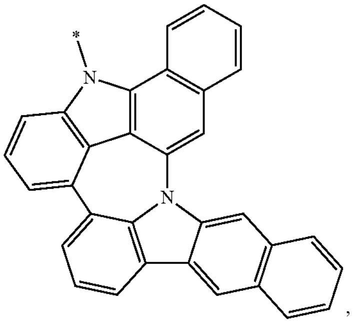
,
H-14
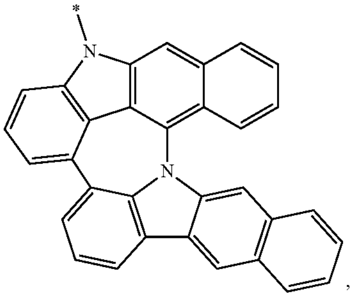
,
H-15
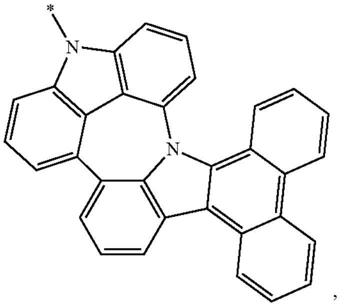
,
H-16
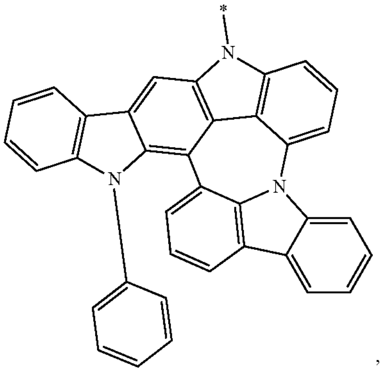
, -continued
H-17
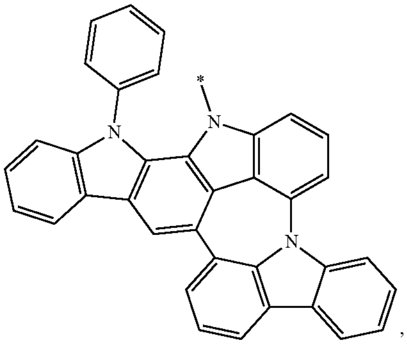
,
H-18
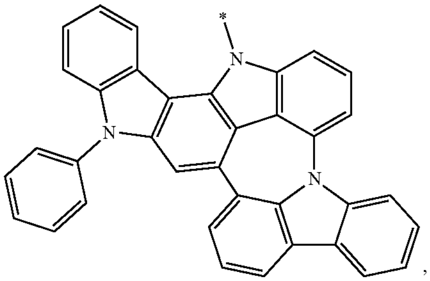
,
H-19
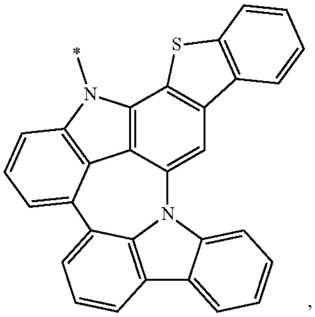
,
H-20
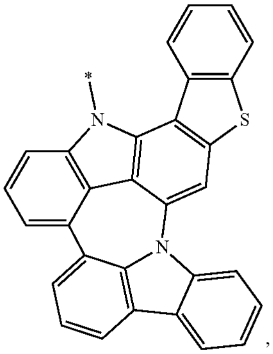
,
H-21
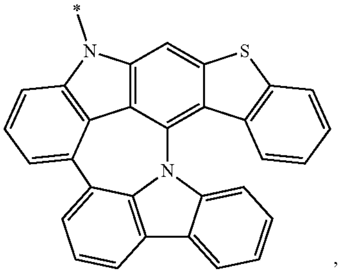
,
-continued
H-22
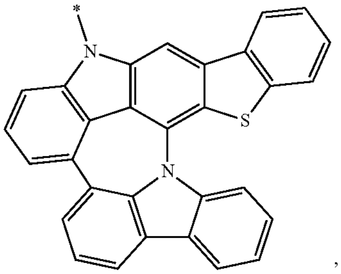
,
H-23
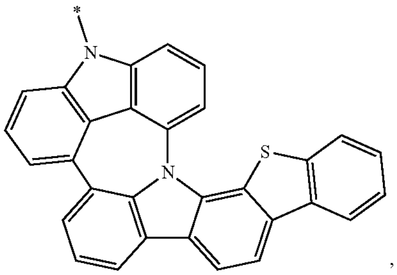
,
H-24
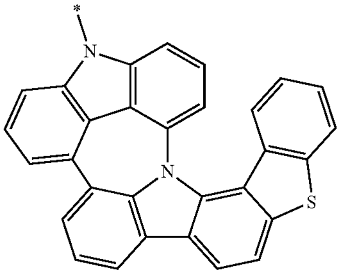
,
H-25
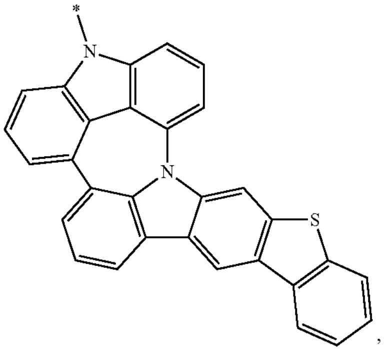
,
H-26
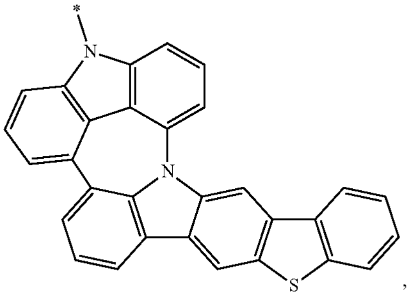
, -continued
H-27
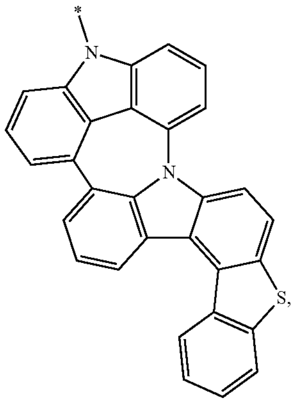
H-28
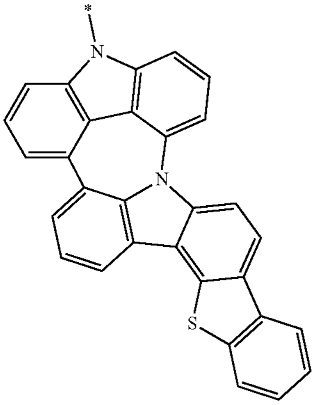
,
H-29
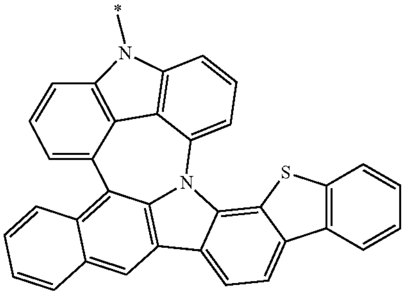
,
H-30
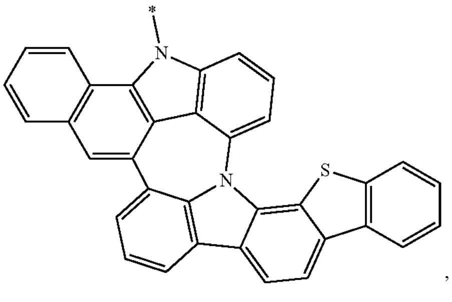
,
-continued
H-31
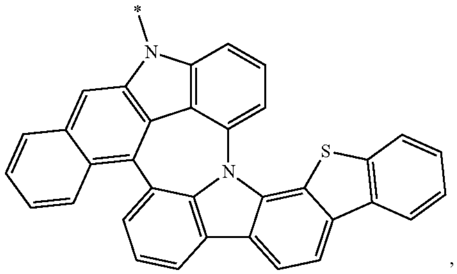
,
H-32
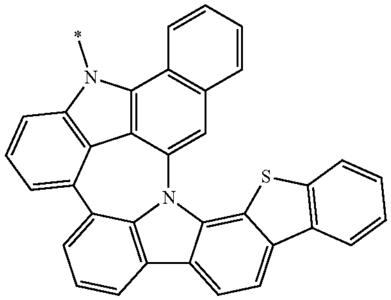
,
H-33
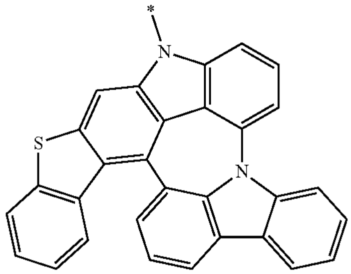
,
H-34
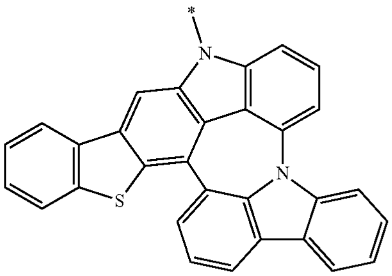
,
H-35
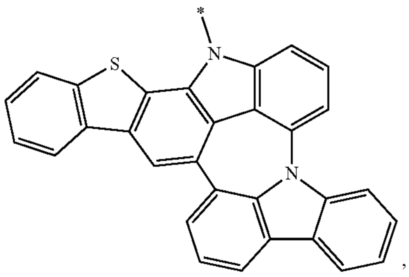
, -continued
H-36
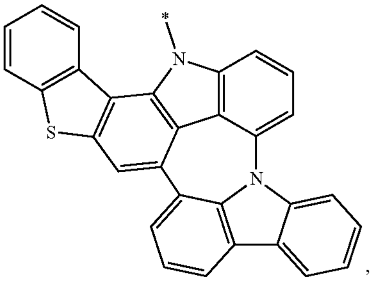
,
H-37
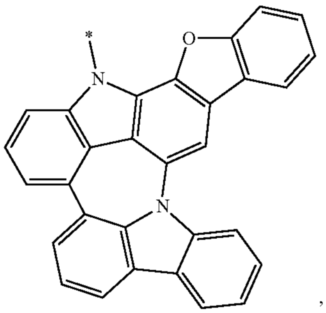
,
H-38
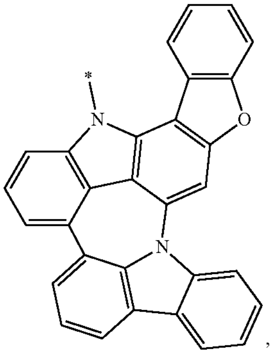
,
H-39
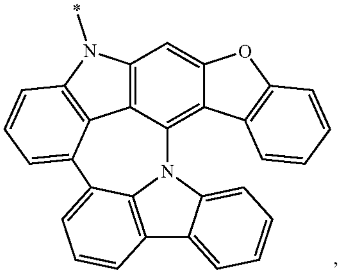
,
H-40
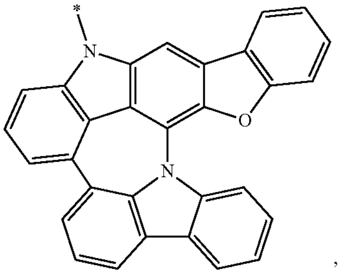
,
-continued
H-41
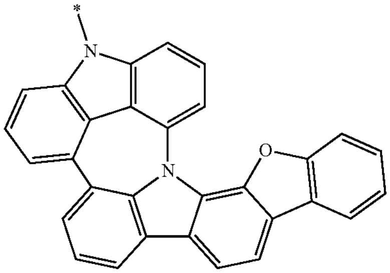
,
H-42
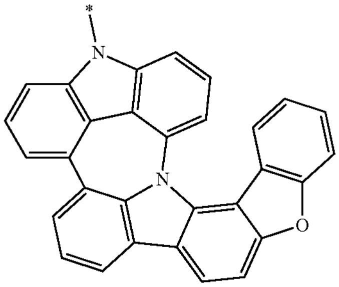
,
H-43
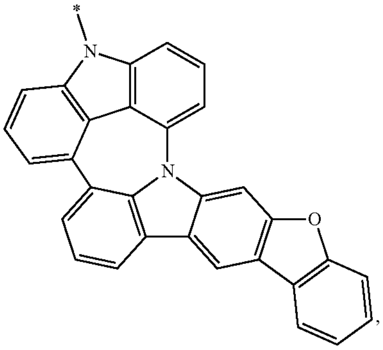
,
H-44
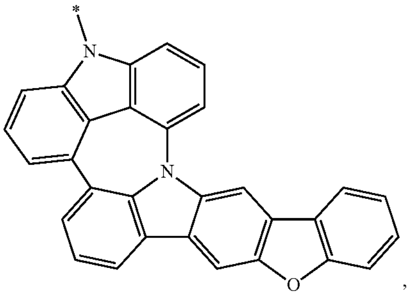
,
H-45
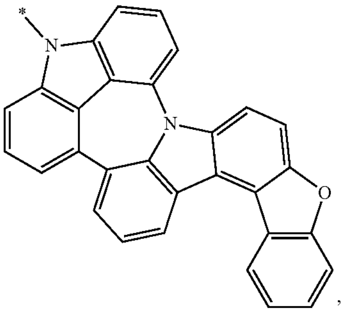
, H-46
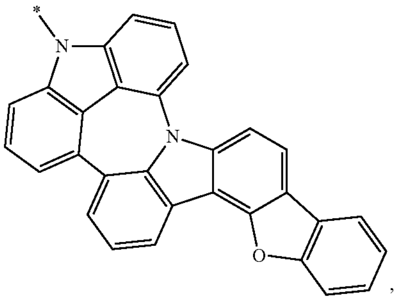
,
H-47
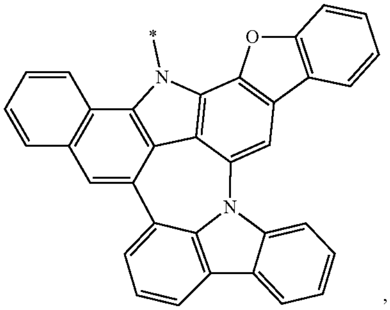
,
H-48
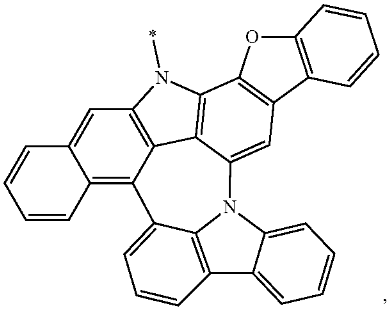
,
H-49
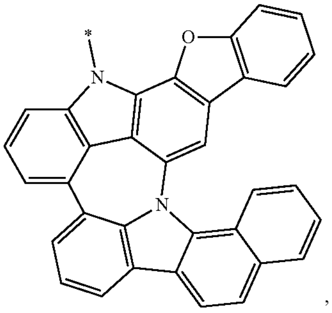
,
H-50
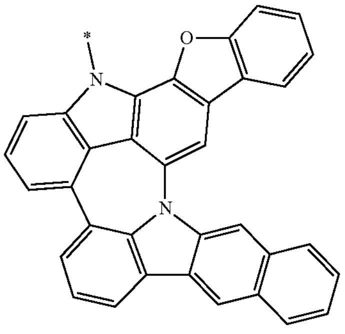
,
H-51
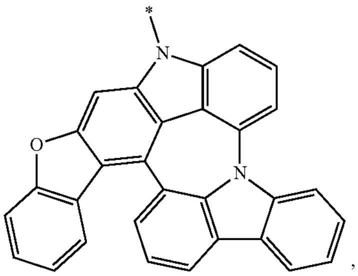
,
H-52
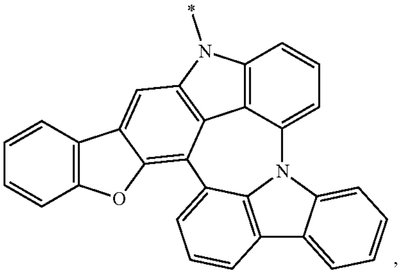
,
H-53
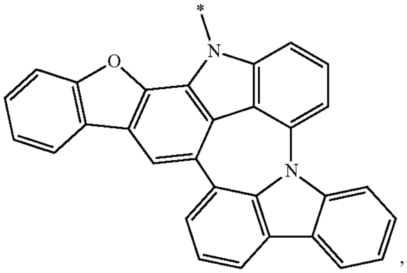
,
H-54
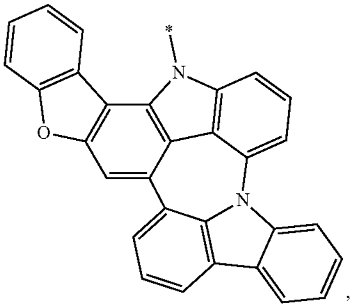
,
H-55
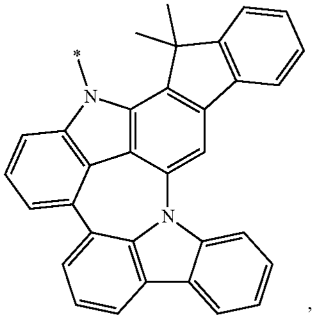
, -continued
H-56
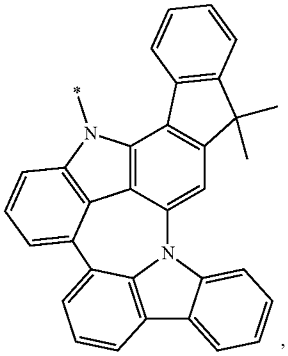
,
H-57
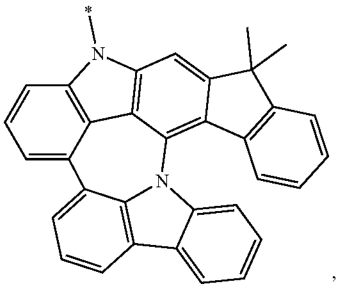
,
H-58
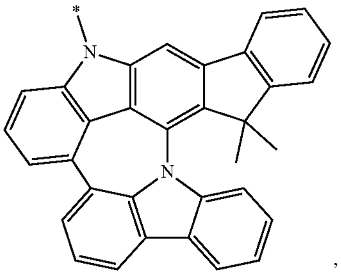
,
H-59
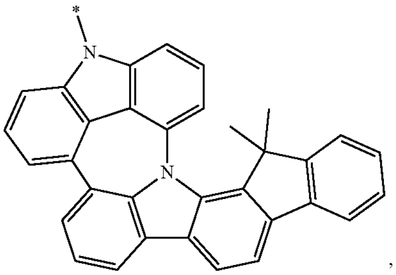
,
H-60
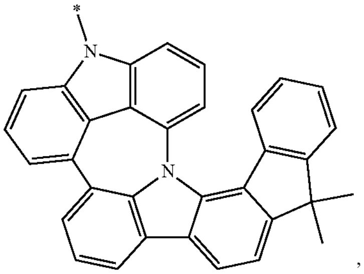
,
-continued
H-61
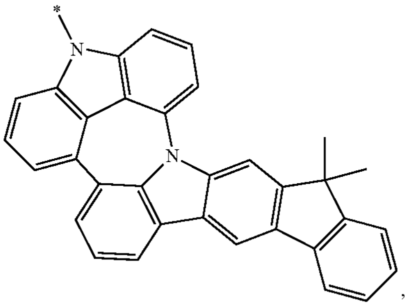
,
H-62
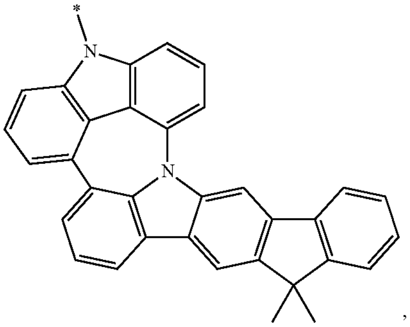
,
H-63
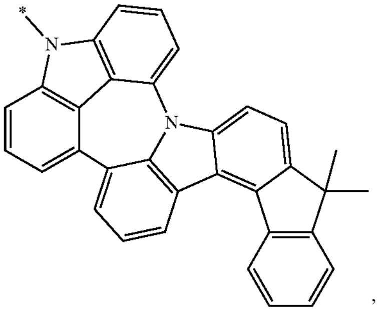
,
H-64
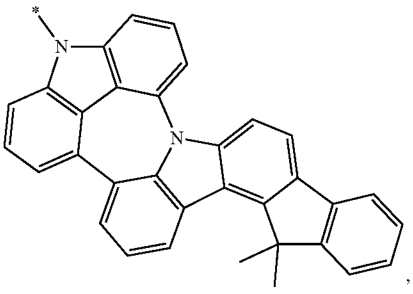
,
H-65
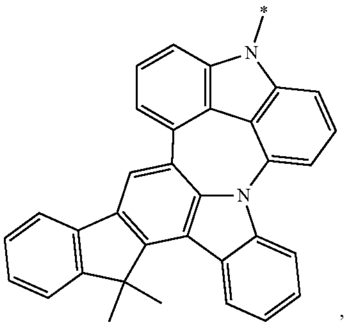
, -continued
H-66
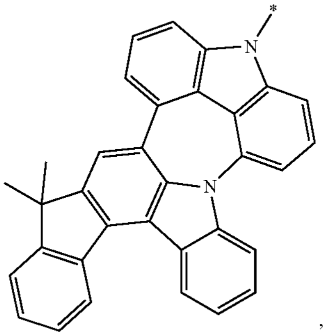
,
H-67
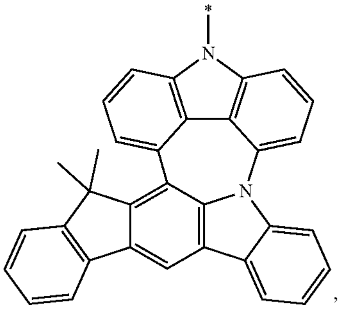
,
H-68
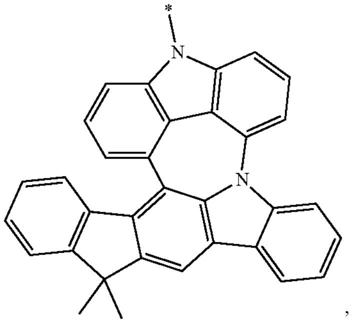
,
H-69
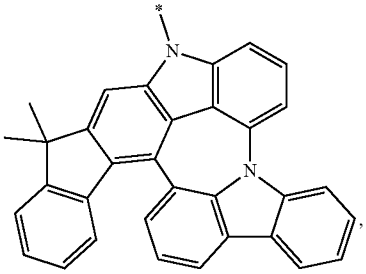
,
H-70
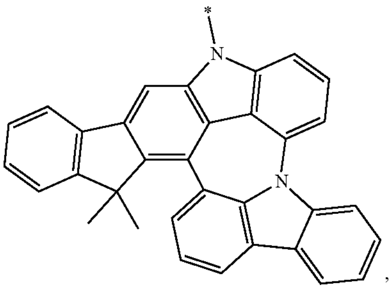
,
H-71
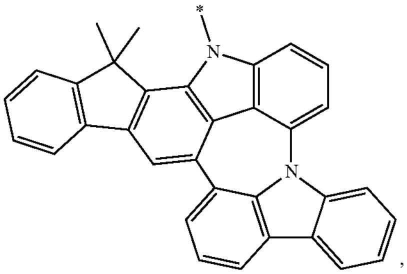
,
H-72
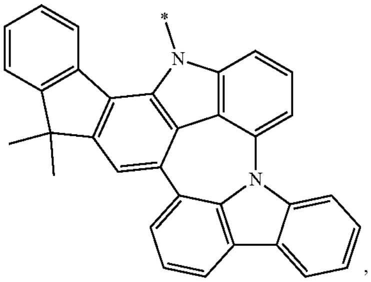
,
H-73
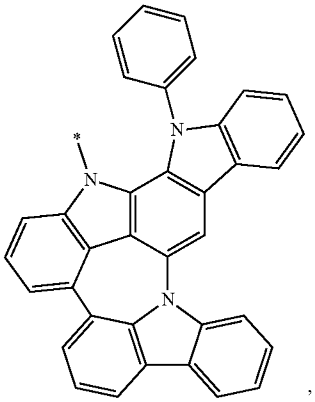
,
H-74
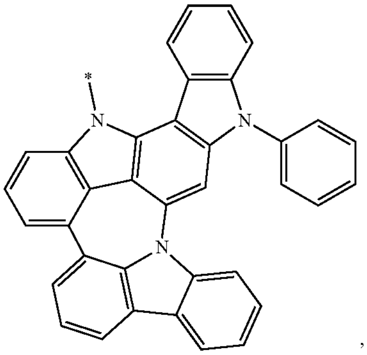
, -continued
H-75
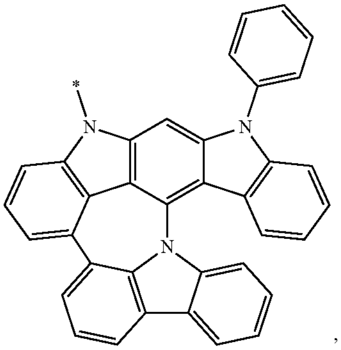
,
H-76
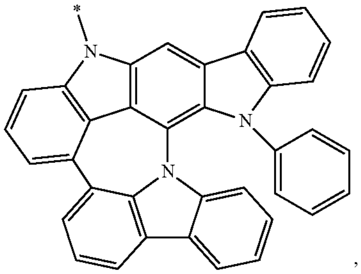
,
H-77
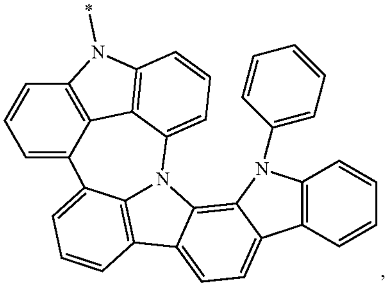
,
H-78
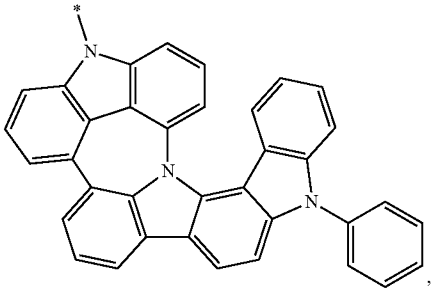
,
H-79
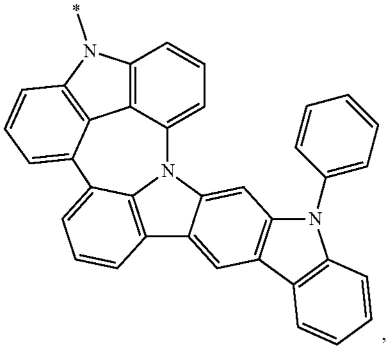
,
-continued
H-80
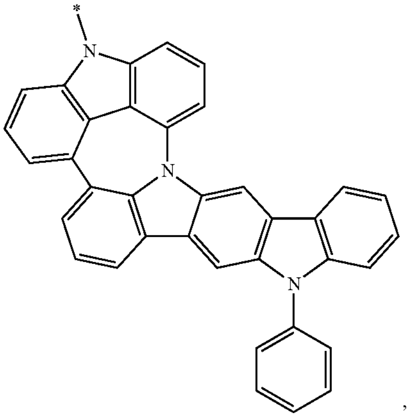
,
H-81
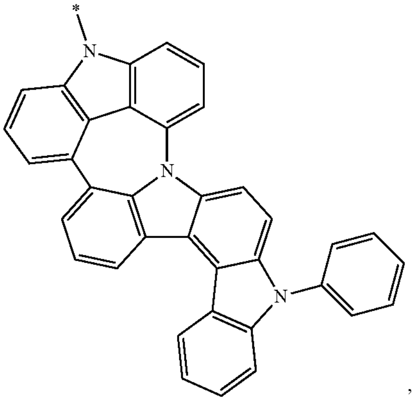
,
H-82
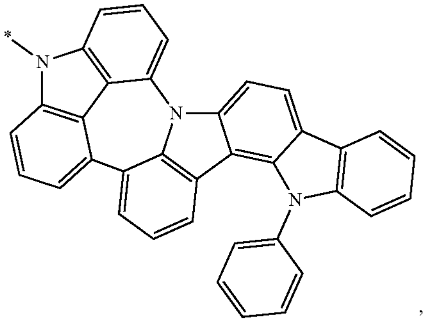
,
H-83
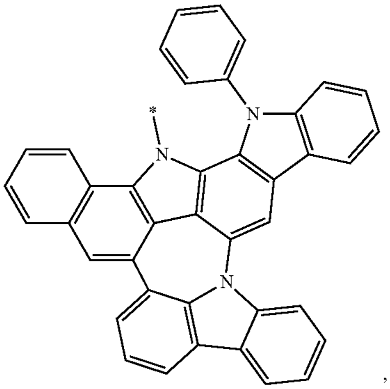
, -continued
H-84
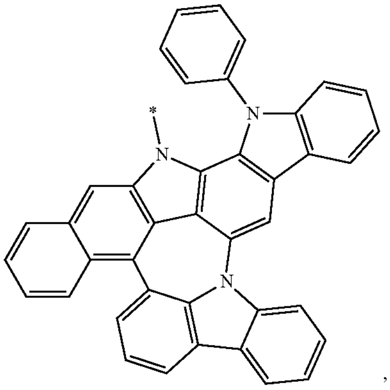
,
H-85
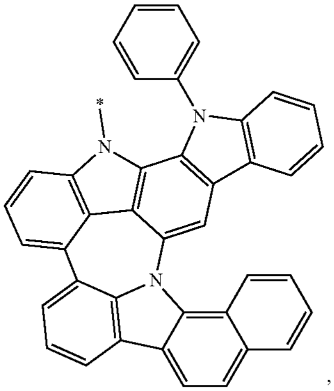
,
H-86
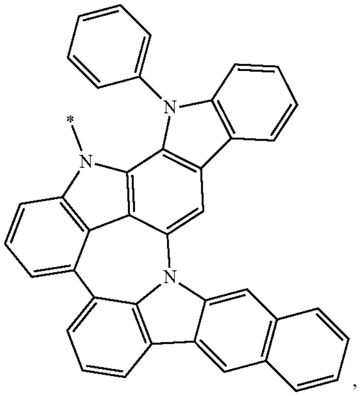
,
H-87
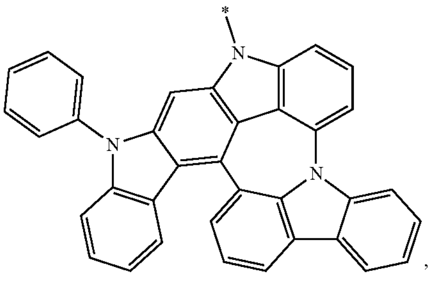
,
-continued
H-88
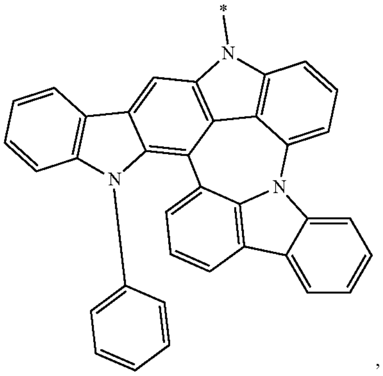
,
H-89
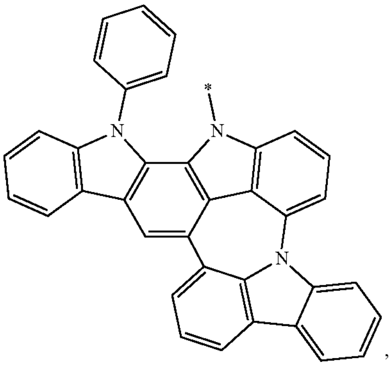
,
H-90
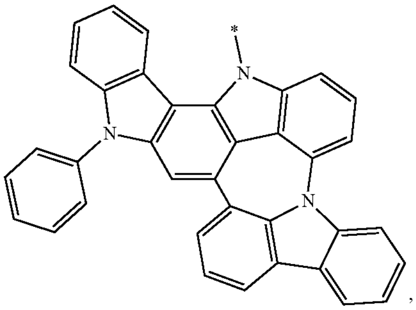
,
H-91
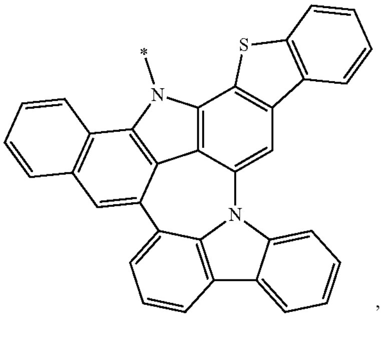
, -continued
H-92
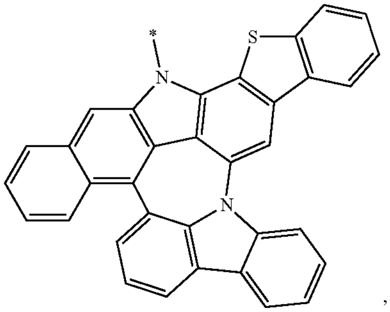,
H-93
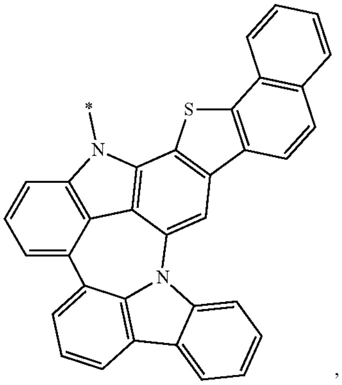,
H-94
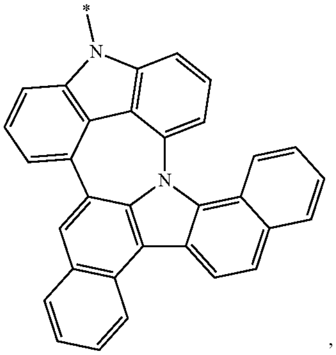,
H-95
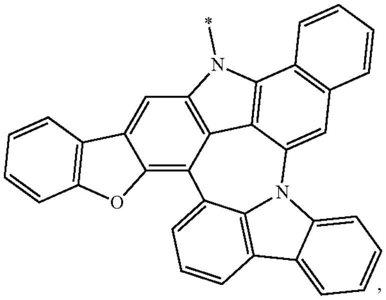,
-continued
H-96
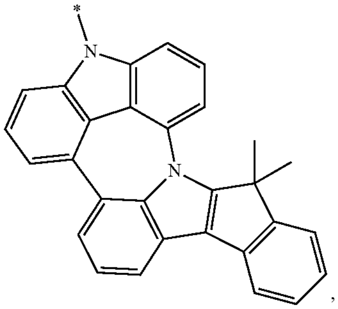,
H-97
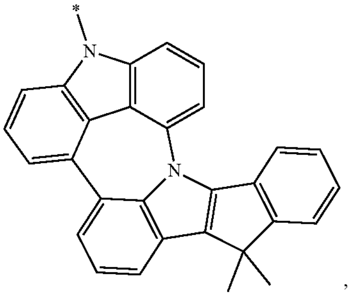,
H-98
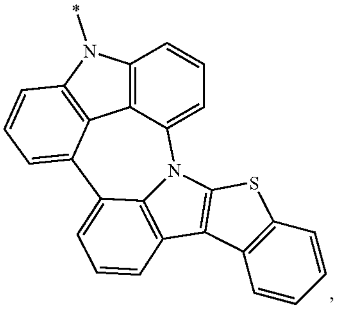,
H-99
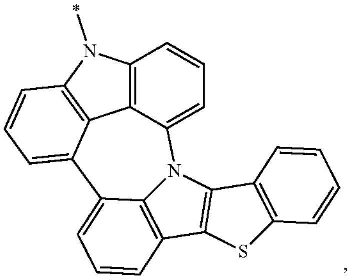,
H-100
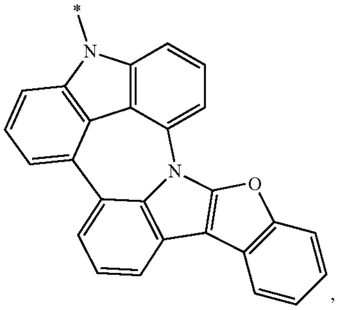, -continued
H-101
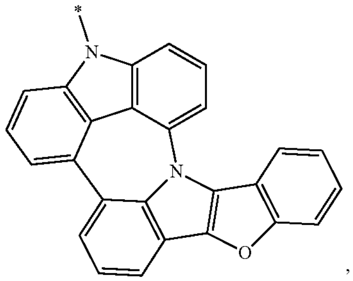
,
H-102
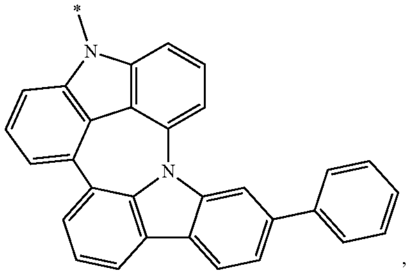
,
H-103
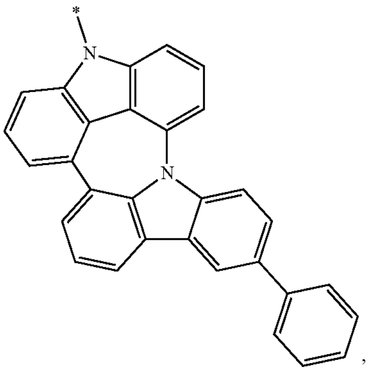
,
H-104
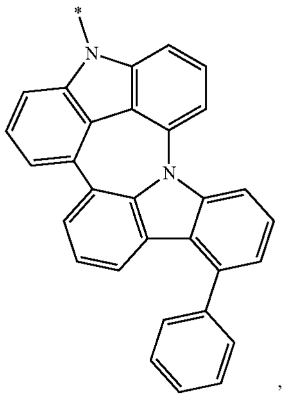
,
-continued
H-105
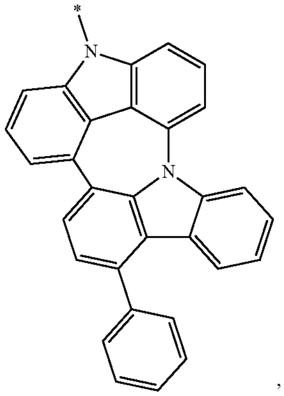
,
H-106
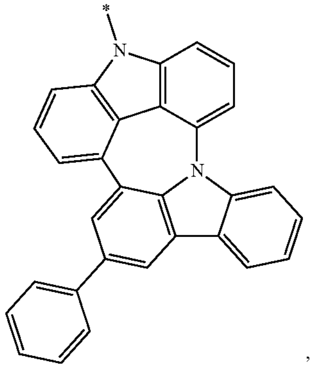
,
H-107
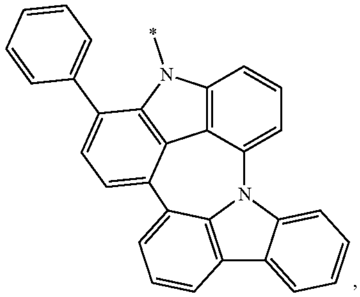
,
H-108
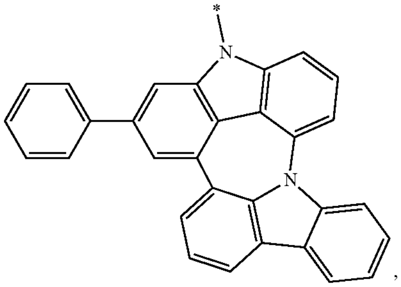
, -continued
H-109
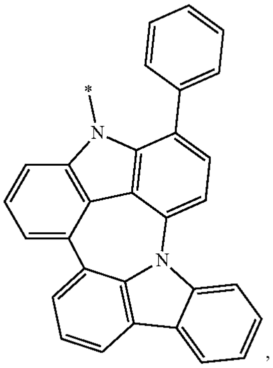
,
H-110
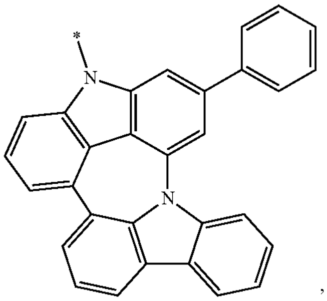
,
H-111
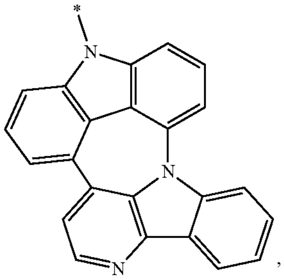
,
H-112
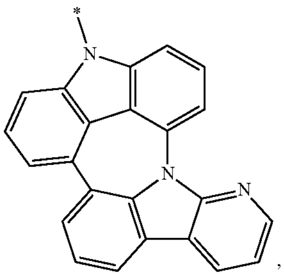
,
H-113
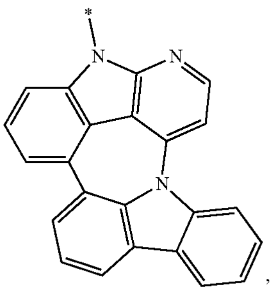
,
-continued
H-114
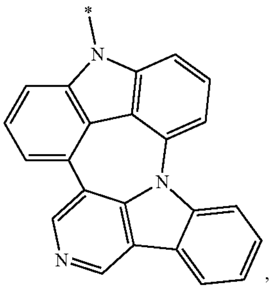
,
H-115
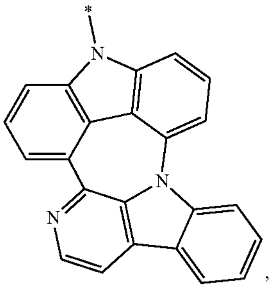
,
H-116
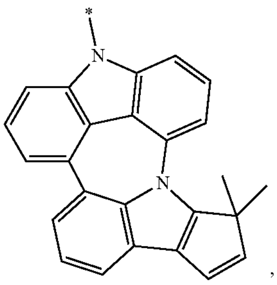
,
H-117
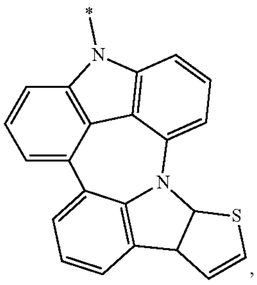
,
H-118
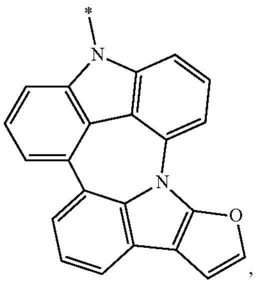
, -continued
H-119
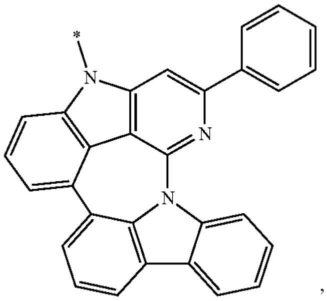
,
H-120
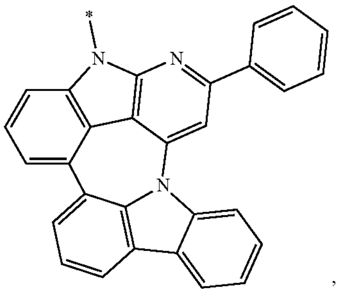
,
H-121
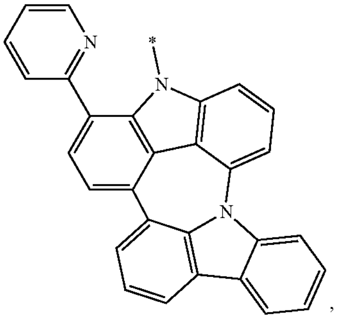
,
H-122
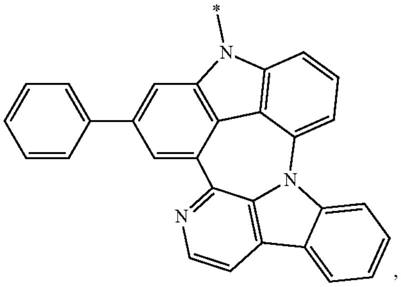
,
H-123
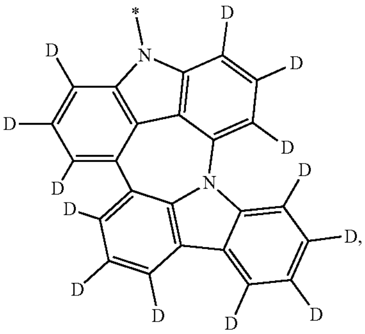
-continued
H-124
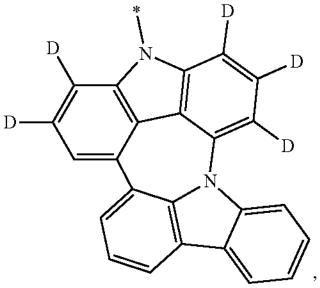
,
H-125
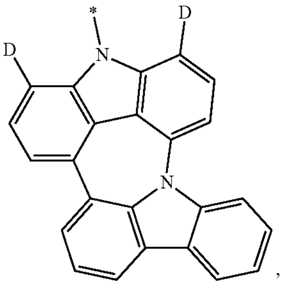
,
H-126
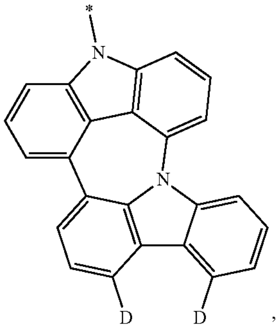
,
H-127
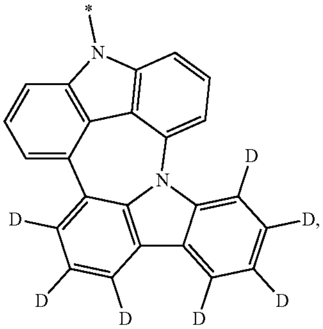
H-128
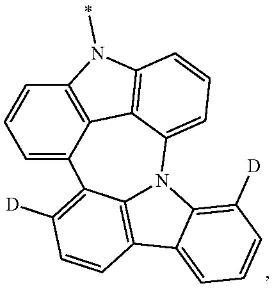
, -continued
H-129
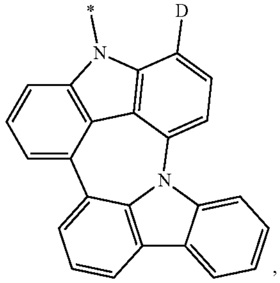
,
H-130
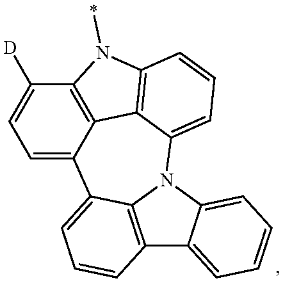
,
H-131
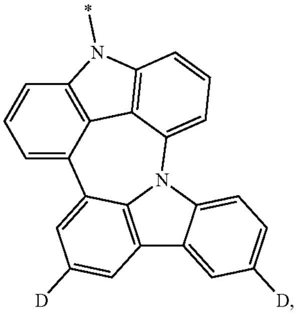
H-132
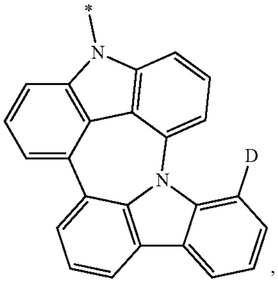
,
H-133
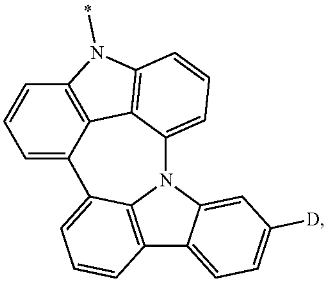
-continued
H-134
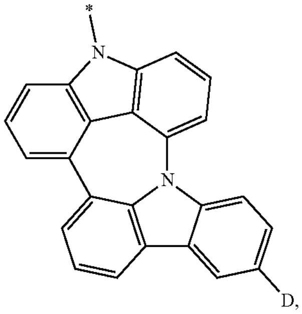
H-135
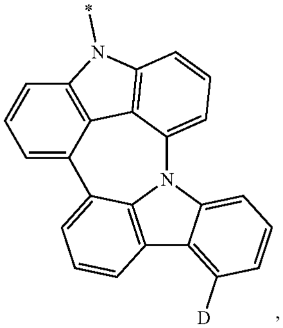
,
H-136
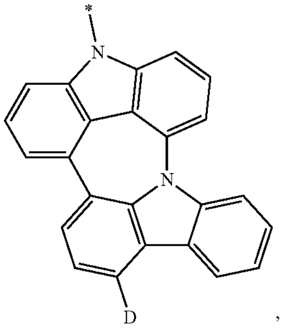
,
H-137
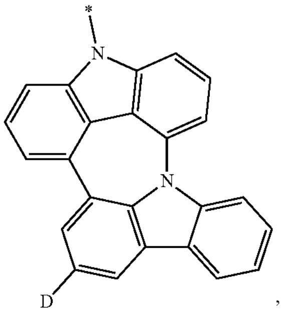
,
H-138
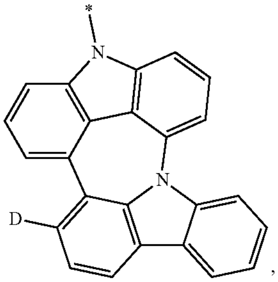
, and -continued

H-139

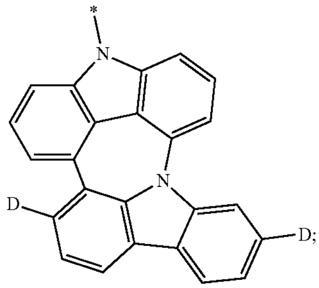;

optionally, hydrogens in the H-1 to H-139 can be partially or completely substituted with deuterium.

6. The electroluminescent device of claim 1, wherein in Formula 2-1, $R_{z1}$ and $R_{zh}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, an isocyano group, a hydroxyl group, a sulfanyl group, and combinations thereof, adjacent substituents $R_{z1}$, $R_{zh}$ can be optionally joined to form a ring.

7. The electroluminescent device of claim 5, wherein the $H_2$ is selected from the following structures:

H2-1

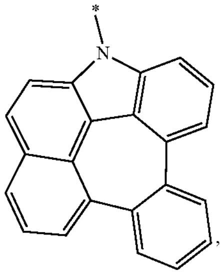,

H2-2

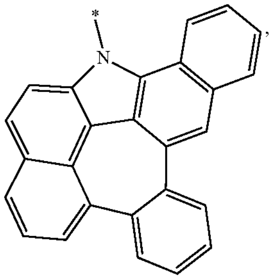,

-continued

H2-3

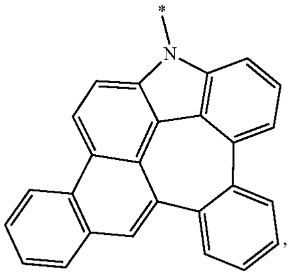,

H2-4

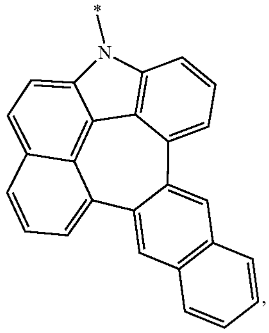,

H2-5

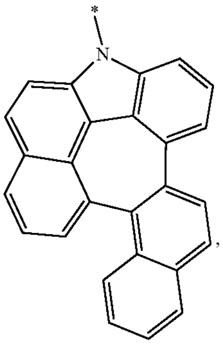,

H2-6

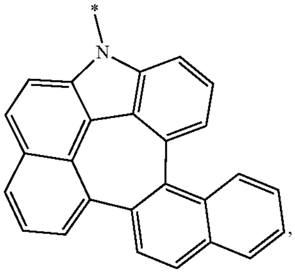,

H2-7

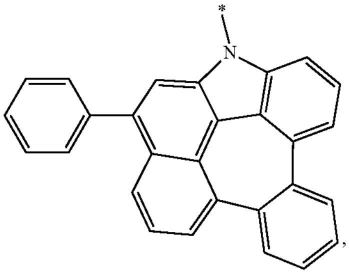,

-continued

H2-8

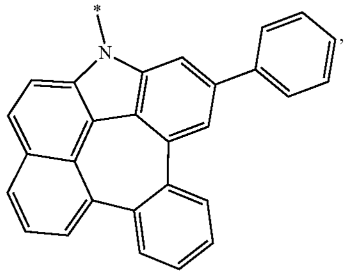

H2-9

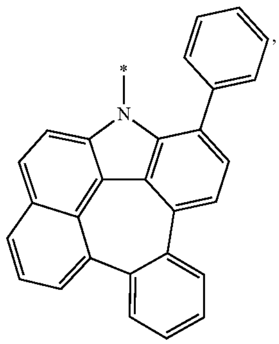

H2-10

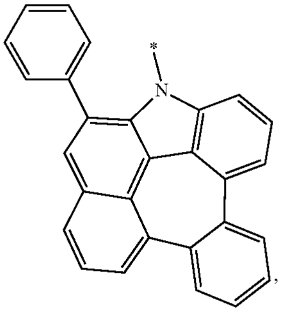

and

H2-11

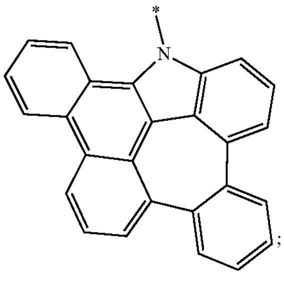

optionally, hydrogens in H2-1 to H2-11 can be partially or completely substituted with deuterium.

8. The electroluminescent device of claim 1, wherein the $Ar_1$ and $Ar_2$ have, at each occurrence identically or differently, a structure represented by any one of the following structures:

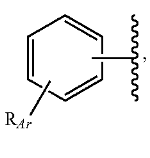

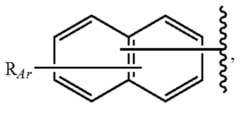

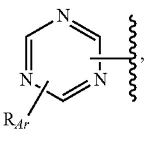

-continued

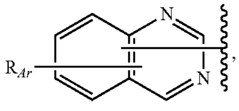

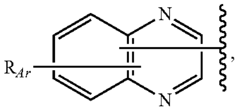

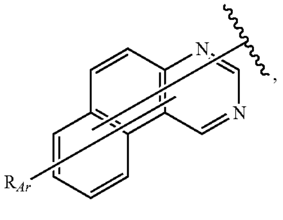

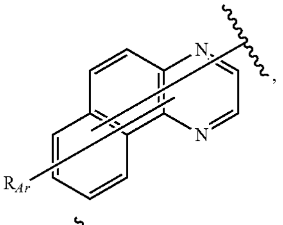

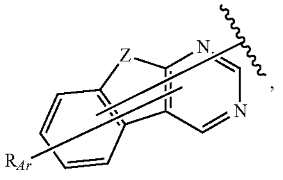

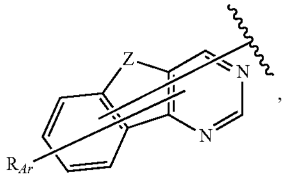

and

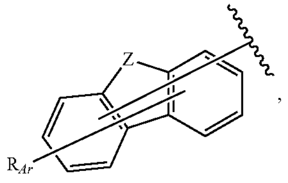

wherein, Z is selected from O, S, $CR_zR_z$, $SiR_zR_z$, $NR_z$, $BR_z$ or $PR_z$; when two $R_z$ exist at the same time, the two $R_z$ can be identical or different;

$R_{Ar}$ represents, at each occurrence identically or differently, mono-substitution, multiple substitutions or non-substitution;

$R_z$ and $R_{Ar}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, an isocyano group, a hydroxyl group, a sulfanyl group, and combinations thereof, adjacent substituents $R_z$, $R_{Ar}$ can be optionally joined to form a ring.

9. The electroluminescent device of claim 7, wherein $Ar_1$ and $Ar_2$ are, at each occurrence identically or differently, selected from the group consisting of following structures:

-continued
Ar-1
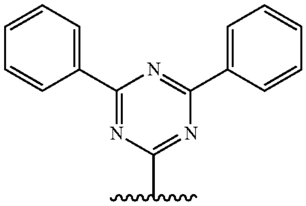
,
Ar-2
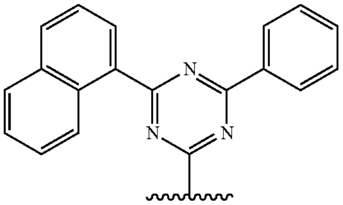
,
Ar-3
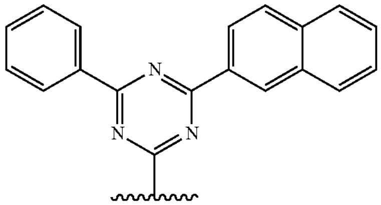
,
Ar-4
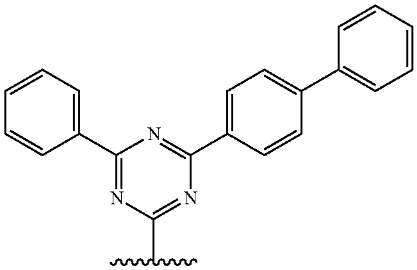
,
Ar-5
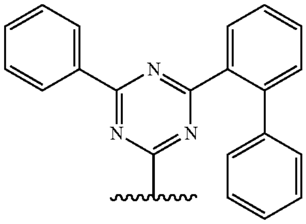
,
Ar-6
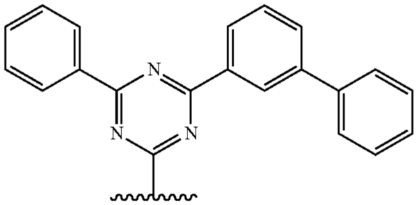
,
Ar-7
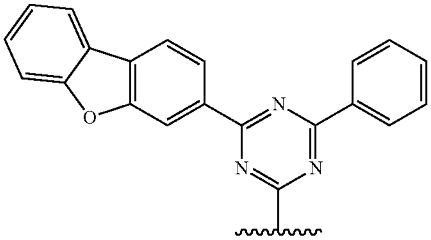
,
Ar-8
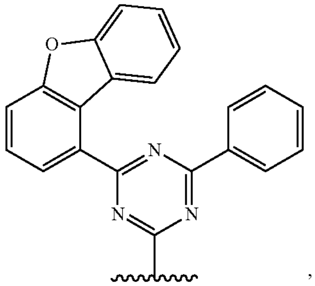
,
Ar-9
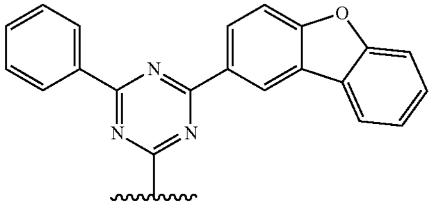
,
Ar-10
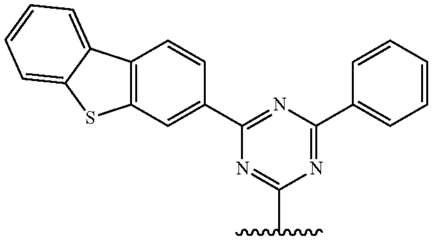
,
Ar-11
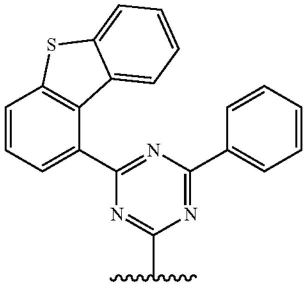
,
Ar-12
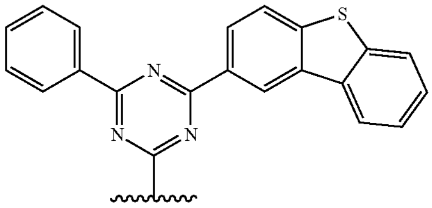
,
Ar-13
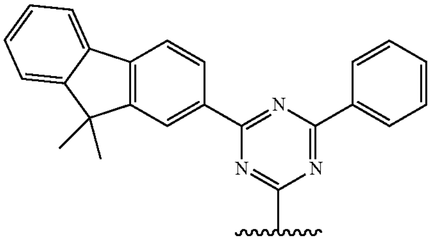
, -continued
Ar-14
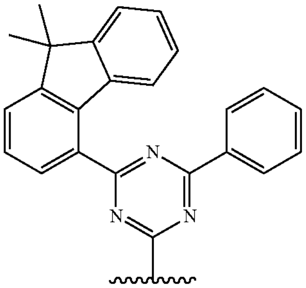
,
Ar-15
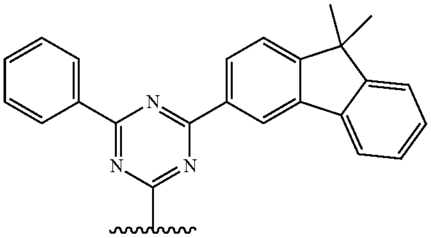
,
Ar-16
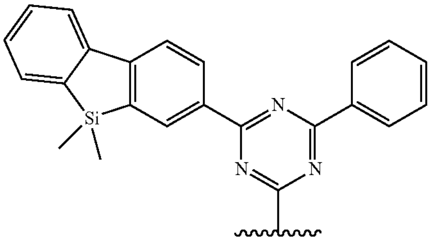
,
Ar-17
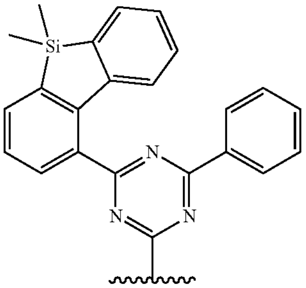
,
Ar-18
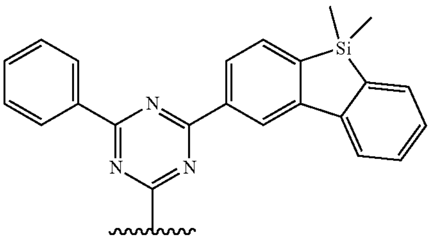
,
Ar-19
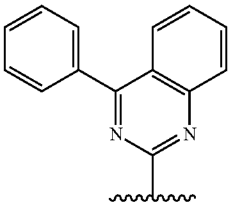
,
-continued
Ar-20
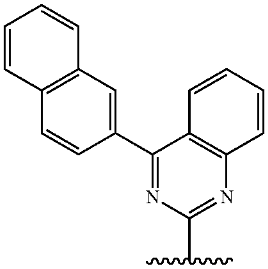
,
Ar-21
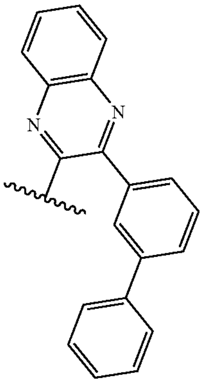
,
Ar-22
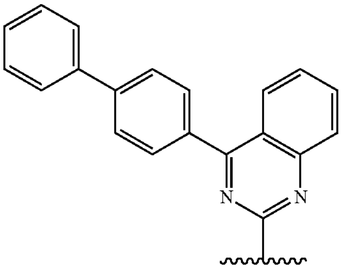
,
Ar-23
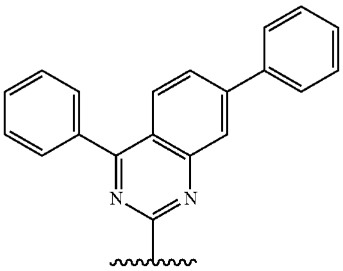
,
Ar-24
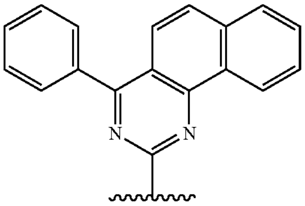
, -continued
Ar-25
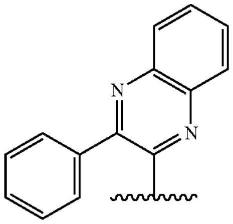
,
Ar-26
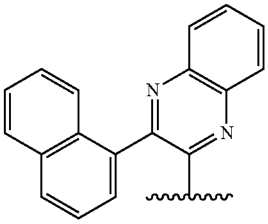
,
Ar-27
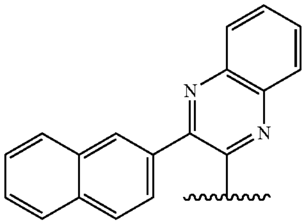
,
Ar-28
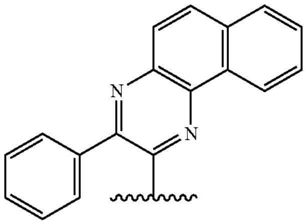
,
Ar-29
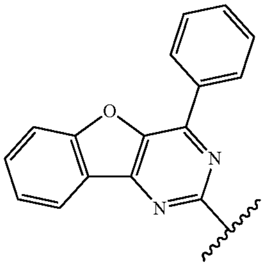
,
Ar-30
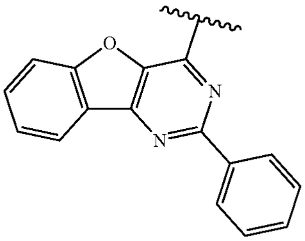
,
-continued
Ar-31
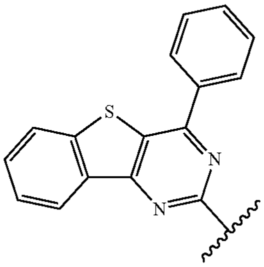
,
Ar-32
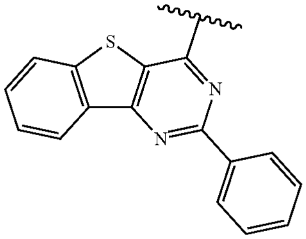
,
Ar-33
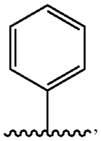
,
Ar-34
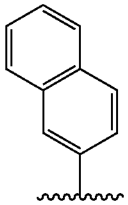
,
Ar-35
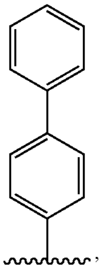
,
Ar-36
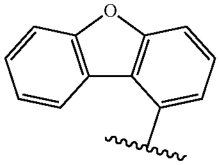
,
Ar-37
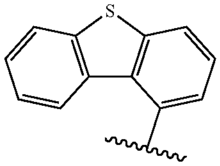
, -continued
Ar-38
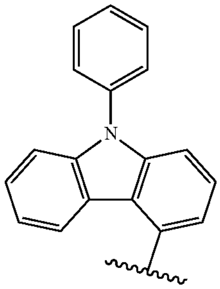
,
Ar-39
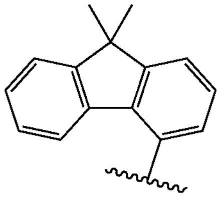
,
Ar-40
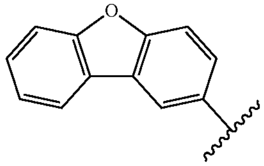
,
Ar-41
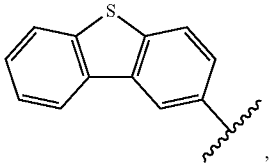
,
Ar-42
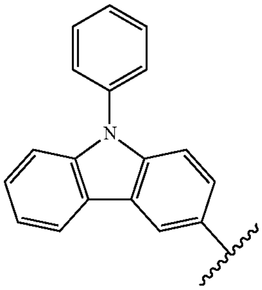
,
Ar-43
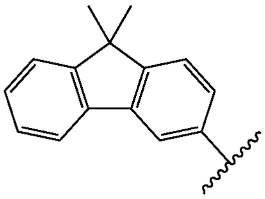
,
Ar-44
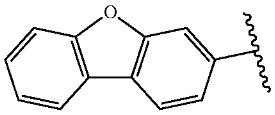
,
Ar-45
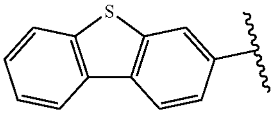
,
-continued
Ar-46
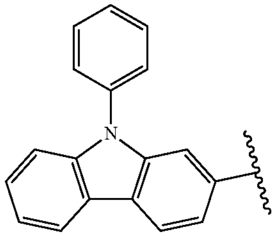
,
Ar-47
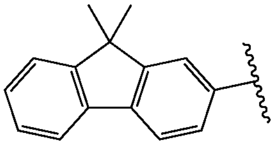
,
Ar-48
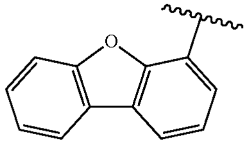
,
Ar-49
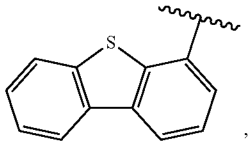
,
Ar-50
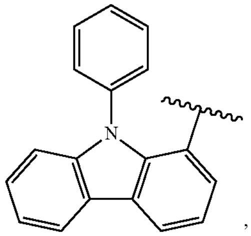
,
Ar-51
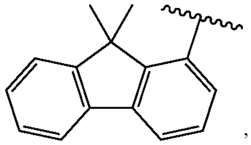
,
Ar-52
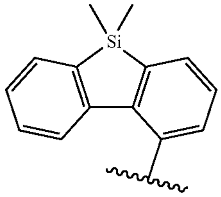
, and
Ar-53
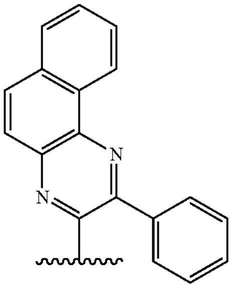
;

optionally, hydrogens in structures of the Ar-1 to Ar-53 can be partially or completely substituted with deuterium.
10. The electroluminescent device of claim 9, wherein $L_1$ and $L_2$ are, at each occurrence identically or differently, selected from the group consisting of the following structures:
L-0
a single bond,
L-1
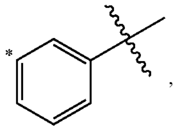
L-2
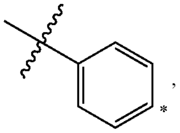
L-3
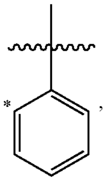
L-4
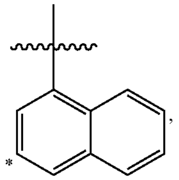
L-5
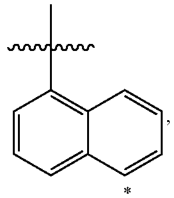
L-6
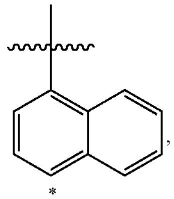
L-7
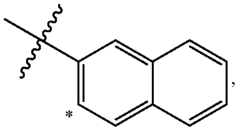
-continued
L-8
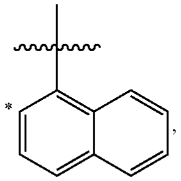
L-9
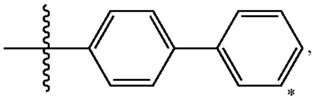
L-10
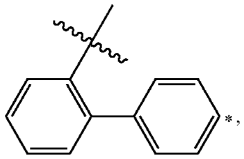
L-11
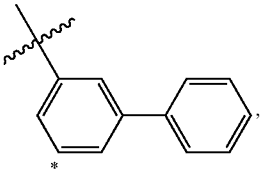
L-12
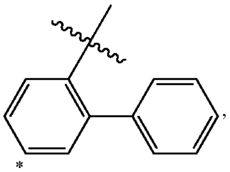
L-13
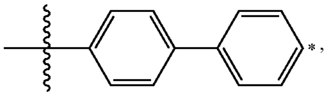
L-14
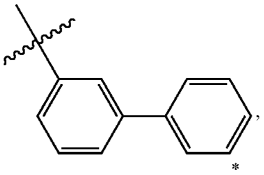
L-15
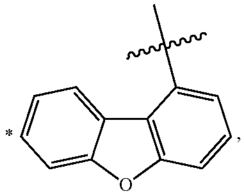
L-16
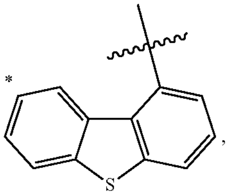

-continued

L-17

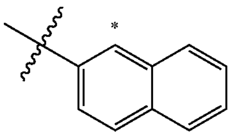,

L-18

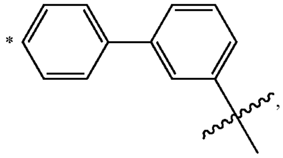,

L-19

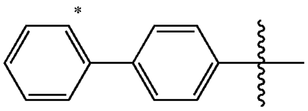,

L-20

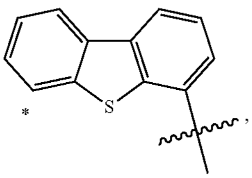,

L-21

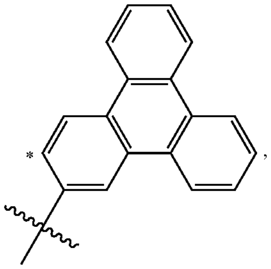,

L-22

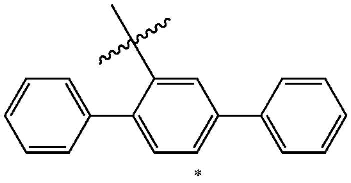,

L-23

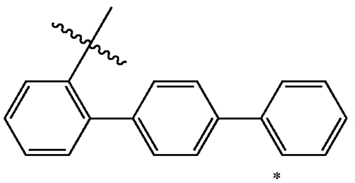,

L-24

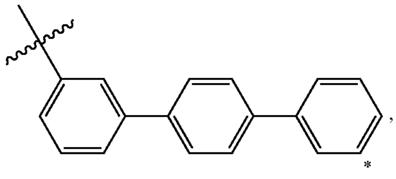,

L-25

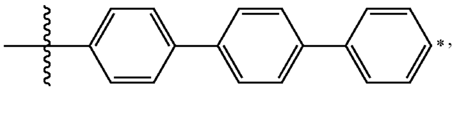,

-continued

L-26

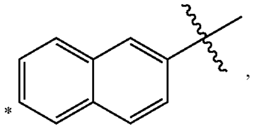, and

L-27

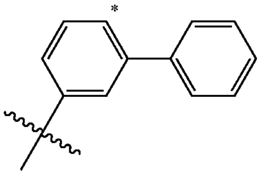;

"*" represents the position at which any of structures L-1 to L-27 is joined to the $H_1$ or the $H_2$, and “” represents the position at which any of structures L-1 to L-27 is joined to the Ar or the $Ar_2$;

optionally, hydrogens in the structures of the L-1 to L-27 can be partially or completely substituted with deuterium.

11. The electroluminescent device of claim 1, wherein the organic layer is an emissive layer, and the first compound and the second compound are host materials.

12. The electroluminescent device of claim 11, wherein the emissive layer further comprises at least one phosphorescent material.

13. The electroluminescent device of claim 12, wherein in the emissive layer, the at least one phosphorescent material is a metal complex, and the metal complex has a general formula of $M(L_a)_m(L_b)_n(L_c)_q$;

wherein M is selected from a metal with a relative atomic mass greater than 40;

$L_a$, $L_b$, and $L_c$ are a first ligand, a second ligand and a third ligand coordinated to the M, respectively; $L_a$, $L_b$, and $L_c$ can be optionally joined to form a multidentate ligand;

$L_a$, $L_b$, and $L_c$ can be identical or different; m is 1, 2 or 3; n is 0, 1 or 2; q is 0 or 1; the sum of m, n, and q equals to the oxidation state of the M; when m is greater than or equal to 2, the plurality of $L_a$ can be identical or different; when n is equal to 2, two $L_b$ can be identical or different;

$L_a$ has a structure represented by Formula 3:

Formula 3

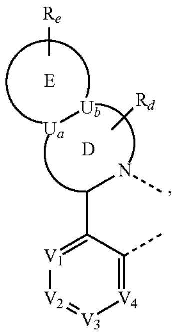, wherein, the ring D is selected from a 5-membered heteroaromatic ring or a 6-membered heteroaromatic ring;

the ring E is selected from a 5-membered unsaturated carbocyclic ring, a benzene ring, a 5-membered heteroaromatic ring or a 6-membered heteroaromatic ring;

the ring D and the ring E are fused via $U_a$ and $U_b$;

$U_a$ and $U_b$ are, at each occurrence identically or differently, selected from C or N;

$R_d$ and $R_e$ represent, at each occurrence identically or differently, mono-substitution, multiple substitutions or non-substitution;

$V_1$ to $V_4$ are, at each occurrence identically or differently, selected from $CR_v$ or N;

$R_d$, $R_e$, and $R_v$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof, adjacent substituents $R_d$, $R_e$, $R_v$ can be optionally joined to form a ring;

$L_b$ and $L_c$ are, at each occurrence identically or differently, selected from any one of the group consisting of the following structures:

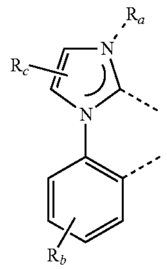
,
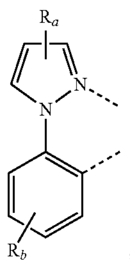
,
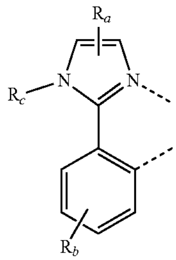
,
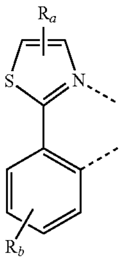
,

-continued

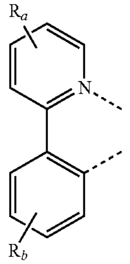
,
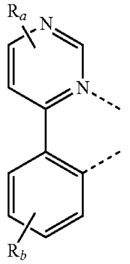
,
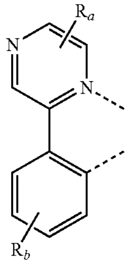
,
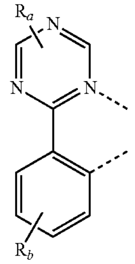
,
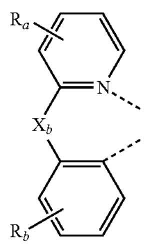
,
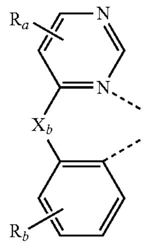
,
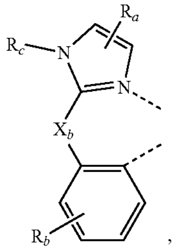
, and
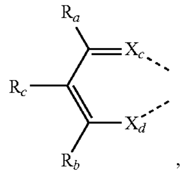
, wherein, $R_a$, $R_b$, and $R_c$ represent, at each occurrence identically or differently, mono-substitution, multiple substitutions or non-substitution;

$X_b$ is, at each occurrence identically or differently, selected from the group consisting of: O, S, Se, $NR_{N1}$, and $CR_{C1}R_{C2}$;

$X_c$ and $X_d$ are, at each occurrence identically or differently, selected from the group consisting of: O, S, Se, and $NR_{N2}$;

$R_a$, $R_b$, $R_c$, $R_{N1}$, $R_{N2}$, $R_{C1}$, and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof, in structures of the ligands $L_b$ and $L_c$, adjacent substituents $R_a$, $R_b$, $R_c$, $R_{N1}$, $R_{N2}$, $R_{C1}$, and $R_{C2}$ can be optionally joined to form a ring.

14. The electroluminescent device of claim 12, wherein in the emissive layer, the at least one phosphorescent material is a metal complex, and the metal complex has a general formula of $M(L_a)_m(L_b)_n$;

wherein M is selected from a metal with a relative atomic mass greater than 40;

$L_a$ and $L_b$ are a first ligand and a second ligand coordinated to the M, respectively; $L_a$ and $L_b$ can be optionally joined to form a multidentate ligand;

m is 1, 2 or 3; n is 0, 1 or 2; the sum of m and n equals to the oxidation state of the M; when m is greater than or equal to 2, the plurality of $L_a$ can be identical or different; when n is equal to 2, two $L_b$ can be identical or different;

$L_a$ has a structure represented by Formula 3:

Formula 3

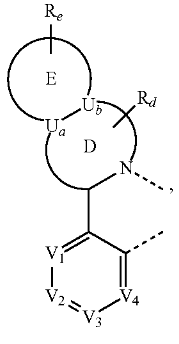

wherein, the ring D is selected from a 5-membered heteroaromatic ring or a 6-membered heteroaromatic ring;

the ring E is selected from a 5-membered unsaturated carbocyclic ring, a benzene ring, a 5-membered heteroaromatic ring or a 6-membered heteroaromatic ring;

the ring D and the ring E are fused via $U_a$ and $U_b$;

$U_a$ and $U_b$ are, at each occurrence identically or differently, selected from C or N;

$R_d$ and $R_e$ represent, at each occurrence identically or differently, mono-substitution, multiple substitutions or non-substitution;

$V_1$ to $V_4$ are, at each occurrence identically or differently, selected from $CR_v$ or N;

$R_d$, $R_e$, and $R_v$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof, adjacent substituents $R_d$, $R_e$, $R_v$ can be optionally joined to form a ring;

the ligand $L_b$ has the following structure:

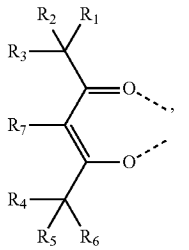

wherein $R_1$ to $R_7$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted heterocyclic group having 3 to 20 ring atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

15. The electroluminescent device of claim 13, wherein the at least one phosphorescent material is an Ir complex, a Pt complex or an Os complex.

16. A display assembly, comprising the electroluminescent device of claim 1.

17. The electroluminescent device of claim 2, R and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, an isocyano group, a hydroxyl group, a sulfanyl group, and combinations thereof.

18. The electroluminescent device of claim 8, Z is selected from O, S, $CR_zR_z$, $SiR_zR_z$ or $NR_z$;

$R_z$ and $R_{Ar}$ are, at each occurrence identically or differently, selected from the group consisting of: hydrogen, deuterium, halogen, cyano, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, and combinations thereof.

19. The electroluminescent device of claim 1, wherein $L_1$ and $L_2$ are, at each occurrence identically or differently, selected from the group consisting of: a single bond, substituted or unsubstituted arylene having 6 to 24 carbon atoms, substituted or unsubstituted heteroarylene having 3 to 24 carbon atoms, and combinations thereof.

20. The electroluminescent device of claim 10, the first compound is selected from the group consisting of Compound 1-1 to Compound 1-322, and the Compound 1-1 to Compound 1-322 each have a structure of $H_1$-$L_1$-$Ar_1$, wherein $H_1$, $L_1$, and $Ar_1$ are respectively selected from the following structures listed in the table below:

| Compound No. | $H_1$ | $L_1$ | $Ar_1$ |
|---|---|---|---|
| 1-1 | H-1 | L-0 | Ar-1 |
| 1-2 | H-1 | L-0 | Ar-2 |
| 1-3 | H-1 | L-0 | Ar-3 |
| 1-4 | H-1 | L-0 | Ar-4 |
| 1-5 | H-1 | L-0 | Ar-5 |
| 1-6 | H-1 | L-0 | Ar-6 |
| 1-7 | H-1 | L-0 | Ar-7 |
| 1-8 | H-1 | L-0 | Ar-8 |
| 1-9 | H-1 | L-0 | Ar-9 |
| 1-10 | H-1 | L-0 | Ar-10 |
| 1-11 | H-1 | L-0 | Ar-11 |
| 1-12 | H-1 | L-0 | Ar-12 |
| 1-13 | H-1 | L-0 | Ar-13 |
| 1-14 | H-1 | L-0 | Ar-14 |
| 1-15 | H-1 | L-0 | Ar-15 |
| 1-16 | H-1 | L-0 | Ar-16 |
| 1-17 | H-1 | L-0 | Ar-17 |
| 1-18 | H-1 | L-0 | Ar-18 |
| 1-19 | H-1 | L-0 | Ar-19 |
| 1-20 | H-1 | L-0 | Ar-20 |
| 1-21 | H-1 | L-0 | Ar-21 |
| 1-22 | H-1 | L-0 | Ar-22 |
| 1-23 | H-1 | L-0 | Ar-23 |
| 1-24 | H-1 | L-0 | Ar-24 |
| 1-25 | H-1 | L-0 | Ar-25 |
| 1-26 | H-1 | L-0 | Ar-26 |
| 1-27 | H-1 | L-0 | Ar-27 |
| 1-28 | H-1 | L-0 | Ar-28 |
| 1-29 | H-1 | L-0 | Ar-29 |
| 1-30 | H-1 | L-0 | Ar-30 |
| 1-31 | H-1 | L-0 | Ar-31 |
| 1-32 | H-1 | L-0 | Ar-32 |
| 1-33 | H-1 | L-0 | Ar-33 |
| 1-34 | H-1 | L-0 | Ar-34 |
| 1-35 | H-1 | L-0 | Ar-35 |
| 1-36 | H-1 | L-0 | Ar-36 |
| 1-37 | H-1 | L-0 | Ar-37 |
| 1-38 | H-1 | L-0 | Ar-38 |
| 1-39 | H-1 | L-0 | Ar-39 |
| 1-40 | H-1 | L-0 | Ar-40 |
| 1-41 | H-1 | L-0 | Ar-41 |
| 1-42 | H-1 | L-0 | Ar-42 |
| 1-43 | H-1 | L-0 | Ar-43 |
| 1-44 | H-1 | L-0 | Ar-44 |
| 1-45 | H-1 | L-0 | Ar-45 |

-continued

| Compound No. | $H_1$ | $L_1$ | $Ar_1$ |
|---|---|---|---|
| 1-46 | H-1 | L-0 | Ar-46 |
| 1-47 | H-1 | L-0 | Ar-47 |
| 1-48 | H-1 | L-0 | Ar-48 |
| 1-49 | H-1 | L-0 | Ar-49 |
| 1-50 | H-1 | L-0 | Ar-50 |
| 1-51 | H-1 | L-0 | Ar-51 |
| 1-52 | H-1 | L-0 | Ar-52 |
| 1-53 | H-1 | L-0 | Ar-53 |
| 1-54 | H-1 | L-1 | Ar-1 |
| 1-55 | H-1 | L-1 | Ar-2 |
| 1-56 | H-1 | L-1 | Ar-3 |
| 1-57 | H-1 | L-1 | Ar-4 |
| 1-58 | H-1 | L-1 | Ar-5 |
| 1-59 | H-1 | L-1 | Ar-6 |
| 1-60 | H-1 | L-1 | Ar-7 |
| 1-61 | H-1 | L-1 | Ar-8 |
| 1-62 | H-1 | L-1 | Ar-9 |
| 1-63 | H-1 | L-1 | Ar-10 |
| 1-64 | H-1 | L-1 | Ar-11 |
| 1-65 | H-1 | L-1 | Ar-12 |
| 1-66 | H-1 | L-1 | Ar-13 |
| 1-67 | H-1 | L-1 | Ar-14 |
| 1-68 | H-1 | L-1 | Ar-15 |
| 1-69 | H-1 | L-1 | Ar-16 |
| 1-70 | H-1 | L-1 | Ar-17 |
| 1-71 | H-1 | L-1 | Ar-18 |
| 1-72 | H-1 | L-1 | Ar-19 |
| 1-73 | H-1 | L-1 | Ar-20 |
| 1-74 | H-1 | L-1 | Ar-21 |
| 1-75 | H-1 | L-1 | Ar-22 |
| 1-76 | H-1 | L-1 | Ar-23 |
| 1-77 | H-1 | L-1 | Ar-24 |
| 1-78 | H-1 | L-1 | Ar-25 |
| 1-79 | H-1 | L-1 | Ar-26 |
| 1-80 | H-1 | L-1 | Ar-27 |
| 1-81 | H-1 | L-1 | Ar-28 |
| 1-82 | H-1 | L-1 | Ar-29 |
| 1-83 | H-1 | L-1 | Ar-30 |
| 1-84 | H-1 | L-1 | Ar-31 |
| 1-85 | H-1 | L-1 | Ar-32 |
| 1-86 | H-1 | L-1 | Ar-33 |
| 1-87 | H-1 | L-1 | Ar-34 |
| 1-88 | H-1 | L-1 | Ar-35 |
| 1-89 | H-1 | L-1 | Ar-36 |
| 1-90 | H-1 | L-1 | Ar-37 |
| 1-91 | H-1 | L-1 | Ar-38 |
| 1-92 | H-1 | L-1 | Ar-39 |
| 1-93 | H-1 | L-1 | Ar-40 |
| 1-94 | H-1 | L-1 | Ar-41 |
| 1-95 | H-1 | L-1 | Ar-42 |
| 1-96 | H-1 | L-1 | Ar-43 |
| 1-97 | H-1 | L-1 | Ar-44 |
| 1-98 | H-1 | L-1 | Ar-45 |
| 1-99 | H-1 | L-1 | Ar-46 |
| 1-100 | H-1 | L-1 | Ar-47 |
| 1-101 | H-1 | L-1 | Ar-48 |
| 1-102 | H-1 | L-1 | Ar-49 |
| 1-103 | H-1 | L-1 | Ar-50 |
| 1-104 | H-1 | L-1 | Ar-51 |
| 1-105 | H-1 | L-1 | Ar-52 |
| 1-106 | H-1 | L-1 | Ar-53 |
| 1-107 | H-1 | L-3 | Ar-1 |
| 1-108 | H-1 | L-3 | Ar-2 |
| 1-109 | H-1 | L-3 | Ar-3 |
| 1-110 | H-1 | L-3 | Ar-4 |
| 1-111 | H-1 | L-3 | Ar-5 |
| 1-112 | H-1 | L-3 | Ar-6 |
| 1-113 | H-1 | L-3 | Ar-7 |
| 1-114 | H-1 | L-3 | Ar-8 |
| 1-115 | H-1 | L-3 | Ar-9 |
| 1-116 | H-1 | L-3 | Ar-10 |
| 1-117 | H-1 | L-3 | Ar-11 |
| 1-118 | H-1 | L-3 | Ar-12 |
| 1-119 | H-1 | L-3 | Ar-13 |
| 1-120 | H-1 | L-3 | Ar-14 |
| 1-121 | H-1 | L-3 | Ar-15 |

-continued

| Compound No. | $H_1$ | $L_1$ | $Ar_1$ |
|---|---|---|---|
| 1-122 | H-1 | L-3 | Ar-16 |
| 1-123 | H-1 | L-3 | Ar-17 |
| 1-124 | H-1 | L-3 | Ar-18 |
| 1-125 | H-1 | L-3 | Ar-19 |
| 1-126 | H-1 | L-3 | Ar-20 |
| 1-127 | H-1 | L-3 | Ar-21 |
| 1-128 | H-1 | L-3 | Ar-22 |
| 1-129 | H-1 | L-3 | Ar-23 |
| 1-130 | H-1 | L-3 | Ar-24 |
| 1-131 | H-1 | L-3 | Ar-25 |
| 1-132 | H-1 | L-3 | Ar-26 |
| 1-133 | H-1 | L-3 | Ar-27 |
| 1-134 | H-1 | L-3 | Ar-28 |
| 1-135 | H-1 | L-3 | Ar-29 |
| 1-136 | H-1 | L-3 | Ar-30 |
| 1-137 | H-1 | L-3 | Ar-31 |
| 1-138 | H-1 | L-3 | Ar-32 |
| 1-139 | H-1 | L-3 | Ar-33 |
| 1-140 | H-1 | L-3 | Ar-34 |
| 1-141 | H-1 | L-3 | Ar-35 |
| 1-142 | H-1 | L-3 | Ar-36 |
| 1-143 | H-1 | L-3 | Ar-37 |
| 1-144 | H-1 | L-3 | Ar-38 |
| 1-145 | H-1 | L-3 | Ar-39 |
| 1-146 | H-1 | L-3 | Ar-40 |
| 1-147 | H-1 | L-3 | Ar-41 |
| 1-148 | H-1 | L-3 | Ar-42 |
| 1-149 | H-1 | L-3 | Ar-43 |
| 1-150 | H-1 | L-3 | Ar-44 |
| 1-151 | H-1 | L-3 | Ar-45 |
| 1-152 | H-1 | L-3 | Ar-46 |
| 1-153 | H-1 | L-3 | Ar-47 |
| 1-154 | H-1 | L-3 | Ar-48 |
| 1-155 | H-1 | L-3 | Ar-49 |
| 1-156 | H-1 | L-3 | Ar-50 |
| 1-157 | H-1 | L-3 | Ar-51 |
| 1-158 | H-1 | L-3 | Ar-52 |
| 1-159 | H-1 | L-3 | Ar-53 |
| 1-160 | H-1 | L-2 | Ar-1 |
| 1-161 | H-1 | L-4 | Ar-1 |
| 1-162 | H-1 | L-5 | Ar-1 |
| 1-163 | H-1 | L-6 | Ar-1 |
| 1-164 | H-1 | L-7 | Ar-1 |
| 1-165 | H-1 | L-8 | Ar-1 |
| 1-166 | H-1 | L-9 | Ar-1 |
| 1-167 | H-1 | L-10 | Ar-1 |
| 1-168 | H-1 | L-11 | Ar-1 |
| 1-169 | H-1 | L-12 | Ar-1 |
| 1-170 | H-1 | L-13 | Ar-1 |
| 1-171 | H-1 | L-14 | Ar-1 |
| 1-172 | H-1 | L-15 | Ar-1 |
| 1-173 | H-1 | L-16 | Ar-1 |
| 1-174 | H-1 | L-17 | Ar-1 |
| 1-175 | H-1 | L-18 | Ar-1 |
| 1-176 | H-1 | L-19 | Ar-1 |
| 1-177 | H-1 | L-20 | Ar-1 |
| 1-178 | H-1 | L-21 | Ar-1 |
| 1-179 | H-1 | L-22 | Ar-1 |
| 1-180 | H-1 | L-23 | Ar-1 |
| 1-181 | H-1 | L-24 | Ar-1 |
| 1-182 | H-1 | L-25 | Ar-1 |
| 1-183 | H-1 | L-26 | Ar-1 |
| 1-184 | H-1 | L-27 | Ar-1 |
| 1-185 | H-2 | L-0 | Ar-1 |
| 1-186 | H-3 | L-0 | Ar-1 |
| 1-187 | H-4 | L-0 | Ar-1 |
| 1-188 | H-5 | L-0 | Ar-1 |
| 1-189 | H-6 | L-0 | Ar-1 |
| 1-190 | H-7 | L-0 | Ar-1 |
| 1-191 | H-8 | L-0 | Ar-1 |
| 1-192 | H-9 | L-0 | Ar-1 |
| 1-193 | H-10 | L-0 | Ar-1 |
| 1-194 | H-11 | L-0 | Ar-1 |
| 1-195 | H-12 | L-0 | Ar-1 |
| 1-196 | H-13 | L-0 | Ar-1 |
| 1-197 | H-14 | L-0 | Ar-1 |

-continued

| Compound No. | $H_1$ | $L_1$ | $Ar_1$ |
|---|---|---|---|
| 1-198 | H-15 | L-0 | Ar-1 |
| 1-199 | H-16 | L-0 | Ar-1 |
| 1-200 | H-17 | L-0 | Ar-1 |
| 1-201 | H-18 | L-0 | Ar-1 |
| 1-202 | H-19 | L-0 | Ar-1 |
| 1-203 | H-20 | L-0 | Ar-1 |
| 1-204 | H-21 | L-0 | Ar-1 |
| 1-205 | H-22 | L-0 | Ar-1 |
| 1-206 | H-23 | L-0 | Ar-1 |
| 1-207 | H-24 | L-0 | Ar-1 |
| 1-208 | H-25 | L-0 | Ar-1 |
| 1-209 | H-26 | L-0 | Ar-1 |
| 1-210 | H-27 | L-0 | Ar-1 |
| 1-211 | H-28 | L-0 | Ar-1 |
| 1-212 | H-29 | L-0 | Ar-1 |
| 1-213 | H-30 | L-0 | Ar-1 |
| 1-214 | H-31 | L-0 | Ar-1 |
| 1-215 | H-32 | L-0 | Ar-1 |
| 1-216 | H-33 | L-0 | Ar-1 |
| 1-217 | H-34 | L-0 | Ar-1 |
| 1-218 | H-35 | L-0 | Ar-1 |
| 1-219 | H-36 | L-0 | Ar-1 |
| 1-220 | H-37 | L-0 | Ar-1 |
| 1-221 | H-38 | L-0 | Ar-1 |
| 1-222 | H-39 | L-0 | Ar-1 |
| 1-223 | H-40 | L-0 | Ar-1 |
| 1-224 | H-41 | L-0 | Ar-1 |
| 1-225 | H-42 | L-0 | Ar-1 |
| 1-226 | H-43 | L-0 | Ar-1 |
| 1-227 | H-44 | L-0 | Ar-1 |
| 1-228 | H-45 | L-0 | Ar-1 |
| 1-229 | H-46 | L-0 | Ar-1 |
| 1-230 | H-47 | L-0 | Ar-1 |
| 1-231 | H-48 | L-0 | Ar-1 |
| 1-232 | H-49 | L-0 | Ar-1 |
| 1-233 | H-50 | L-0 | Ar-1 |
| 1-234 | H-51 | L-0 | Ar-1 |
| 1-235 | H-52 | L-0 | Ar-1 |
| 1-236 | H-53 | L-0 | Ar-1 |
| 1-237 | H-54 | L-0 | Ar-1 |
| 1-238 | H-55 | L-0 | Ar-1 |
| 1-239 | H-56 | L-0 | Ar-1 |
| 1-240 | H-57 | L-0 | Ar-1 |
| 1-241 | H-58 | L-0 | Ar-1 |
| 1-242 | H-59 | L-0 | Ar-1 |
| 1-243 | H-60 | L-0 | Ar-1 |
| 1-244 | H-61 | L-0 | Ar-1 |
| 1-245 | H-62 | L-0 | Ar-1 |
| 1-246 | H-63 | L-0 | Ar-1 |
| 1-247 | H-64 | L-0 | Ar-1 |
| 1-248 | H-65 | L-0 | Ar-1 |
| 1-249 | H-66 | L-0 | Ar-1 |
| 1-250 | H-67 | L-0 | Ar-1 |
| 1-251 | H-68 | L-0 | Ar-1 |
| 1-252 | H-69 | L-0 | Ar-1 |
| 1-253 | H-70 | L-0 | Ar-1 |
| 1-254 | H-71 | L-0 | Ar-1 |
| 1-255 | H-72 | L-0 | Ar-1 |
| 1-256 | H-73 | L-0 | Ar-1 |
| 1-257 | H-74 | L-0 | Ar-1 |
| 1-258 | H-75 | L-0 | Ar-1 |
| 1-259 | H-76 | L-0 | Ar-1 |
| 1-260 | H-77 | L-0 | Ar-1 |
| 1-261 | H-78 | L-0 | Ar-1 |
| 1-262 | H-79 | L-0 | Ar-1 |
| 1-263 | H-80 | L-0 | Ar-1 |
| 1-264 | H-81 | L-0 | Ar-1 |
| 1-265 | H-82 | L-0 | Ar-1 |
| 1-266 | H-83 | L-0 | Ar-1 |
| 1-267 | H-84 | L-0 | Ar-1 |
| 1-268 | H-85 | L-0 | Ar-1 |
| 1-269 | H-86 | L-0 | Ar-1 |
| 1-270 | H-87 | L-0 | Ar-1 |
| 1-271 | H-88 | L-0 | Ar-1 |
| 1-272 | H-89 | L-0 | Ar-1 |
| 1-273 | H-90 | L-0 | Ar-1 |

-continued

| Compound No. | $H_1$ | $L_1$ | $Ar_1$ |
|---|---|---|---|
| 1-274 | H-91 | L-0 | Ar-1 |
| 1-275 | H-92 | L-0 | Ar-1 |
| 1-276 | H-93 | L-0 | Ar-1 |
| 1-277 | H-94 | L-0 | Ar-1 |
| 1-278 | H-95 | L-0 | Ar-1 |
| 1-279 | H-96 | L-0 | Ar-1 |
| 1-280 | H-97 | L-0 | Ar-1 |
| 1-281 | H-98 | L-0 | Ar-1 |
| 1-282 | H-99 | L-0 | Ar-1 |
| 1-283 | H-100 | L-0 | Ar-1 |
| 1-284 | H-101 | L-0 | Ar-1 |
| 1-285 | H-102 | L-0 | Ar-1 |
| 1-286 | H-103 | L-0 | Ar-1 |
| 1-287 | H-104 | L-0 | Ar-1 |
| 1-288 | H-105 | L-0 | Ar-1 |
| 1-289 | H-106 | L-0 | Ar-1 |
| 1-290 | H-107 | L-0 | Ar-1 |
| 1-291 | H-108 | L-0 | Ar-1 |
| 1-292 | H-109 | L-0 | Ar-1 |
| 1-293 | H-110 | L-0 | Ar-1 |
| 1-294 | H-111 | L-0 | Ar-1 |
| 1-295 | H-112 | L-0 | Ar-1 |
| 1-296 | H-113 | L-0 | Ar-1 |
| 1-297 | H-114 | L-0 | Ar-1 |
| 1-298 | H-115 | L-0 | Ar-1 |
| 1-299 | H-116 | L-0 | Ar-1 |
| 1-300 | H-117 | L-0 | Ar-1 |
| 1-301 | H-118 | L-0 | Ar-1 |
| 1-302 | H-119 | L-0 | Ar-1 |
| 1-303 | H-120 | L-0 | Ar-1 |
| 1-304 | H-121 | L-0 | Ar-1 |
| 1-305 | H-122 | L-0 | Ar-1 |
| 1-306 | H-123 | L-0 | Ar-1 |
| 1-307 | H-124 | L-0 | Ar-1 |
| 1-308 | H-125 | L-0 | Ar-1 |
| 1-309 | H-126 | L-0 | Ar-1 |
| 1-310 | H-127 | L-0 | Ar-1 |
| 1-311 | H-128 | L-0 | Ar-1 |
| 1-312 | H-129 | L-0 | Ar-1 |
| 1-313 | H-130 | L-0 | Ar-1 |
| 1-314 | H-131 | L-0 | Ar-1 |
| 1-315 | H-132 | L-0 | Ar-1 |
| 1-316 | H-133 | L-0 | Ar-1 |
| 1-317 | H-134 | L-0 | Ar-1 |
| 1-318 | H-135 | L-0 | Ar-1 |
| 1-319 | H-136 | L-0 | Ar-1 |
| 1-320 | H-137 | L-0 | Ar-1 |
| 1-321 | H-138 | L-0 | Ar-1 |
| 1-322 | H-139 | L-0 | Ar-1 |

optionally, hydrogens in the Compound 1-1 to Compound 1-322 can be partially or completely substituted with deuterium.

21. The electroluminescent device of claim 10, the second compound is selected from the group consisting of Compound 2-1 to Compound 2-169, Compound 2-212 to Compound 2-221, and Compound 2-264 to Compound 2-273, and the Compound 2-1 to Compound 2-169, Compound 2-212 to Compound 2-221, and Compound 2-264 to Compound 2-273 each have a structure of $H_2$-$L_2$-$Ar_2$, wherein $H_2$, $L_2$, and $Ar_2$ are respectively selected from the following structures listed in the table below:

| Compound No. | $H_2$ | $L_2$ | $Ar_2$ |
|---|---|---|---|
| 2-1 | H2-1 | L-0 | Ar-1 |
| 2-2 | H2-1 | L-0 | Ar-2 |
| 2-3 | H2-1 | L-0 | Ar-3 |
| 2-4 | H2-1 | L-0 | Ar-4 |
| 2-5 | H2-1 | L-0 | Ar-5 |
| 2-6 | H2-1 | L-0 | Ar-6 |
| 2-7 | H2-1 | L-0 | Ar-7 |
| 2-8 | H2-1 | L-0 | Ar-8 |
| 2-9 | H2-1 | L-0 | Ar-9 |
| 2-10 | H2-1 | L-0 | Ar-10 |
| 2-11 | H2-1 | L-0 | Ar-11 |
| 2-12 | H2-1 | L-0 | Ar-12 |
| 2-13 | H2-1 | L-0 | Ar-13 |
| 2-14 | H2-1 | L-0 | Ar-14 |
| 2-15 | H2-1 | L-0 | Ar-15 |
| 2-16 | H2-1 | L-0 | Ar-16 |
| 2-17 | H2-1 | L-0 | Ar-17 |
| 2-18 | H2-1 | L-0 | Ar-18 |
| 2-19 | H2-1 | L-0 | Ar-19 |
| 2-20 | H2-1 | L-0 | Ar-20 |
| 2-21 | H2-1 | L-0 | Ar-21 |
| 2-22 | H2-1 | L-0 | Ar-22 |
| 2-23 | H2-1 | L-0 | Ar-23 |
| 2-24 | H2-1 | L-0 | Ar-24 |
| 2-25 | H2-1 | L-0 | Ar-25 |
| 2-26 | H2-1 | L-0 | Ar-26 |
| 2-27 | H2-1 | L-0 | Ar-27 |
| 2-28 | H2-1 | L-0 | Ar-28 |
| 2-29 | H2-1 | L-0 | Ar-29 |
| 2-30 | H2-1 | L-0 | Ar-30 |
| 2-31 | H2-1 | L-0 | Ar-31 |
| 2-32 | H2-1 | L-0 | Ar-32 |
| 2-33 | H2-1 | L-0 | Ar-33 |
| 2-34 | H2-1 | L-0 | Ar-34 |
| 2-35 | H2-1 | L-0 | Ar-35 |
| 2-36 | H2-1 | L-0 | Ar-36 |
| 2-37 | H2-1 | L-0 | Ar-37 |
| 2-38 | H2-1 | L-0 | Ar-38 |
| 2-39 | H2-1 | L-0 | Ar-39 |
| 2-40 | H2-1 | L-0 | Ar-40 |
| 2-41 | H2-1 | L-0 | Ar-41 |
| 2-42 | H2-1 | L-0 | Ar-42 |
| 2-43 | H2-1 | L-0 | Ar-43 |
| 2-44 | H2-1 | L-0 | Ar-44 |
| 2-45 | H2-1 | L-0 | Ar-45 |
| 2-46 | H2-1 | L-0 | Ar-46 |
| 2-47 | H2-1 | L-0 | Ar-47 |
| 2-48 | H2-1 | L-0 | Ar-48 |
| 2-49 | H2-1 | L-0 | Ar-49 |
| 2-50 | H2-1 | L-0 | Ar-50 |
| 2-51 | H2-1 | L-0 | Ar-51 |
| 2-52 | H2-1 | L-0 | Ar-52 |
| 2-53 | H2-1 | L-0 | Ar-53 |
| 2-54 | H2-1 | L-1 | Ar-1 |
| 2-55 | H2-1 | L-1 | Ar-2 |
| 2-56 | H2-1 | L-1 | Ar-3 |
| 2-57 | H2-1 | L-1 | Ar-4 |
| 2-58 | H2-1 | L-1 | Ar-5 |
| 2-59 | H2-1 | L-1 | Ar-6 |
| 2-60 | H2-1 | L-1 | Ar-7 |
| 2-61 | H2-1 | L-1 | Ar-8 |
| 2-62 | H2-1 | L-1 | Ar-9 |
| 2-63 | H2-1 | L-1 | Ar-10 |
| 2-64 | H2-1 | L-1 | Ar-11 |
| 2-65 | H2-1 | L-1 | Ar-12 |
| 2-66 | H2-1 | L-1 | Ar-13 |
| 2-67 | H2-1 | L-1 | Ar-14 |
| 2-68 | H2-1 | L-1 | Ar-15 |
| 2-69 | H2-1 | L-1 | Ar-16 |
| 2-70 | H2-1 | L-1 | Ar-17 |
| 2-71 | H2-1 | L-1 | Ar-18 |
| 2-72 | H2-1 | L-1 | Ar-19 |
| 2-73 | H2-1 | L-1 | Ar-20 |
| 2-74 | H2-1 | L-1 | Ar-21 |
| 2-75 | H2-1 | L-1 | Ar-22 |
| 2-76 | H2-1 | L-1 | Ar-23 |
| 2-77 | H2-1 | L-1 | Ar-24 |
| 2-78 | H2-1 | L-1 | Ar-25 |
| 2-79 | H2-1 | L-1 | Ar-26 |
| 2-80 | H2-1 | L-1 | Ar-27 |
| 2-81 | H2-1 | L-1 | Ar-28 |

-continued

| Compound No. | $H_2$ | $L_2$ | $Ar_2$ |
|---|---|---|---|
| 2-82 | H2-1 | L-1 | Ar-29 |
| 2-83 | H2-1 | L-1 | Ar-30 |
| 2-84 | H2-1 | L-1 | Ar-31 |
| 2-85 | H2-1 | L-1 | Ar-32 |
| 2-86 | H2-1 | L-1 | Ar-33 |
| 2-87 | H2-1 | L-1 | Ar-34 |
| 2-88 | H2-1 | L-1 | Ar-35 |
| 2-89 | H2-1 | L-1 | Ar-36 |
| 2-90 | H2-1 | L-1 | Ar-37 |
| 2-91 | H2-1 | L-1 | Ar-38 |
| 2-92 | H2-1 | L-1 | Ar-39 |
| 2-93 | H2-1 | L-1 | Ar-40 |
| 2-94 | H2-1 | L-1 | Ar-41 |
| 2-95 | H2-1 | L-1 | Ar-42 |
| 2-96 | H2-1 | L-1 | Ar-43 |
| 2-97 | H2-1 | L-1 | Ar-44 |
| 2-98 | H2-1 | L-1 | Ar-45 |
| 2-99 | H2-1 | L-1 | Ar-46 |
| 2-100 | H2-1 | L-1 | Ar-47 |
| 2-101 | H2-1 | L-1 | Ar-48 |
| 2-102 | H2-1 | L-1 | Ar-49 |
| 2-103 | H2-1 | L-1 | Ar-50 |
| 2-104 | H2-1 | L-1 | Ar-51 |
| 2-105 | H2-1 | L-1 | Ar-52 |
| 2-106 | H2-1 | L-1 | Ar-53 |
| 2-107 | H2-1 | L-3 | Ar-1 |
| 2-108 | H2-1 | L-3 | Ar-2 |
| 2-109 | H2-1 | L-3 | Ar-3 |
| 2-110 | H2-1 | L-3 | Ar-4 |
| 2-111 | H2-1 | L-3 | Ar-5 |
| 2-112 | H2-1 | L-3 | Ar-6 |
| 2-113 | H2-1 | L-3 | Ar-7 |
| 2-114 | H2-1 | L-3 | Ar-8 |
| 2-115 | H2-1 | L-3 | Ar-9 |
| 2-116 | H2-1 | L-3 | Ar-10 |
| 2-117 | H2-1 | L-3 | Ar-11 |
| 2-118 | H2-1 | L-3 | Ar-12 |
| 2-119 | H2-1 | L-3 | Ar-13 |
| 2-120 | H2-1 | L-3 | Ar-14 |
| 2-121 | H2-1 | L-3 | Ar-15 |
| 2-122 | H2-1 | L-3 | Ar-16 |
| 2-123 | H2-1 | L-3 | Ar-17 |
| 2-124 | H2-1 | L-3 | Ar-18 |
| 2-125 | H2-1 | L-3 | Ar-19 |
| 2-126 | H2-1 | L-3 | Ar-20 |
| 2-127 | H2-1 | L-3 | Ar-21 |
| 2-128 | H2-1 | L-3 | Ar-22 |
| 2-129 | H2-1 | L-3 | Ar-23 |
| 2-130 | H2-1 | L-3 | Ar-24 |
| 2-131 | H2-1 | L-3 | Ar-25 |
| 2-132 | H2-1 | L-3 | Ar-26 |
| 2-133 | H2-1 | L-3 | Ar-27 |
| 2-134 | H2-1 | L-3 | Ar-28 |
| 2-135 | H2-1 | L-3 | Ar-29 |
| 2-136 | H2-1 | L-3 | Ar-30 |
| 2-137 | H2-1 | L-3 | Ar-31 |
| 2-138 | H2-1 | L-3 | Ar-32 |
| 2-139 | H2-1 | L-3 | Ar-33 |
| 2-140 | H2-1 | L-3 | Ar-34 |
| 2-141 | H2-1 | L-3 | Ar-35 |
| 2-142 | H2-1 | L-3 | Ar-36 |
| 2-143 | H2-1 | L-3 | Ar-37 |
| 2-144 | H2-1 | L-3 | Ar-38 |
| 2-145 | H2-1 | L-3 | Ar-39 |
| 2-146 | H2-1 | L-3 | Ar-40 |
| 2-147 | H2-1 | L-3 | Ar-41 |
| 2-148 | H2-1 | L-3 | Ar-42 |

-continued

| Compound No. | $H_2$ | $L_2$ | $Ar_2$ |
|---|---|---|---|
| 2-149 | H2-1 | L-3 | Ar-43 |
| 2-150 | H2-1 | L-3 | Ar-44 |
| 2-151 | H2-1 | L-3 | Ar-45 |
| 2-152 | H2-1 | L-3 | Ar-46 |
| 2-153 | H2-1 | L-3 | Ar-47 |
| 2-154 | H2-1 | L-3 | Ar-48 |
| 2-155 | H2-1 | L-3 | Ar-49 |
| 2-156 | H2-1 | L-3 | Ar-50 |
| 2-157 | H2-1 | L-3 | Ar-51 |
| 2-158 | H2-1 | L-3 | Ar-52 |
| 2-159 | H2-1 | L-3 | Ar-53 |
| 2-160 | H2-2 | L-0 | Ar-1 |
| 2-161 | H2-3 | L-0 | Ar-1 |
| 2-162 | H2-4 | L-0 | Ar-1 |
| 2-163 | H2-5 | L-0 | Ar-1 |
| 2-164 | H2-6 | L-0 | Ar-1 |
| 2-165 | H2-7 | L-0 | Ar-1 |
| 2-166 | H2-8 | L-0 | Ar-1 |
| 2-167 | H2-9 | L-0 | Ar-1 |
| 2-168 | H2-10 | L-0 | Ar-1 |
| 2-169 | H2-11 | L-0 | Ar-1 |
| 2-212 | H2-2 | L-0 | Ar-25 |
| 2-213 | H2-3 | L-0 | Ar-25 |
| 2-214 | H2-4 | L-0 | Ar-25 |
| 2-215 | H2-5 | L-0 | Ar-25 |
| 2-216 | H2-6 | L-0 | Ar-25 |
| 2-217 | H2-7 | L-0 | Ar-25 |
| 2-218 | H2-8 | L-0 | Ar-25 |
| 2-219 | H2-9 | L-0 | Ar-25 |
| 2-220 | H2-10 | L-0 | Ar-25 |
| 2-221 | H2-11 | L-0 | Ar-25 |
| 2-264 | H2-1 | L-0 | Ar-19 |
| 2-265 | H2-2 | L-0 | Ar-19 |
| 2-266 | H2-3 | L-0 | Ar-19 |
| 2-267 | H2-4 | L-0 | Ar-19 |
| 2-268 | H2-5 | L-0 | Ar-19 |
| 2-269 | H2-6 | L-0 | Ar-19 |
| 2-270 | H2-7 | L-0 | Ar-19 |
| 2-271 | H2-8 | L-0 | Ar-19 |
| 2-272 | H2-9 | L-0 | Ar-19 |
| 2-273 | H2-10 | L-0 | Ar-19 |

optionally, hydrogens in the Compound 2-1 to Compound 2-169, Compound 2-212 to Compound 2-221, and Compound 2-264 to Compound 2-273 can be partially or completely substituted with deuterium.

22. The electroluminescent device of claim 14, at least one or two of $R_1$ to $R_3$ are selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms or combinations thereof, and/or at least one or two of $R_4$ to $R_6$ are selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, or combinations thereof.

23. The electroluminescent device of claim 15, wherein the at least one phosphorescent material is an Ir complex and has a structure represented by any one of $Ir(L_a)(L_b)(L_c)$, $Ir(L_a)_2(L_b)$, $Ir(L_a)_2(L_c)$ or $Ir(L_a)(L_c)_2$.

* * * * *